(12) United States Patent
Boyd et al.

(10) Patent No.: US 6,353,019 B1
(45) Date of Patent: Mar. 5, 2002

(54) MACROCYCLIC LACTONES, COMPOSITIONS, AND METHODS OF USE

(75) Inventors: Michael R. Boyd, Ijamsville; Tawnya C. McKee, Gaithersburg; John H. Cardellina, II, Walkersville; John A. Beutler, Braddock Heights, all of MD (US); Karen Erickson, N. Oxford, MA (US); Deborah Galinis, Yardley, PA (US); Lewis Pannell, Silver Springs, MD (US)

(73) Assignee: United States of America as represented by the Department of Health and Human Services, Rockville, MD (US)

( * ) Notice: Subject to any disclaimer, the term of this patent is extended or adjusted under 35 U.S.C. 154(b) by 0 days.

(21) Appl. No.: 09/463,037

(22) PCT Filed: Jul. 23, 1998

(86) PCT No.: PCT/IS98/15011

§ 371 Date: Apr. 10, 2000

§ 102(e) Date: Apr. 10, 2000

(87) PCT Pub. No.: WO99/05136

PCT Pub. Date: Feb. 4, 1999

Related U.S. Application Data

(60) Provisional application No. 60/053,784, filed on Jul. 25, 1997.

(51) Int. Cl.[7] ...................... A61K 31/335; C07D 313/06
(52) U.S. Cl. ........................................ 514/450; 549/270
(58) Field of Search ..................... 514/450; 549/269, 549/270

(56) References Cited

U.S. PATENT DOCUMENTS

| | | | |
|---|---|---|---|
| 5,430,053 A | | 7/1995 | Pettit et al. |
| 5,965,604 A | * | 10/1999 | Yamashita et al. ........... 514/450 |
| 5,977,165 A | * | 11/1999 | Agatsuma et al. .......... 514/450 |
| 6,121,257 A | * | 9/2000 | Kawai et al. ................ 514/214 |
| 6,124,453 A | * | 9/2000 | Fehr et al. ................... 540/456 |
| 6,207,826 B1 | * | 3/2001 | Cook et al. .................. 540/472 |

FOREIGN PATENT DOCUMENTS

| | | |
|---|---|---|
| EP | 0 350 430 | 1/1990 |
| WO | WO 98/25929 | 6/1998 |

OTHER PUBLICATIONS

Kunze et al, CA130:194051, 1999.*
Kim et al, CA130:177226, 1998.*
Suzumura et al, CA 128:32164, 1997.*
Aldridge et al., *J. Chem. Soc. (C)*, 1623–1627 (1971).
Arabshahi et al., *Tetrahedron Letters*, 29, 10, 1099–1102 (1988).
Benslimane et al., *Journal of Natural Products*, 51, 3, 582–583 (1988).

Boyd et al., *Cytotoxic Anticancer Drugs: Models and Concepts for Drug Discovery and Development*, (Valeriote, F.A., et al., eds.), Amsterdam: Kluwer Academic Publishers, 11–34 (1992).

Boyd et al., *Drug Development Research*, 34, 91–109 (1995).

Boyd, *Anticancer Drug Development Guide: Preclinical Screening, Clinical Trials, and Approval*, B. Teicher, Humana Press Inc. (eds.), 23–42 (1997).

Boyd, *Current Therapy in Oncology*, (ED: JE Neiderhuber) 11–22 (1993).

(List continued on next page.)

Primary Examiner—Deborah C. Lambkin
(74) Attorney, Agent, or Firm—Leydig, Voit & Mayer, Ltd.

(57) ABSTRACT

The present invention provides compound of the formula:

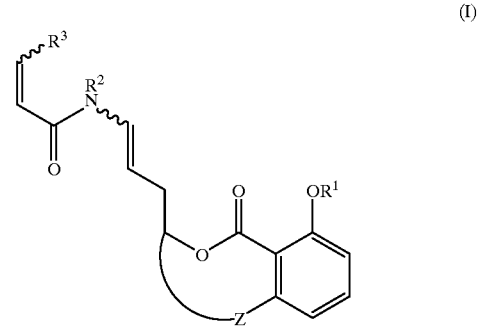

(I)

wherein $R^1$ and $R^2$ are the same or different and are independently H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated or unsaturated alkyl, or aryl; $R^3$ is H, $C_1$→$C_6$ straight-chain or branched-chain saturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms (including heteroatoms) which atoms, together with the five atoms beginning with the carbon of the aromatic ring in meta-relationship with $OR^1$ and ending with the carbon directly attached to the alkyl oxygen of the lactone, which carbons are covalently bonded to either end of linker Z, integrally form a 12–15 membered ring; or a pharmaceutically acceptable salt, an ester, or a prodrug thereof.

The present invention further provides a pharmaceutical composition, and a method of preventing or treating cancer, using at least one compound of the present invention, optionally in conjunction with an additional compound other than a compound of the present invention.

21 Claims, 19 Drawing Sheets

OTHER PUBLICATIONS

Carmeli et al., *Journal of Natural Products*, 53, 6, 1533–1542 (1990).
Carroll et al., *Aust. J. Chem.*, 46, 825–832 (1993).
Carter et al., *Journal of the American Chemical Society*, 7441–7442 (1978).
Charan, et al., *Tetrahedron*, 52, 27, 9111–9120 (1996).
Copp et al., *Tetrahedron Letters*, 30, 28, 3703–3706 (1989).
Dale et al., *Journal of the American Chemical Society*, 95, 2, 512–519 (1973).
D'Auria et al., *Tetrahedron*, 49, 38, 8657–8664 (1993).
Doi et al., *Tetrahedron*, 50, 29, 8651–8656 (1994).
Faulkner, *Natural Product Reports*, 497–539 (1993).
Fenical, *Marine Technology Society*, 388–394 (1974).
Fu et al., *J. Am. Chem. Soc.*, 116, 12125–12126 (1994).
Fusetani et al., *Tetrahedron Letters*, 30, 21, 2809–2812 (1989).
Gordon et al., *J. Org. Chem.*, 49, 97–100 (1984).
Grever et al., *Cancer Principles and Practice of Oncology* $5^{th\ Ed}$., (DeVita et al., eds.), Philadelphia: Lippincott Raven, 385–394 (1997).
Guella et al., *Helvetica Chimica Acta*, 70, 621–626 (1987).
Howard et al., *Tetrahedron Letters*, 46, 4449–4452 (1979).
Jaspars et al., *Journal of Organic Chemistry*, 59, 3253–3255 (1994).
Kaneko et al., *Tetrahedron Letters*, 35, 24, 4107–4110 (1994).
Kernan et al., *J. Org. Chem.*, 53, 5014–5020 (1988).
Kernan et al., *Tetrahedron Letters*, 28, 25, 2809–2812 (1987).
Kim et al., *Journal of Natural Products*, 56, 10, 1813–1816 (1993).
Kobayashi et al., *J. Org. Chem.*, 59, 255–257 (1994).
Kobayashi et al., *Journal of Natural Products*, 56, 5, 787–791 (1993).
Kobayashi et al., *Tetrahedron*, 51, 13, 3727–3736 (1995).
Leclercq et al., *Tetrahedron*, 50, 28, 8465–8478 (1994).
Matsunaga et al., *J. Am. Chem. Soc.*, 108, 847–849 (1986).
Mohamadi et al., *Journal of Computational Chemistry*, 11, 4, 440–467 (1990).
Monks et al., *Journal of the National Cancer Institute*, 83, 11, 757–766 (1991).
Murray et al., *Aust. J. Chem.*, 48, 1253–1266 (1995).
Oh et al., *J. Org. Chem.*, 54, 4499–4503 (1989).
Ohtani et al., *J. Org. Chem.*, 56, 1296–1298 (1991).
Parameswaran et al., *Chemical Abstracts*, 120: 187482v, 600 (1994).
Paull et al., *Cancer Chemotherapeutic Agents*, (Foye ed.), Washington, D.C.,: American Chemical Society Books, 9–45 (1995).
Rashid et al., *Journal of Natural Products*, 58, 7, 1120–1125 (1995).
Rochfort et al., *Aust. J. Chem.*, 49, 1217–1219 (1996).
Roesener et al., *J. Am. Chem. Soc.*, 108, 846–847 (1986).
Rubinstein et al., *Journal of the National Cancer Institute*, 82, 13, 1113–1118 (1990).
Sausville, *Anticancer Drug Development Guide: Preclinical Screening, Clinical Trials, and Approval*, B. Teicher Humana Press Inc. (eds.), 217–226 (1997).
Shen et al., *Chemical Abstracts*, 125:82280 c, 7, 740 (1996).
Skehan et al., *Journal of the National Cancer Institute*, 82, 13, 1107–1112 (1990).
Stinson et al., *Anticancer Research*, 12, 1035–1054 (1992).
Targett et al., *Journal of Natural Products*, 47, 3, 556–557 (1984).
Urry et al., *Tetrahedron Letters*, 8, 27, 3109–3114 (1966).
Venkateswarlu et al., *Journal of Natural Products*, 57, 9, 1283–1285 (1994).
Weinstein et al., *Science*, 275, 343–349 (1997).
Wolkowski, et al., *Tetrahedron Letters*, 565–568 (1972).
Zeng et al., *Chemical Abstracts*, 123:193621t, 695 (1995).

* cited by examiner

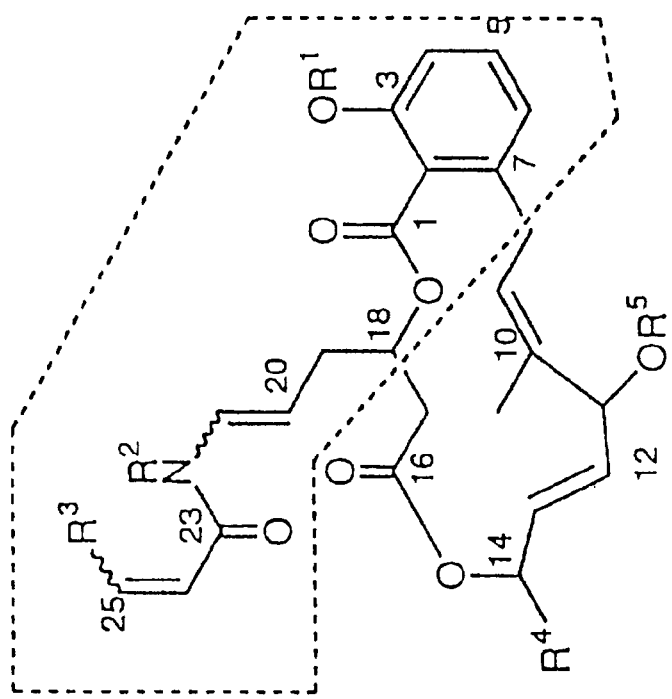
FIG. 2B LOBATAMIDES
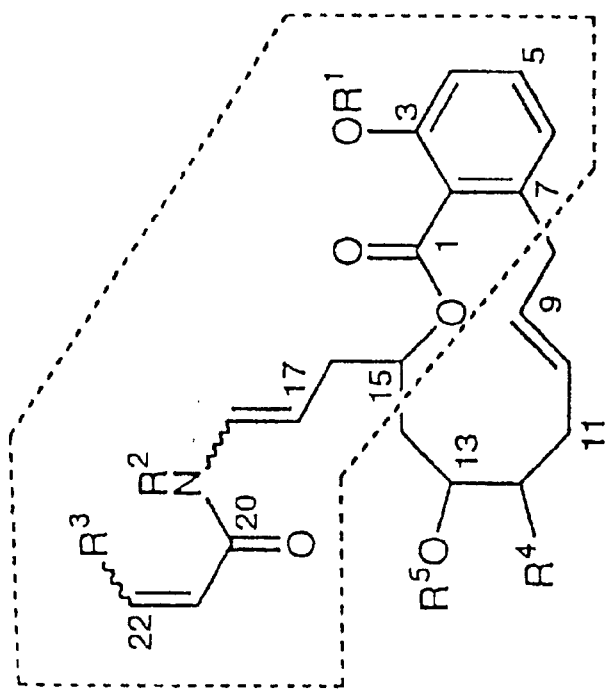
FIG. 2A SALICYLIHALAMIDES

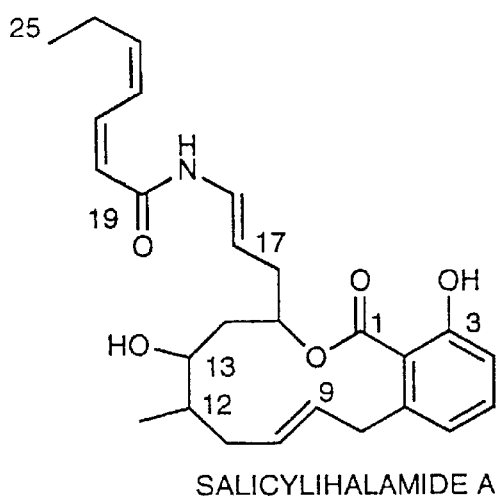
FIG. 3A SALICYLIHALAMIDE A
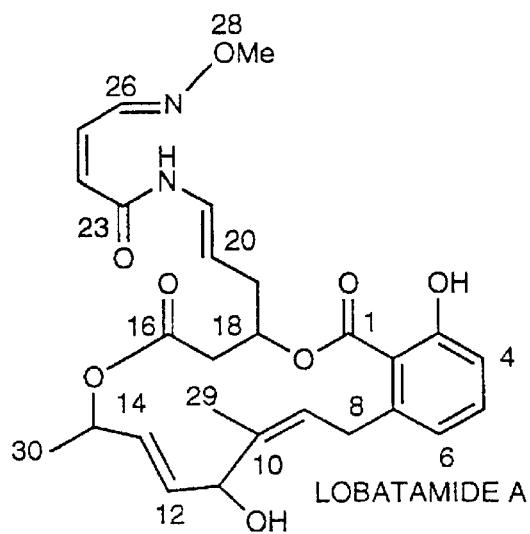
FIG. 3B LOBATAMIDE A
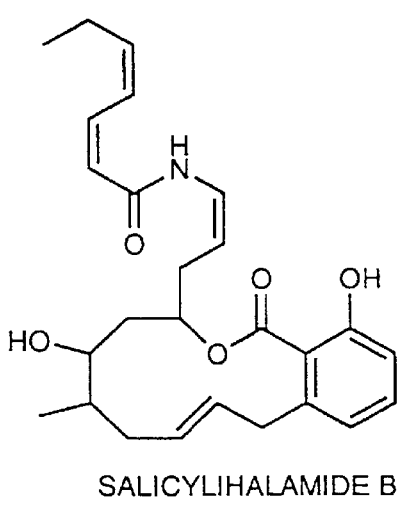
FIG. 3C SALICYLIHALAMIDE B
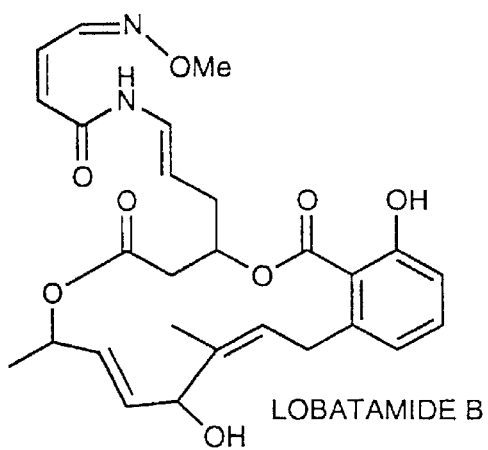
FIG. 3D LOBATAMIDE B

MACROCYCLIC LACTONES, COMPOSITIONS, AND METHODS OF USE

CROSS REFERENCE TO RELATED APPLICATIONS

This application is a U.S. national phase of International patent application PCT/US98/15011, which was filed Jul. 23, 1998, and claims priority under U.S.C. § 119(e) to U.S. Provisional patent application No. 60/053,784 which was filed Jul. 25, 1997, and has since lapsed.

TECHNICAL FIELD

The present invention relates to macrocyclic lactones, compositions, and methods of use.

BACKGROUND OF THE INVENTION

Biological metabolites are the subject of ongoing structural characterization in the identification of new, structurally interesting, naturally occurring organic molecules, often with undetermined uses. Recently, biological metabolites have become an important area of intense focus in the search for new medicinal leads with potential applicability in a broad range of therapeutic indications including, for example, anti-infective and anti-cancer therapy. One particularly vast source of potential medicinally relevant metabolites are marine organisms. For example, sponges of the genus Haliclona (class Demospongiae, order Haplosclerida, family Haliclonidae) have been reported to produce a variety of secondary metabolites. Especially notable has been the production of alkaloids such as the polymeric halitoxin, the antitumor betacarbolines manzamine A, B and C, pupauamine and haliclonadiamine, antimicrobial and antifungal pentacyclic alkaloids, haliclamines A and B, and halicyclamine A, a tetracyclic diamine alkaloid. See Faulkner, *J. Nat. Prod. Rep.*, 10, 497–539 (1993), and references cited therein; Parameswaran et al., *Oceanogr. Indian Ocean*, 417–420 (1992); Jaspars et al., *J. Org. Chem.*, 59, 3253–3255 (1994); Venkateswarlu et al., *J. Nat. Prod.*, 57, 1283–1285 (1994); Kobayashi et al., *Tetrahedron*, 51, 3727–3736 (1995); Zeng et al., *Zhongguo Haiyang Yaowu*, 14, 5–7 (1995) (*Chem. Abstr.*, 123, 193621 (1995)); Shen et al., *Chin. Pharm. J.* (Taipei), 48, 1–10 (1996) (*Chem. Abstr.*, 125, 82280 (1996)); and Charan et al., *Tetrahedron*, 52, 9111–9120 (1996). In addition, non-nitrogenous compounds, including tetrahydropyrans, alkylresorcinols, a tetrahydropyrone, sesquiterpenoid quinols, and enol sulfates have been found in Haliclona. However, none of these nonalkaloidal metabolites have been shown to have anticancer or cytotoxic activity.

Macrocyclic lactones are included among the classes of compounds identified from biological sources. For example, relatively simple fungal-derived orsellinic acid macrolides, lasiodiplodin (Aldridge et al., *J. Chem. Soc.* (C), 1623–1627 (1971)), which contain a 12-membered benzolactone ring with a methyl substituent at the ester methine, have been identified. Other relatively simple macrolides such as, for example, the 14-membered ring macrolide disclosed in Urry et al., *Tetrahedron Lett.*, 3109–3114 (1966), have been identified. Some arguably more complex macrolides of biological origin have been reported to possess an enamine formamide residue, which residue can be found in the ulapualide-kabiramide-halichondramide-mycalolide-jaspisamide, and tolytoxin(scytophycin)-sphinxolide classes of macrolides. See Roesener and Scheuer, *J. Am. Chem. Soc.*, 108, 846–847 (1986); Matsunaga et al., *J. Am. Chem. Soc.*, 108, 847–849 (1986); Kernan and Faulkner, *Tetrahedron Lett.*, 28, 2809–2812 (1987); Kernan et al., *J. Org. Chem.*, 53, 5014–5020 (1988); Fusetani et al., *Tetrahedron Lett.*, 30, 2809–2812 (1989); Rashid et al., *J. Nat. Prod.*, 58, 1120–1125 (1995); Kobayashi et al., *J. Nat. Prod.*, 56, 787–791 (1993); Carmeli et al., *J. Nat. Prod.*, 53, 1533–1542 (1990); and D'Auria et al., *Tetrahedron*, 49, 8657–8664 (1993).

Numerous compounds have been isolated from tunicates of the genus Aplidium. Examples of metabolites previously reported include prenylated quinones from Aplidium sp., *A. californicum*, *A. costellatum*, and *A. antillense*. See Fenical, In: *Food-Drugs from the Sea*, Proceedings, 4th (Webber and Ruggieri, eds.), Marine Technology Society, 1974, pp. 388–394; Guella et al., *J. Nat. Prod.*, 50, 621–626 (1987); Howard et al., *Tetrahedron Lett.*, 4449–4452 (1979); Targett and Keeran, *J. Nat. Prod.*, 47, 556–557 (1984); Benslimane et al., *J. Nat. Prod.*, 51, 582–583 (1988)]; Fu et al., *J. Am. Chem. Soc.*, 116, 12125–12126 (1994) (dimeric prenylated quinones from *Aplidium longithorax*); Carter and Rinehart, *J. Am. Chem. Soc.*, 100, 7441–7442 (1978) (a sphingosine derivative from an Aplidium sp.); Arabshashi and Schmitz, *Tetrahedron*, 29, 1099–1102 (1988) (thiazole and imidazole metabolites from *A. placiferum*); Copp et al., *Tetrahedron Lett.*, 30, 3703–3706 (1989) (1,2,3-trithiane derivatives from an Aplidium sp.); Kobayashi et al., *J. Org. Chem.*, 59, 255–257 (1994) (alkaloids from an Aplidium sp. and *A. pantherinium*); Doi et al., Tetrahedron, 50, 8651–8656 (1994) (alkaloids from an Aplidium sp. and *A. pantherinium*); Carroll et al., *Aust. J. Chem.*, 46, 825–832 (1993) (nucleosides from *A. multiplicatum*); Kim et al., *J. Nat. Prod.*, 56, 1813–1816 (1993) (nucleosides from *A. multiplicatum*); and Rochfort et al., *Aust. J. Chem.*, 49, 1217–1219 (1996) (chromenols from *A. solidum*).

Murray et al., *Aust. J. Chem.*, 48, 1253–1266 (1995), discloses the isolation of aplidites A–G from an Aplidium sp.; however, there was no indication of biological activity of any kind, and subsequent investigations revealed that the structural assignment of the aplidites in Murray et al. (supra) may have been in error.

Among the numerous challenges faced by medicinal chemistry research, one of the most perplexing problems remains identifying new leads applicable in the chemotherapeutic treatment of cancers. Purely synthetic approaches toward the identification of novel anticancer agents are typically unsuccessful, partly due to the technological and human limitations inherent in laboratory synthesis. Although biological metabolites provide a vast resource of new structurally diverse chemical compounds, some of which have demonstrated biological activity, the therapeutic options for individuals suffering from cancer are tragically few.

Thus, there remains a need for anticancer compounds, pharmaceutical compositions, and methods of treating cancer. The present invention provides such compounds, compositions, and methods. These and other advantages of the present invention, as well as additional inventive features, will be apparent from the description of the invention provided herein.

BRIEF SUMMARY OF THE INVENTION

The present invention provides a compound of the formula:

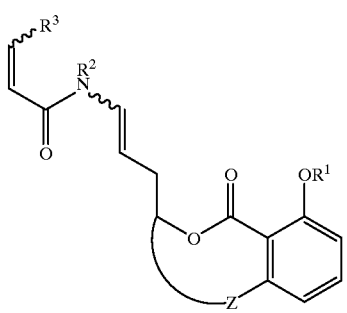

(I)

wherein $R^1$ and $R^2$ are the same or different and are independently H, $C_1$–$C_6$ straight-chain or branched-chain saturated or unsaturated alkyl, aryl, $R^6CH_2$—, $R^6CO$—, or $R^6SO_2$—, wherein $R^6$ is H, $C_1$–$C_6$ straight-chain or branched-chain saturated or unsaturated alkyl, or aryl; $R^3$ is H, $C_1$–$C_6$ straight-chain or branched-chain saturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms (including heteroatoms) which atoms, together with the five atoms beginning with the carbon of the aromatic ring in meta-relationship with $OR^1$ and ending with the carbon directly attached to the alkyl oxygen of the lactone, which carbons are covalently bonded to either end of linker Z, integrally form a 12–15 membered ring; or a pharmaceutically acceptable salt, an ester, or a prodrug thereof.

The present invention also provides a composition which comprises a therapeutically effective amount of at least one compound of the present invention and a pharmaceutically acceptable carrier.

The present invention further provides a method of preventing or treating cancer which comprises administering to a patient in need thereof an anticancer effective amount of at least one compound of the present invention.

BRIEF DESCRIPTION OF THE DRAWINGS

FIG. 2 illustrates two preferred generic embodiments of the compounds of the present invention: salicylihalamides (FIG. 2A) and lobatamides (FIG. 2B).

DETAILED DESCRIPTION OF THE INVENTION

The present invention provides a compound of the formula:

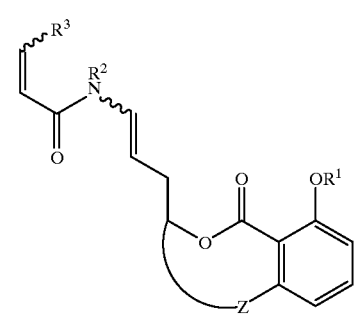

Figure 1:
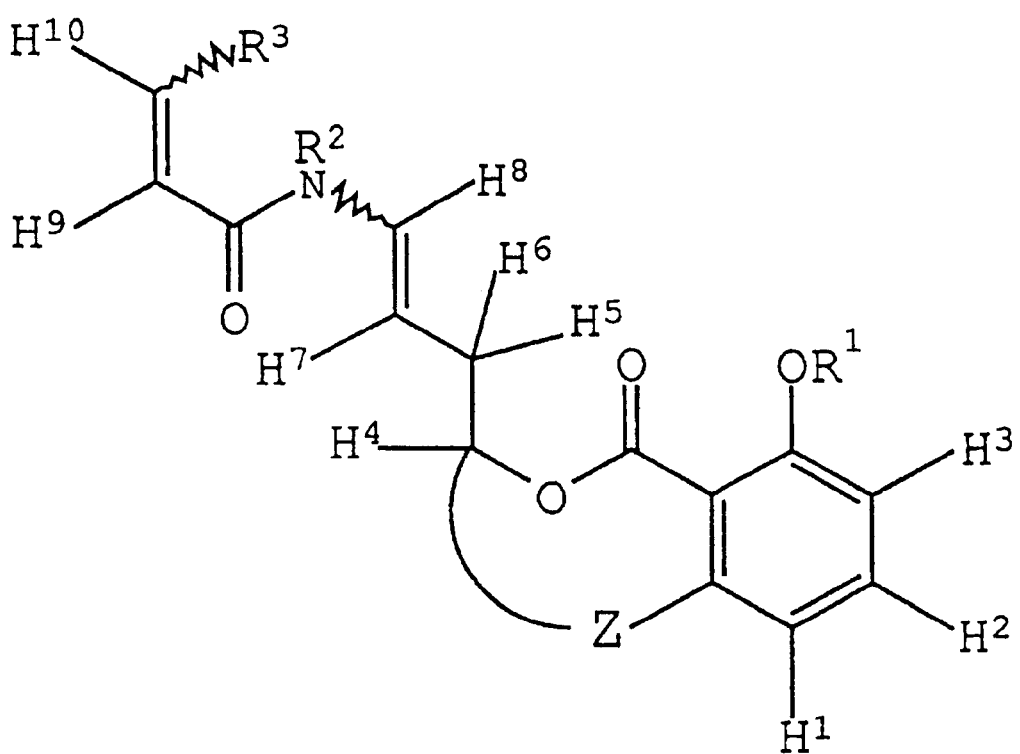
FIG. 1 is a generic representation of the compounds of the present invention.

(I)

wherein $R^1$ and $R^2$ are the same or different and are independently H, $C_1$–$C_6$ straight-chain or branched-chain saturated or unsaturated alkyl, aryl, $R^6CH_2$—, $R^6CO$—, or $R^6SO_2$—, wherein $R^6$ is H, $C_1$–$C_6$ straight-chain or branched-chain saturated or unsaturated alkyl, or aryl; $R^3$ is H, $C_1$–$C_6$ straight-chain or branched-chain saturated or unsaturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms (including heteroatoms) which atoms, together with the five atoms beginning with the carbon of the aromatic ring in meta-relationship with $OR^1$ and ending with the carbon directly attached to the alkyl oxygen of the lactone, which carbons are covalently bonded to either end of linker Z, integrally form a 12–15 membered ring; or a pharmaceutically acceptable salt, an ester, or a prodrug thereof. A more detailed generic representation of the compounds of the present invention is illustrated in FIG. 1.

In a preferred embodiment, the present invention is directed to a compound selected from the group consisting of:

(IA)

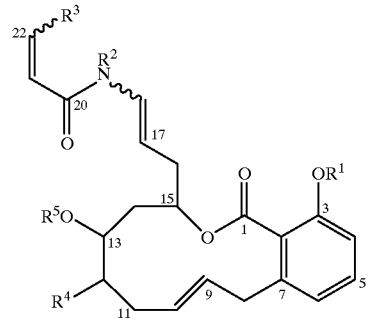

and (IB)

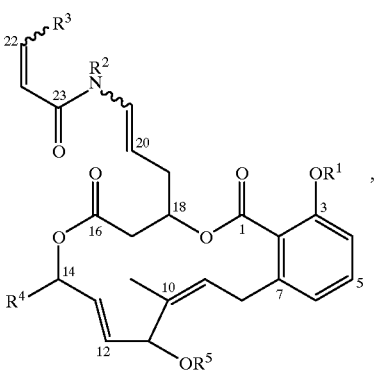

wherein $R^1$, $R^2$, and $R^5$ are the same or different and are independently H, $C_1$–$C_6$ straight-chain or branched-chain saturated or unsaturated alkyl, aryl, $R^6CH_2$—, R6CO—, or $R^6SO_2$—, wherein $R^6$ may be H, $C_1$–$C_6$ straight-chain or branched-chain saturated or unsaturated alkyl, or aryl; $R^3$ is H, $C_1$–$C_6$ straight-chain or branched-chain saturated or unsaturated alkyl, aryl, an oxime, or an oxime methyl ether; $R^4$ is H, $C_1$–$C_6$ alkyl, or $R^7CH_2$—, wherein $R^7$ is $R^6O$—, $R^6CO_2$—, or $R^6SO_3$—; and at least one aromatic ring position is optionally substituted with a substituent selected from the group consisting of halo, nitro, amino, hydroxyl, thio, acyl, $C_1$–$C_6$ alkyl, or cyano; pharmaceutically acceptable salts, esters, and prodrugs thereof. Compounds of Formula (IA) and Formula (IB) of the present invention are given the trivial names salicylihalamides and lobatamides, and are further illustrated in FIG. 2A and FIG. 2B, respectively. Also highlighted in FIGS. 2A and 2B (by the regions encompassed by the dotted lines) is the structural component motif shared by all compounds of the present invention.

In a further preferred embodiment, the present invention provides a compound selected from the group consisting of:

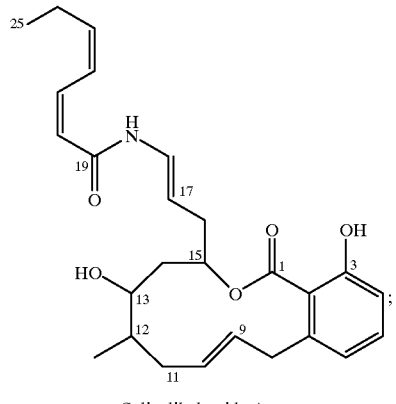

Salicylihalamide A;

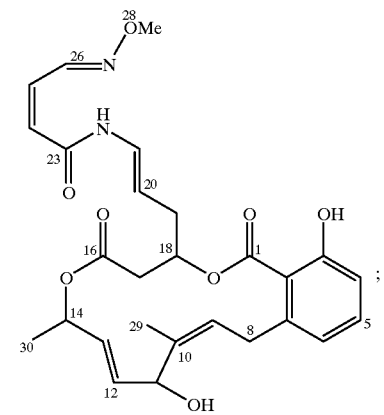

Lobatamide A

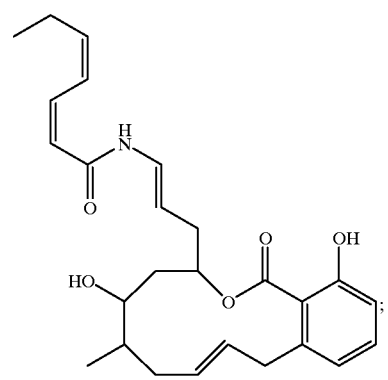

Salicylihalamide B

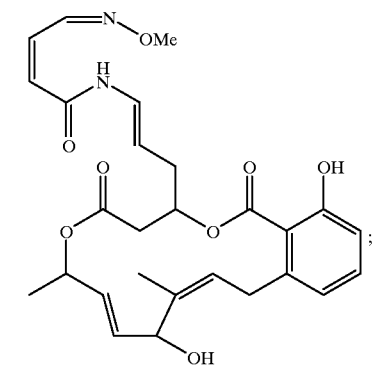

Lobatamide B

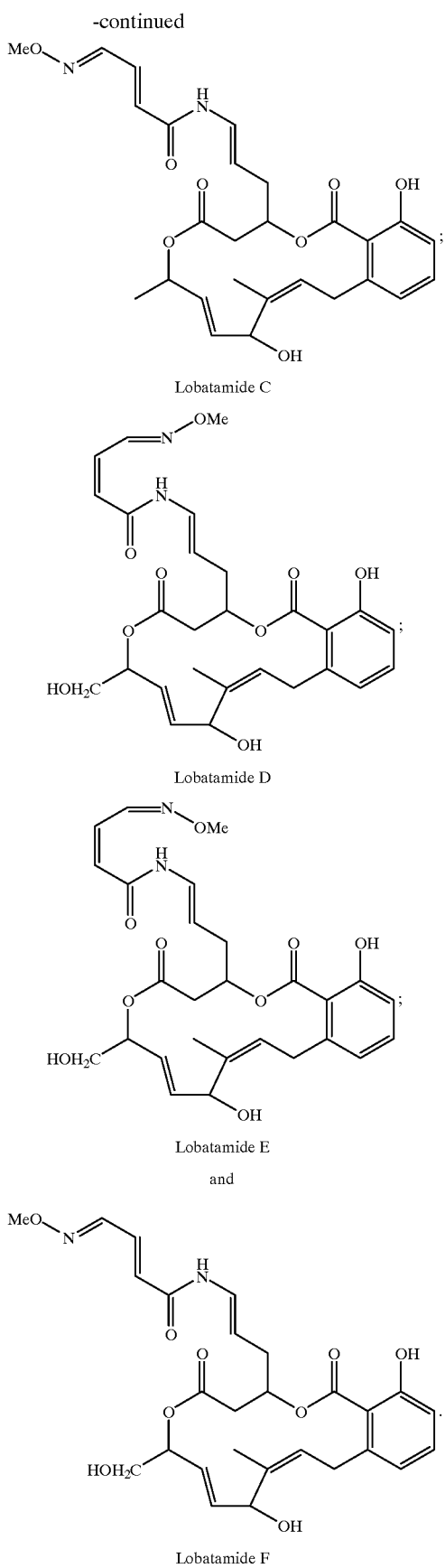

Lobatamide C

Lobatamide D

Lobatamide E and

Lobatamide F

Figure 3E:
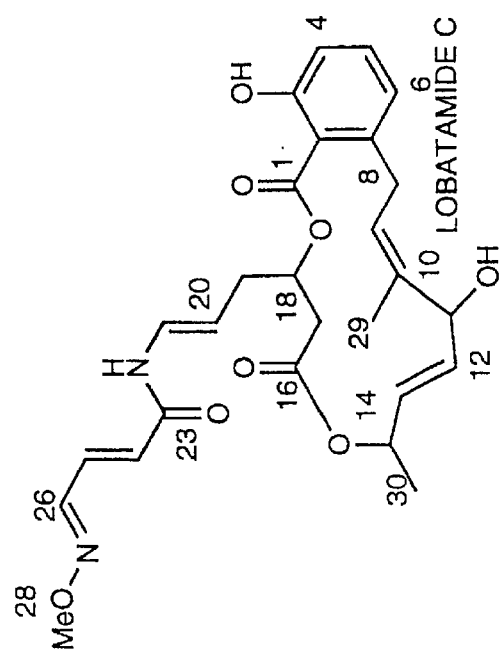
FIG. 3 illustrates the structures of exemplary compounds of the present invention: salicylihalamide A (FIG. 3A), salicylihalamide B (FIG. 3C), lobatamide A (FIG. 3B), lobatamide B (FIG. 3D), lobatamide C (FIG. 3E), lobatamide D (FIG. 3F), lobatamide E (FIG. 3G) and lobatamide F (FIG. 3H).
Figure 3F:
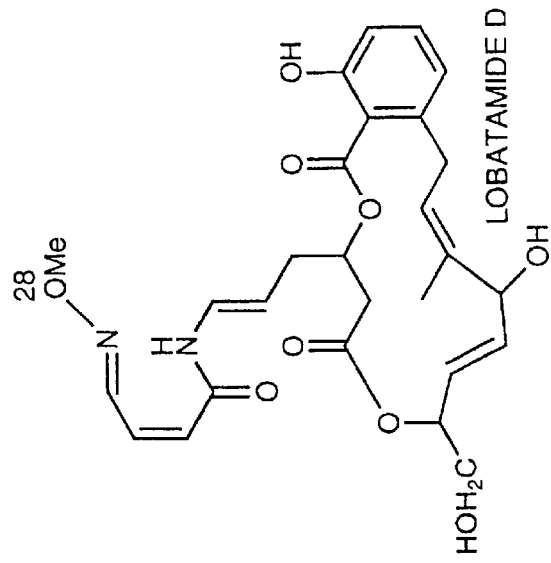
Figure 3H:
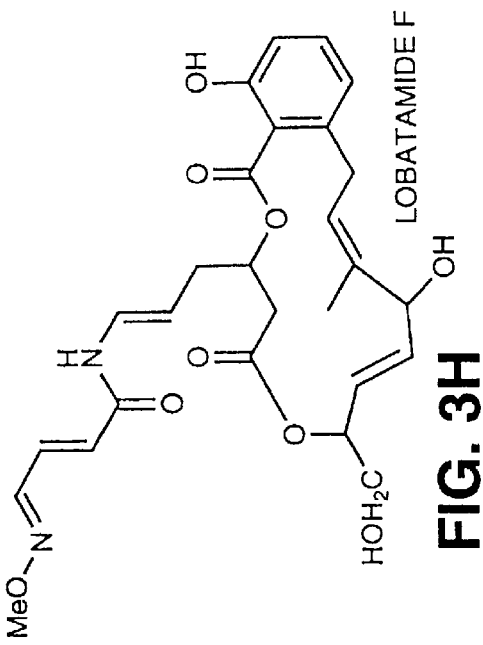
Figure 3G:
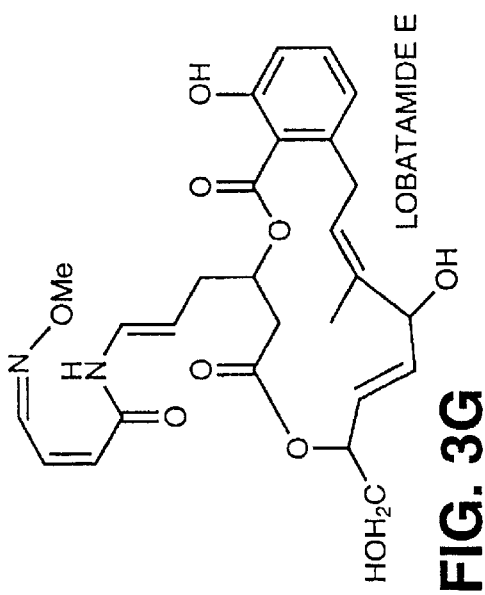
Figure 4:
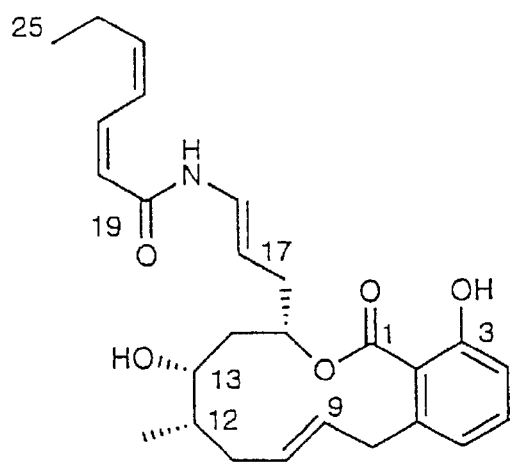
FIG. 4 illustrates the absolute stereochemistry of salicylihalamide A.

FIGS. 3A and 3B further illustrate salicylihalamides A and B and lobatamides A–F. The structure and absolute stereochemistry of salicylihalamide A are illustrated in FIG. 4.

The present invention further provides a composition comprising a compound of the present invention, e.g., a therapeutically effective amount of at least one anticancer compound of the present invention (e.g., an antitumor effective amount), optionally in combination with at least one anticancer compound other than a compound of the present invention, and a carrier, e.g., a pharmaceutically acceptable carrier. Suitable carriers for use in the present invention include, but are not limited to, injectable or orally or rectally administratable oils, lipid emulsions, aqueous solutions or suspensions, or, in the case of orally or rectally administratable tablets or capsules, a pharmacologically inert excipient.

The compounds and compositions of the present invention kill or inhibit the growth of human cancer, both leukemic and solid tumor cancers, more particularly solid tumors, and most particularly tumors of the lung, brain, kidney, and breast, and melanomas.

The anticancer compounds of the present invention, or anticancer derivatives thereof, can be made into pharmaceutical compositions by combination with appropriate, pharmaceutically acceptable carriers, and can be formulated into preparations in solid, semi-solid, liquid, or gaseous forms such as tablets, capsules, powders, granules, ointments, solutions, suppositories, injections, inhalants, and aerosols in the usual ways for their respective route of administration. In pharmaceutical dosage forms, a compound employed in the present invention can be used alone or in appropriate association, as well as in combination, with other pharmaceutically active compounds, including other anticancer compounds, as described herein.

The following methods and carriers are merely exemplary and are in no way limiting. In the case of oral preparations, the compound of the present invention can be used alone, or in combination with at least one anticancer agent other than a compound of the present invention, together with appropriate additives to make tablets, powders, granules, or capsules, e.g., with conventional additives such as lactose, mannitol, corn starch or potato starch; with binders such as crystalline cellulose, cellulose derivatives, acacia, corn starch, or gelatins; with disintegrators such as corn starch, potato starch or sodium carboxymethylcellulose; with lubricants such as talc or magnesium stearate; and, if desired, with diluents, buffering agents, moistening agents, preservatives, and flavoring agents.

A compound of the present invention, alone or in combination with at least one anticancer agent other than a compound of the present invention, can be formulated into preparations for injection by dissolution, suspension, or emulsification in an aqueous or nonaqueous solvent, such as vegetable oil, synthetic aliphatic acid glycerides, esters of higher aliphatic acids, or propylene glycol (if desired, with conventional additives such as solubilizers, isotonic agents, suspending agents, emulsifying agents, stabilizers, and preservatives).

The composition of the present invention can be made into an aerosol formulation to be administered via inhalation. Such aerosol formulations can be placed into pressurized acceptable propellants such as dichlorodifluoromethane, propane, nitrogen, and the like.

Furthermore, the composition of the present invention, alone or in combination with at least one additional anticancer agent other than a compound of the present invention, can be made into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature, but are solid at room temperature.

Unit dosage forms for oral or rectal administration such as syrups, elixirs, and suspensions can be provided wherein each dosage unit, e.g., teaspoonful, tablespoonful, tablet, or suppository contains a predetermined amount of the composition containing the compound of the present invention, alone or in combination with other anticancer agents. Similarly, unit dosage forms for injection or intravenous administration can comprise a composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of a compound or compounds of the present invention, alone or in combination with other anticancer agent(s), calculated in an amount sufficient to produce the desired effect in association with a pharmaceutically acceptable carrier. The specifications for the unit dosage forms of the present invention depend on the particular effect to be achieved, and the particular pharmacodynamics associated with the compound(s) in the individual host.

In the composition of the present invention, the pharmaceutically acceptable carrier, for example, vehicles, adjuvants, excipients, or diluents, are accessible to those of skill in the art and are typically available commercially.

One skilled in the art can easily determine the appropriate method of administration for the exact formulation of the composition being used. Any necessary adjustments in dose can be made readily to meet the nature or severity of the cancer, and the individual patient's overall physical health, and adjusted accordingly by the skilled practitioner.

The present invention further provides a method of treating cancer comprising administering to a patient an "anticancer effective amount" (e.g., an antitumor effective amount) of at least one compound or composition of the present invention, optionally in combination with an anticancer effective amount of at least one additional anticancer compound other than a compound of the present invention. The compound or composition can be administered, for example, orally, intramuscularly, subcutaneously, or intravenously. The composition can be present as a solution suitable, for example, for intravenous injection or infusion.

The composition also can be present in unit dosage form, such as, for example, a tablet or capsule. The "anticancer effective amount" is the dose necessary to achieve an "effective level" of the active compound in the individual patient. The "anticancer effective amount" can be defined, for example, as that amount required to be administered to an individual patient to achieve an anticancer effective blood and/or tissue level of a compound of the present invention to kill or inhibit the growth of the cancer; the effective blood level might be chosen, for example, as that level (e.g., $10^{-11}$–$10^{-7}$ M from Example 4) to kill or inhibit the growth of tumor cells in a screening assay. Since the "effective level" is used as the preferred endpoint for dosing, the actual dose and schedule can vary, depending upon interindividual differences in pharmacokinetics, drug distribution, and metabolism. The "effective level" can be defined, for example, as the blood or tissue level desired in the patient that corresponds to a concentration of a compound of the present invention which kills or inhibits the growth of human cancers in an assay which can predict for clinical anticancer activity of chemical compounds. The "effective level" for compounds of the present invention can vary when these compounds are used in combination with other anticancer compounds or combinations thereof.

Alternatively, the "effective level" can be defined, for example, as that concentration of the compound of the present invention needed to inhibit markers of the cancer in the patient's blood, or which slows or stops the growth of the patient's cancer, or which causes the patient's cancer to regress or disappear, or which renders the patient asymptomatic to the particular cancer, or which renders an improvement in the patient's subjective sense of condition. Since a fixed "anticancer effective amount" is used as the preferred endpoint for dosing, the actual dose and schedule for drug administration for each patient can vary depending upon interindividual differences in pharmacokinetics, drug disposition, and metabolism. Moreover, the dose can vary when the compound is used in combination with other drugs.

One skilled in the art can easily determine the appropriate dose, schedule, and method of administration for the exact formulation of the composition being used, in order to achieve the desired effective level in the individual patient. One skilled in the art also can readily determine and use an appropriate indicator of the effective level of the compounds of the present invention by a direct (e.g., analytical chemistry) and/or indirect (e.g., with clinical chemistry indicators) analysis of appropriate patient samples (e.g., blood and/or tissues), or by direct or indirect observations of the shrinkage or inhibition of growth of the individual patient's tumor. There are many references in the art that teach how one works out the protocols of administering anticancer agents to patients (see, e.g., "Cancer Chemotherapy: Principles and Practice" ed., Chabner and Collins, J. B. Lippincott, 1990, especially chapter 2, by J. B. Collins).

The present method of treating cancer using the compounds of the present invention can be made more effective by administering other anticancer compounds along with the compound of the present invention. These other anticancer compounds include, but are not limited to, all of the known anticancer compounds approved for marketing in the United States and those that will become approved in the future. See, for example, Table 1 and Table 2 of Boyd "The Future of Drug Development", *Current Therapy in Oncology*, Section I. Introduction to Cancer Therapy (J. E. Niederhuber, ed.), Chapter 2, by B. C. Decker, Inc., Philadelphia, 1993, pp. 11–22. More particularly, these other anticancer compounds include doxorubicin, bleomycin, vincristine, vinblastine, VP-16, VW-26, cisplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

The compounds of the present invention can be obtained by one skilled in the art by chemical synthesis using well-known and readily available chemical reactions, reagents, and procedures. It will also be appreciated by one skilled in the art that compounds of the present invention, including anticancer derivatives, salts, esters, and prodrugs thereof, may be obtained by chemical modification(s) of synthetic or naturally occurring compounds of the present invention, using well-known and readily available reactions, reagents, and procedures.

For example, some of the work underlying the present invention now appears in the scientific literature (Galinis et al., *J. Org. Chem.*, 62: 8968–8969 (1997); and Erickson et al., *J. Org. Chem.*, 62, 8188–8192 (1997)). Other parties have subsequently published related matter. Suzumure et al., *Tetrahedron Lett.*, 43, 7573–7576 (1997), published Oct. 27, 1997, described the isolation and structure elucidation of a compound named YM-75518, which has the same structure as that of lobatamide A, a compound of the present invention. The compound disclosed in Suzumure, et al. (supra) was isolated and characterized from the fermentation broth of a Pseudomonas sp. bacterium, and was reported to have some weak antifungal activity; however, no anticancer, cytotoxic or other biological activity, nor potential uses, were described. Others appear to have erroneously assigned structures to compounds having the same properties as some lobatamides of the present invention. For example, it appears that the compounds disclosed in Murray et al.,*Aust. J. Chem.*, 48, 1253–1266 (1995), named aplidites A–D, are the same compounds as lobatamides A, B, D, and E of the present invention, even though the reported structures are very different. However, as noted above, Murray et al. (supra) does not disclose any biological activity of any kind for these compounds.

The unique anticancer activity of the compounds of the present invention can be demonstrated in the U.S. National Cancer Institute's 60 cell-line, human tumor, disease-oriented screen, which accurately predicts anticancer activity of chemical compounds against human cancers. For reviews pertinent to the NCI 60 cell-line screen, see Boyd, In: *Current Therapy in Oncology* (Niederhuber, ed.), Philadelphia: B. C. Decker, Inc., 1993, pp. 11–22; Boyd and Paull, *Drug Dev. Res.*, 34, 91–109 (1995); Grever and Chabner, In: *Cancer Principles and Practice of Oncology*, 5th Ed. (DeVita et al., eds.), Philadelphia: Lippincott-Raven, 1977, pp. 385–394; Paull et al., In: *Cancer Chemotherapeutic Agents* (Foye, ed.), Washington, D.C.: American Chemical Society Books, 1995, pp. 9–45; and Weinstein et al., *Science*, 275, 343–349 (1997). The characteristic screening "fingerprints" of the compounds of the present invention in the NCI screen are unlike those of any known conventional anticancer agent, indicating that the mechanism of their anticancer activity is unprecedented.

The NCI 60 cell-line human tumor screen measures the ability of a compound to selectively kill or inhibit the growth of diverse human cancers. More specifically, using this screen, it can be shown that the compounds of the present invention are highly active against certain types of human solid tumors (e.g., non-small cell lung cancer, renal cancer, and melanoma) which are very resistant or completely resistant to existing anticancer drugs, and it can be shown that the compounds also are active against many other examples of human solid tumors and leukemia cancer cells. By these observations, and with other detailed analyses of the characteristic tumor cellular response profile produced by the compounds of the present invention in the aforementioned screen, it can be shown that the compounds of the present invention are novel anticancer agents with an unprecedented anticancer bioactivity profile for the treatment of human solid tumors. It is particularly noteworthy for a compound to be as active or more active against human solid tumor cell lines as against human leukemia cell lines. The compounds of the present invention are thus shown to be new and broadly efficacious anticancer agents. The compounds inhibit or destroy human leukemias, lymphomas, and solid tumors. Solid tumors may include lung cancer, colon cancer, brain cancer, melanoma, ovarian cancer, renal cancer, head and neck cancer, testicular cancer, germ-line cancers, endocrine tumors, uterine cancer, breast cancer, sarcomas, gastric cancer, hepatic cancer, esophageal cancer, and pancreatic cancer.

The U.S. National Cancer Institute (NCI)'s 60 cell-line human tumor primary screen not only provides the means to demonstrate the novel and characteristic anticancer profile of synthetic, semisynthetic, and naturally occurring compounds of the present invention, but also a means by which to identify natural sources of compounds of the present invention. The NCI screen was designed and implemented during 1985–1990 under the direction, close scrutiny, and supervision of several internationally comprised and renowned extramural (non-NCI) advisory and review groups, including the NCI Division of Cancer Treatment's Board of Scientific Counselors, an Ad Hoc Expert Review-Committee thereof, the National Cancer Advisory Board, and the President's Cancer Panel (see Boyd, In: *Anticancer Drug Development Guide: Preclinical Screening, Clinical Trials, and Approval* (Teicher, B. A., ed.), Totowa, N.J.: Humana Press, Inc., pp. 23–42, 1997). The impetus for development of the NCI screen was the international recognition that most of the commercially available anticancer drugs worldwide are essentially inactive or only transiently active against most forms of human cancer. Reviews are disclosed, for example, in Boyd, In: *Cancer: Principles and Practice of Oncology Updates*(DeVita, V. T., Jr., et al., eds), Philadelphia: Lippincott, 1989, pp. 11–22; and Boyd, In: *Current Therapy in Oncology*(Niederhuber, J. E., ed.), Philadelphia: BC Decker, 1993, pp. 11–22. As a group, the leukemias and lymphomas are typically the most sensitive to available drugs, while most human solid tumors (e.g., the world's most common tumor types, such as tumors of the lung, colon, breast, prostate, stomach, and liver) are either totally resistant or highly resistant to available anticancer drugs.

The need for new classes of anticancer drugs remains an urgent worldwide priority, that is being addressed effectively through new research and development applications of the NCI 60 cell-line screen. Reviews can be found, for example, in Boyd and Paull, *Drug Dev. Res.*, 34, 91–109 (1995); Weinstein et al., *Science*, 275, 343–349 (1997); and Grever and Chabner, In: *Cancer: Principles and Practice of Oncology*, 5th Ed. (DeVita, V. T., et al., eds.), Philadelphia: Lippincott-Raven, 1977, pp. 385–394. Although this NCI screen has been operational only since 1990, it has already led to the discovery, development, and clinical use of significant new anticancer drugs in human cancer patients. The NCI screen provides an unprecedentedly rich information content to support the identification of important new classes of anticancer drugs. For example, see Weinstein et al., *Science*, 275, 343–349 (1997); Grever and Chabner, In: *Cancer: Principles and Practice of Oncology*, 5th Ed. (DeVita, V. T., et al., eds.), Philadelphia: Lippincott-Raven, 1977, pp. 385–394; and Sausville, In: *Anticancer Drug Development Guide: Preclinical Screening, Clinical Trials, and Approval* (Teicher, B. A., ed.), Totowa, N.J.: Humana Press, Inc., 1997, pp. 217–226.

The NCI screen consists of a panel of 60 different human tumor cell lines against which compounds are tested over a defined range of concentrations to determine the relative degree of growth inhibition or cytotoxicity against each cell line. The design and operation of the screen is such that for each compound tested, both the absolute and relative sensitivities of individual cell lines comprising the screen are sufficiently reproducible that a characteristic profile or "fingerprint" of cellular response is generated. Compounds which are active in the NCI screen show pronounced differential tumor growth-inhibitory and/or cytotoxic effects to the diverse cell lines comprising the 60 cell-line panel. The degree of differential response between the most and least sensitive lines typically may be relatively small (e.g., 2- to 10-fold), or occasionally as great as 3–4 orders of magnitude. Furthermore, the cell lines may be widely heterogeneous in response to a given compound, or they may be comparatively homogeneous, with only a relatively few lines showing much greater or lesser sensitivity than average. Regardless of the magnitude of the differential or the degree of heterogeneity of response of the cell line panel, it is the reproducibility of the response fingerprint that is important to the useful information contained therein.

Detailed disclosures of the screening assay are published, for example, in Monks et al., *J. Natl. Cancer Inst.*, 83, 757–766 (1991); Skehan et al., *J. Natl. Cancer Inst.*, 82, 1107–1112 (1990); and Boyd and Paull, *Drug Dev. Res.*, 34, 484–488 (1995). The identities, sources, derivation, morphological, and immunocytochemical characteristics, and methods of maintenance of the cell lines comprising the NCI 60 cell line panel, have been described in detail, for example, in Boyd, In: *Cancer: Principles and Practice of Oncology Updates* (DeVita, V. T., Jr., et al., eds), Philadelphia: Lippincott, 1989, pp. 1–12; Monks et al., *J. Natl. Cancer Inst.*, 83, 757–766 (1991); Stinson et al., *Anticancer Res.*, 12, 1034–1035 (1992); and Boyd and Paull, *Drug. Dev. Res.*, 34, 91–109 (1995).

In the screening assay, each agent is tested over a broad concentration range against every cell line in the panel. All lines are inoculated onto a series of standard 96-well microtitre plates on day zero, followed by a 24 h incubation in the absence of the test compound. The inoculation densities employed depend upon the particular cell line and its growth characteristics. Inoculation densities used are as published in Monks, A. et al., *J. Natl. Cancer Inst.*, 83, 757–766 (1991); and Boyd and Paull, *Drug Dev. Res.*, 34, 91–109 (1995). Test compounds are evaluated at five 10-fold dilutions. Following a 48-hour incubation with the test compound, the cells are assayed by the sulforhodamine B procedure as described in Skehan et al., *J. Natl. Cancer Inst.*, 82, 1107–1112 (1990); Monks et al., *J. Natl. Cancer Inst.*, 83, 757–766 (1991); Rubinstein et al., *J. Natl. Cancer Inst.*, 82, 1113–1118 (1990). Optical densities are measured on automated plate readers, followed by computerized data acquisition, processing, storage, and availability for display and analysis.

Each successful test of a compound generates 60 dose-response curves (see, e.g., Example 4) which are printed in the NCI screening data report as a series of composites comprising the tumor-type subpanels. Data for any individual cell line(s) failing quality control criteria, or otherwise deficient for any cell line(s) not tested successfully, are eliminated from further analysis and are deleted from the screening report.

The "percentage growth" (PG) term, and meaning of the +50, 0, and −50 response reference lines, the calculated response parameters, $GI_{50}$, TGI, and $LC_{50}$, construction and use of "mean-graphs" and the COMPARE pattern-recognition algorithms, which are all defined or provided in detail in Boyd et al., In: *Cytotoxic Anticancer Drugs: Models and Concepts for Drug Discovery and Development* (Valeriote, F. A., et al., eds.), Amsterdam: Kluwer Academic Publishers, 1992, pp. 11–34; Monks et al., *J. Natl. Cancer Inst.*, 83, 757–766 (1991); and Boyd and Paull, *Drug Dev. Res.*, 34, 91–109 (1995), are briefly reviewed as follows, with particular pertinence to the present invention.

The 50% growth inhibition parameter ($GI_{50}$) is the concentration of test drug where $100 \times (T-T_o)/(C-T_o) = 50 = PG$. The optical density of the test well after the 48 hour drug exposure is T; the optical density at time zero is $T_o$; and the control optical density is C. The PG is a T/C-like parameter that can have values from +100 to −100. Whereas the $GI_{50}$ may be viewed as a growth-inhibitory level of effect, the TGI signifies a "total growth inhibition" or cytostatic level of effect. The TGI is the drug concentration where $100 \times (T-T_o)/(C-T) = 0 = PG$. The $LC_{50}$ is the lethal concentration, "net cell killing" or cytotoxicity parameter. It is the concentration where $100 \times (T-T_o)/T_o = -50 = PG$. The control optical density is not used in the calculation of $LC_{50}$.

A mean-graph is a pattern created by plotting positive and negative values, termed "deltas," generated from a set of $GI_{50}$, TGI, or $LC_{50}$ concentrations obtained for a given compound tested against each cell line in the NCI in vitro screen. The deltas are generated from the $GI_{50}$, TGI, or $LC_{50}$ data by a three-step calculation. For example, the $GI_{50}$ value for each cell line successfully tested against a given compound is converted to its $\log_{10} GI_{50}$ value. The mean panel $\log_{10} GI_{50}$ value is obtained by averaging the individual $\log_{10} GI_{50}$ values. Each $\log_{10} GI_{50}$ value then is subtracted from the panel mean to create the corresponding delta.

To construct the mean-graph, the deltas are plotted horizontally in reference to a vertical line that represents the calculated mean panel $GI_{50}$. The negative deltas are plotted to the right of the mean reference line, thereby proportionately representing cell lines more sensitive than the calculated average. Conversely, the positive deltas are plotted to the left of the reference line to represent the less sensitive cell lines to the given agent. Thus, for example, a bar projecting 3 units to the right of the vertical reference line in a $GI_{50}$ mean-graph indicates that the $GI_{50}$ concentration for that cell line is 1000 times less than the panel-averaged $GI_{50}$ concentration. The TGI and $LC_{50}$ mean-graphs are prepared and interpreted similarly.

Three additional numbers are printed at the base of each of the three respective mean-graphs. These numbers are the MG-MID, the Delta (not be confused with the "delta" for an individual cell line), and the Range. The MG-MID is the calculated mean panel $GI_{50}$, TGI, or $LC_{50}$. The Delta is the number of $\log_{10}$ units by which the delta of the most sensitive line(s) of the panel differ(s) from the corresponding MG-MID. Similarly, the Range is the number of $\log_{10}$ units by which the delta of the most sensitive line(s) of the panel differ(s) from the delta(s) of the least sensitive line(s).

COMPARE is a computerized, pattern-recognition algorithm which is used in the evaluation and exploitation of data generated by the NCI screen. In essence, COMPARE is a method of determining and expressing the degree of similarity, or lack thereof, of mean-graph profiles generated on the same or different compounds. An early impetus for the creation of such a tool during the development of the screen was the need to standardize and to establish and monitor the screen's consistency and reproducibility over time. This is accomplished by the regular testing of standard compounds which are expected to generate the same or very similar profiles when screened repetitively against the same panel of cell lines.

Further in the course of standardizing the screen, NCI selected as reference compounds approximately 170 agents for which a considerable amount of information was available about their preclinical and/or clinical anticancer properties and mechanism(s) of action. These compounds included commercially marketed anticancer drugs, investigational anticancer drugs, and other anticancer drugs which were or had been in preclinical development based upon activities in other cancer-related test systems. The repetitive periodic screening of these prototype "standard agents" (the cumulative compilation of results of which forms the "Standard Agents Database") remains the basis for calibration and standardization of the screen.

The NCI's Standard Agent Database also is the key to many useful new drug discovery applications of the NCI screen. For example, the characteristic response profile "fingerprint" of a selected standard agent may be used as the "seed" to probe any other available mean-graph database to see if there are any closely matching profiles contained therein. Conversely, a profile selected from any available mean-graph database can be used to probe the "Standard Agent Database" to determine whether or not there are any closely matching standard agent profiles. Additional databases used for such studies may be constructed or defined as desired and may be relatively small (e.g., comprising a single compound or a selected congeneric series of compounds) or very large (e.g., the entire databases from all pure compounds, mixtures, fractions, and extracts tested in the NCI screen to date).

Initial NCI studies with COMPARE led quickly to the observation that compounds matched by their mean-graph patterns often had related chemical structures. Closer examination of this phenomenon led further to the realization that compounds of either related or unrelated structures and matched by mean-graph patterns frequently shared the same or related biochemical mechanisms of action For example, see Boyd et al., In: *Current Therapy in Oncology* (Niederhuber, J. E., ed.), Philadelphia: B C Decker, 1993, pp. 11–22; and Paull et al., In: *Cancer Therapeutic Agents*, Washington, D.C.: Am. Chem. Soc. Books, 1995, pp. 9–45; and references cited therein.

COMPARE analyses can be performed using the mean-graph deltas calculated from either the $GI_{50}$'s, the TGI's, or the $LC_{50}$'s. When a selected particular mean-graph profile or "seed" is used to probe a given database, the appropriate delta value for each cell line is compared to the corresponding delta value for the same cell line for every mean-graph entry in the specified database set. If either delta value is missing for any cell line (e.g., due to test failure or quality control deletion), then that cell line is eliminated entirely from the calculation for that particular seed/mean-graph and database/mean-graph pair. Thus, for each mean-graph in the specified database, a set of pairs (maximum of 60) of delta values is obtained. The commercially available SAS statistical program is used to calculate a Pearson product moment correlation coefficient (0.0–1.0) for each set of delta value pairs. Then the mean-graphs of all compounds in the specified database can be rank-ordered for similarity to the seed mean-graph. Public access to the NCI's "Standard Agents Database" as well as to a variety of NCI screening data display and analysis tools, including COMPARE, are available to investigators worldwide via the Internet (http://epnwsl.ncifcrf.gov:2345/dis3d/dtpsearch.html).

By regular application of COMPARE, using selected prototype seed compounds from the Standard Agents Database, NCI has maintained ongoing surveillance of the total historical screening database accrued from inception to date. In this manner, compounds with screening fingerprints matching standard agent(s) having known or presumed known mechanism(s) of actions can be identified. NCI has been able to associate and subsequently confirm the database classification of compounds of previously unknown mechanisms of action into a number of different known mechanistic classes of interest. For example, new members have been classified within general mechanistic categories of tubulin-interactive antimitotics, antimetabolites, alkylating agents, topoisomerase inhibitors, DNA binders, and the like. These and numerous other examples resulting from this kind of database prospecting have been published, for example, in Paull et al., *Cancer Res.*, 52, 3892–3900 (1992), and references cited therein; and Paull et al., In: *Cancer Chemotherapeutic Agents*, Washington, D.C.: Am. Chem. Soc. Books, 1995, pp. 9–45, and references cited therein.

Users of the NCI screen (which is a public resource) can perform an analogous exercise using their own NCI screening data of a compound of interest to determine its relatedness or dissimilarity to any known anticancer mechanistic class. In this case, the investigator may compare a profile of interest to the readily accessible "Standard Agent Database" or to some selected individual member(s) thereof. Likewise, a profile of interest can be compared to other profiles which are suitably documented in the published literature, irrespective of whether any of the profiles to be compared are from compounds of known or unknown mechanistic classes.

When a new compound of either a new or a known anticancer mechanistic class is identified, the aforementioned methods can also be extended further to the elucidation of new members of the given mechanistic class (i.e., which have similar screening "fingerprints"). These techniques also can be applied similarly to the identification of mixtures of compounds, or crude extracts of natural products, which contain a new or known anticancer compound class of interest (for example, the crude extract exhibits the same or similar screening "fingerprint" as the compound class of interest contained therein).

The anticancer compounds of the present invention share unique structural features as well as an unprecedented and highly characteristic screening "fingerprint" in the NCI 60 cell-line screen that is distinct from any known conventional anticancer agent. COMPARE analyses of $GI_{50}$ and TGI mean-graph screening profiles of compounds of the present invention consistently show a high degree of commonality with each other (e.g., $GI_{50}$ and TGI-COMPARE Pearson correlation coefficients of at least 0.6–0.8 or greater) but do not show any such correlations to any known standard agent. Similarly, extracts of natural organisms which can be shown to contain compounds of the present invention typically give $GI_{50}$ and TGI mean-graph screening fingerprints with similarly high $GI_{50}$ and TGI-COMPARE Pearson correlations (e.g., typically 0.6–0.7 or greater) to the compounds of the present invention. This enables a practitioner of the art disclosed herein to readily identify productive source organisms and extracts thereof, from which the practitioner can readily obtain and use the compounds of the present invention. This enablement is further reinforced by the utility of certain characteristic NMR signals of the compounds of the present invention to further confirm the identification and selection of compound mixtures, including crude extracts of natural organisms and partially purified fractions thereof, which contain said compounds. This is illustrated further as follows.

FIG. 1 shows the structural locations of ten protons, depicted as hydrogen atoms ($H^1$–$H^{10}$), shared by preferred compounds of the present invention. Proton NMR spectroscopy (500 MHZ) of compounds of the present invention shows that these ten protons produce resonances with chemical shift values that, taken together, are highly characteristic of these compounds. These characteristic NMR peaks (which may vary in multiplicity depending upon the specific compound) are consistently centered within the following ranges of chemical shift values (when recorded in $CD_3OD$ and referenced to residual methanol): $H^1$, 6.60–6.70; $H^2$, 7.10–7.20; $H^3$, 6.65–6.75; $H^4$, 5.30–5.70; $H^{5,6}$, 2.30–2.60; $H^7$, 5.00–5.45; $H^8$, 6.70–6.90; $H^9$, 5.60–6.30; $H^{10}$, 6.40–7.20. For example, the particular $^1H$ NMR(500 MHz) chemical shifts and multiplicities of resonances for $H^1$–$H^{10}$ (in $CD_3OD$) for exemplary compounds of the present invention, salicylihalamides A and B, and lobatamides A and B, are illustrated below in Table 1.

TABLE 1

| H-Atom # | Salicyli-halamide A ($^1H$ δ) | Salicyli-halamide B ($^1H$ δ) | Lobatamide A ($^1H$ δ) | Lobatamide B ($^1H$ δ) |
|---|---|---|---|---|
| 1 | 6.65 d | 6.66 d | 6.63 d | 6.63 d |
| 2 | 7.12 t | 7.12 t | 7.14 dd | 7.14 dd |
| 3 | 6.72 d | 6.71 d | 6.68 d | 6.68 d |
| 4 | 5.36 m | 5.41 m | 5.58 m | 5.58 m |
| 5,6 | 2.39 ddd, 2.42 ddd | 2.43 ddd, 2.53 ddd | 2.48 dd | 2.48 br. t |
| 7 | 5.36 m | 5.07 ddd | 5.34 dt | 5.34 m |
| 8 | 6.80 d | 6.73 d | 6.82 d | 6.82 d |
| 9 | 5.68 d | 5.84 d | 6.04 d | 6.05 d |
| 10 | 6.87 dt | 6.87 dt | 6.45 dd | 7.04 dd |

At least six of the characteristic resonances (specifically those representing $H_1$–$H_3$ and $H_8$–$H_{10}$) of the compound(s) of the present invention are readily discernible in crude extracts of natural organisms that contain said compound(s). Thus, extracts of natural organisms which contain one or more compounds of the present invention and which thereby exhibit the desired characteristic mean-graph screening profile (i.e., specifically showing greater than or equal to 0.6–0.7 $GI_{50}$- and/or TGI-COMPARE correlations to the corresponding screening profile of a representative pure compound of the present invention) can be even more definitively identified based upon the presence, in the proton NMR spectrum of the crude extract, of the aforementioned characteristic resonances for $H^1$–$H^3$ and $H^8$–$H^{10}$. Once such an extract is selected, a practitioner of the art can obtain the useful compounds of the present invention according to the description herein, an example of which is illustrated in Example 1.

Further provided is a method of obtaining the compounds of the present invention. Compounds of the present invention can be readily obtained from natural sources, more specifically from solvent extracts of marine sponges and tunicates, and more specifically yet from aqueous and organic solvent extracts of sponge species from the genus Haliclona and tunicate species from the genus Aplidium.

Extracts of Haliclona sponges or Aplidium tunicates can be prepared using organic solvents, water, and mixtures thereof; fresh sponges or tunicates can be used, but more generally they are frozen immediately after harvesting, and then either are used directly or freeze-dried before the extraction is done. Preferably the marine sponge is from the genus Haliclona; more preferably it is a Haliclona species, and most preferably it is a Haliclona species collected near Rottnest Island, Western Australia (see Example 1). Preferably, the tunicate is from the genus Aplidium; more preferably it is an Aplidium species; more preferably yet it is *Aplidium lobatum*, and most preferably it is *Aplidium lobatum* collected off the southwestern coast of Australia due west of Hillary Boat Harbor (see Example 1).

Specific extracts of Haliclona and Aplidium species that contain compounds of the present invention can be identified and selected based upon the anticancer screening profile they produce in the NCI 60-cell human tumor screen which is characteristic of the presence of these compounds, and/or key proton NMR signals (Table 1) that are characteristic of the structural component motif (FIG. 1) shared by preferred compounds of the present invention (see as described above and also Example 1).

From the aforementioned selected extracts, a variety of methods can be used for isolation and purification of compounds of the present invention. During each step of isolation and purification, the anticancer potency and aforementioned characteristic anticancer screening profile, and the aforementioned characteristic proton NMR signals, can be obtained for intermediate fractions, as well as partially purified and purified compounds, to ensure obtaining desired, substantially pure, compounds of the present invention.

A preferred general method of obtaining the compounds of the present invention comprises the steps of:

(a) obtaining a fresh or frozen sample of said marine sponge or tunicate (or other suitable natural source material), (b) extracting the compound(s) from the sample with water or organic solvent(s) which dissolves the compound(s) to form an aqueous or organic extract, (c) optionally treating the extract with ethanol to precipitate and remove high molecular weight proteins and sulfated polysaccharides, (d) partitioning the extract between a nonpolar organic solvent and an aqueous solvent to form a partitioned aqueous, nonpolar or polar organic extract containing the desired compound(s), (e) chromatographing the partitioned extract, for example, on an adsorption, partition, or size-exclusion matrix, to form fractions, and (f) isolating compound(s) of the present invention from the fraction(s) containing it (them).

In step (b), the organic solvent which dissolves the compound(s) is generally a mixture of a suitable nonpolar organic solvent and a suitable polar organic solvent. Suitable nonpolar organic solvents include, for example, $CH_2Cl_2$, $CHCl_3$, toluene, and hexane. Suitable polar organic solvents include, for example, MeOH, EtOH, isopropyl alcohol, and acetone. In step (d) suitable organic nonpolar solvents include $CH_2Cl_2$, hexane, $CCl_4$, $CHCl_3$, MeOtBu, and ethyl acetate; and typical aqueous solvents are mixtures of water and methanol. Non-limiting examples of solvent mixtures that can be used in this partitioning step include: (1) $CH_2Cl_2$ vs. 19:1 $H_2O$—MeOH, (2) hexane vs. 9:1 MeOH—$H_2O$, (3) $CCl_4$ vs. 8:2 MeOH—$H_2O$, (4) $CH_2Cl_2$ vs. 7:3 MeOH—$H_2O$, and (5) EtOAc vs. $H_2O$. In step (d), the chromatography typically is column chromatography, and the chromatographic matrix preferably is the adsorption type, or the partition type, or the size exclusion type, or a combination of any of these, with the proviso that the solvent and the matrix cannot be acidic in nature due to the instability of the compounds of the present invention to acidic conditions. Sephadex® LH-20 combines all three of these types, and is characterized by mild treatment and good recoveries. Sephadex® LH-20 is the most preferred chromatographic matrix material. The isolation step (f) can be carried out, for example, by either simply evaporating the solvent or by recrystallization.

Typically, a selected sample of frozen Haliclona species sponge is ground to a powder with dry ice. The dry ice is allowed to sublime, distilled $H_2O$ is added, and the thawed material is stirred for 3 h at 3° C., then centrifuged. The marc is lyophilized and extracted with a mixture of $CH_2Cl_2$—MeOH (1:1 v/v) at room temperature (e.g., 20–25° C.) overnight. The solvent is drained, and the marc is rinsed with MeOH. The combined organic extracts are evaporated to dryness. The crude organic extract is subjected to vacuum-liquid chromatography in several batches on Diol-60 columns, eluting successively with hexane, $CH_2Cl_2$—MeOH EtOAc, acetone, and MeOH. The EtOAc fraction is passed through a column of Sephadex® LH-20 with $CH_2Cl_2$—MeOH (1:1) to give a fraction with the characteristic bioactivity profile and NMR signals of the compound (s) of the present invention. A second Sephadex® LH-20 column is eluted with hexane-toluene-MeOH (3:2:2) to afford substantially purified compound(s) of the present invention. Salicylihalamide A (FIG. 3A) and its $\Delta^{17}$-cis-isomer (salicylihalamide B) (FIG. 3C) are isolated by C-18 reverse-phase HPLC (using a linear gradient from 70% to 100% MeOH) in pure form. More specific illustrations of isolation of compounds of the present invention are given in Example 1 herein.

The definitive proofs of structure of the isolated compounds can be obtained by a combination of methods including primary spectral analyses (e.g., high-resolution NMR and mass spectrometry, infrared and UV spectroscopy), comparisons of spectral and physicochemical properties with related literature precedents, and by x-ray crystallographic analysis. These are further illustrated in Example 2 herein.

The following examples further illustrate the present invention but, of course, should not be construed as in any way limiting its scope. It is understood that modifications can be made in the procedures set forth herein without departing from the present invention.

EXAMPLE 1

This example illustrates a procedure for obtaining compounds of the present invention from marine sponges and tunicates.

The particular extract of a Haliclona sp. sponge selected from the NCI Natural Products Repository, Frederick, Md., for investigation in the present example showed an NCI 60-cell screening mean-graph (TGI) fingerprint that was highly correlated (TGI-COMPARE Pearson correlation coefficient greater than or equal to 0.7) to that of either salicylihalamide A or lobatamide A. The extract also showed proton NMR (500 MHz) resonances at chemical shift values (and multiplicities) recorded in $CD_3OD$ and referenced to residual methanol of: 6.65(d), 7.12(t), 6.72(d), 6.80(d), 5.68(d), and 6.87(dt). The selected extract was from a Haliclona sp. sponge that had been collected by P. Murphy in Southwestern Australia, 0.7 nautical miles off Rottnest Island, in March, 1989, at a depth of 15 meters. The sponge reportedly occurred as a green mass with amorphous lobes, growing on the underside of a rocky overhang, and was identified by P. Jane Fromont of James Cook University. A voucher specimen of this particular sponge collection (coded as serial number Q66C2670) is on deposit at the Smithsonian Institution Taxonomy and Sorting Center, Suitland, Md.

Salicylihalamides A and B (FIG. 3A and FIG. 3C, respectively) were isolated as follows. Approximately 450 g frozen wet wt. of the sponge was ground to a powder with dry ice. The dry ice was allowed to sublime, distilled $H_2O$ was added, and the thawed material was stirred for 3 h at 3° C., then centrifuged. The marc was freeze-dried and extracted with a mixture of $CH_2Cl_2$—MeOH (1:1 v/v) at room temperature overnight. The solvent was removed by filtration, and the marc was rinsed with MeOH. The combined solutions were evaporated to yield approximately 3.5 g of crude extract.

Initial attempts to isolate the active constituents revealed that the bioactivity was lost from crude extracts and chromatographic fractions thereof in the presence of deuterated chloroform. For example, overnight storage of $CDCl_3$ solutions of partially purified fractions resulted in the formation of a tarry, insoluble residue that was inactive in the anticancer screen. Therefore, all subsequent attempts at isolation avoided the use of chloroform or exposure of samples to $CDCl_3$, and no further problems with decomposition or loss of bioactivity were encountered. Moreover, there was no indication of any instability of the pure isolated compounds in any of the other common organic solvents employed, nor in aqueous or biological media. Therefore, a typical isolation and purification of the salicylihalamides from the selected crude extract is as follows.

An aliquot of extract (330 mg) was coated on 2.1 g of diol bonded phase and sequentially batch-eluted with 100 ml portions of hexane, $CH_2Cl_2$, EtOAc, acetone, and MeOH. The cytotoxic $CH_2Cl_2$ and EtOAc eluates were combined (107 mg) and permeated through Sephadex® LH-20 with hexane-toluene-MeOH (3:2:2 v/v, 1.5×45 cm column) to yield four fractions, the second of which (8.4 mg) showed NMR signals corresponding to salicylihalamide A. HPLC on wide-pore C-18 (Rainin 1×25 cm) using a linear gradient from 70% to 100% MeOH over 20 min yielded 5.5 mg of pure salicylihalamide A (FIG. 3A) (retention time 13 min) and a smaller amount (approximately 0.5 mg) of salicylihalamide B (FIG. 3C) (retention time 14.5 min).

Physicochemical and spectroanalytical data for salicylihalamide A were as follows: amorphous solid; $[\alpha]_D$–35° (c=0.7, MeOH); $\lambda_{max}$ (MeOH) 280 nm ($\epsilon$=34,000); $\upsilon_{max}$ (film) 3288, 2964, 1697, 1651, 1606, 1588, 1520, 1464, 1293, 1268, 1247, 1214, 1123, 1068, 972, 869, 735 cm$^{-1}$; for $^1$H and $^{13}$C NMR, see Example 2, Table 2 (below); EIMS m/z 439 [M$^+$] (43), 421 (1), 410 (5), 409 (2), 392 (2), 330 (7), 315 (8), 313 (3), 312 (3), 296 (10), 288 (12), 278 (4), 231 (12), 191 (40), 149 (17), 125 (18), 124 (6), 109 (100), 108 (19), 107 (16), 96 (63), 91 (10), 83 (31), 82 (50), 81 (87), 79 (35), 56 (27), 55 (24), 43 (14), 18 (19); HREIMS m/z 439.2354 (M$^+$, calcd for $C_{26}H_{33}NO_5$, 439.2350).

Physicochemical and spectroanalytical data for salicylihalamide B were as follows: amorphous solid; $[\alpha]_D$–73° C. (c=0.3, MeOH); $\lambda_{max}$ (MeOH) 280 nm ($\epsilon$=38,000); $\upsilon_{max}$ (film) 3356, 2964, 2923, 1690, 1651, 1588, 1503, 1463, 1294, 1246, 1212, 1121, 1032, 972 cm$^{-1}$; $^1$H NMR ($C_6D6$) δ 0.77 (3H, t, 7.3), 0.83 (3H, d, 6.8), 1.22 (dd, 15.2, 8.8), 1.32 (br s), 1.50 (br q, 6.8), 1.73 (br m), 1.74 (dd, 15.2, 10.5), 1.89 (ddd, 15.2, 7.8, 7.4), 1.95 (2H, quintet, 7.3), 2.05 (ddd, 14.7, 6.8, 6.4), 2.08 (br m), 3.25 (br d, 16.5), 3.27 (br d, 8.8), 3.56 (dd, 16.5, 4.9), 4.52 (dt, 10.2, 8.8, 8.8), 5.08 (ddd, 15.6, 7.3, 6.4), 5.17 (very br m), 5.20 (very br m), 5.48 (d, 11.2), 5.62 (dt, 10.7, 7.8, 7.3), 6.45 (dd, 8.3, 3.9), 6.62 (dd, 11.2, 10.8), 6.95 (m), 7.29 (t, 10.3), 7.66 (br d, 10.2), 7.93 (t, 10.8), 11.58 (br s); $^{13}$C NMR ($C_6D_6$) δ 13.8, 14.0, 20.8, 31.5, 36.2, 38.0, 38.4, 39.4, 70.9, 76.1, 103.3, 117.2, 119.5, 123.7, 124.9, 125.4, 126.8, 132.8, 134.6, 137.4, 141.9, 163.0, 172.0 (3 of the quaternary carbons were not observed); HREIMS m/z 439.2351 (M$^+$, calcd for $C_{26}H_{33}NO_5$, 439.2350).

The extract of *Aplidium lobatum* selected from the NCI Natural Products Repository, Frederick, Md., for investigation in the present example showed an NCI 60-cell screening mean-graph (TGI) fingerprint that was highly correlated (TGI-COMPARE Pearson correlation coefficient greater than or equal to 0.7) to that of either salicylihalamide A or lobatamide A. The extract also showed proton NMR (500 MHZ) resonances at chemical shift values (and multiplicities) recorded in $CD_3OD$ and referenced to residual methanol of: 6.63(d), 7.14(t), 6.68(d), 6.82(d), 6.04(d), and 6.45(dd). The selected extract was from an *Aplidium lobatum* collected by P. Murphy off the southwestern coast of Australia due west of Hillary Boat Harbor at a depth of 6 meters. The taxonomy was provided by Patricia Kott of the Queensland Museum. Voucher specimens of this particular tunicate collection (coded as serial number Q66C2780) are on deposit both at the Australian Institute of Marine Science and the Smithsonian Institute. Lobatamides A and B (FIGS. 3B and 3D, respectively) were isolated as follows.

The A. lobatum (642 g wet weight) was frozen immediately after collection until extraction. The aqueous extract (13.8 g) was first taken through an EtOH precipitation procedure to remove high molecular weight proteins and sulfated polysaccharides as follows. The extract was divided into 5 g aliquots, each of which was dissolved in $H_2O$ (40 ml) followed by addition of EtOH (40 ml). The solutions were allowed to sit overnight at $-20°$ C., after which the precipitates were pelleted by centrifugation, and the supernatants were decanted and combined. The combined precipitate was washed with $H_2O$-EtOH (1:1, 40 ml) and pelleted again with centrifugation. The wash was decanted and added to the combined supernatant. The ETOH was removed from the combined supernatant by rotary evaporation, and the remaining $H_2O$ was removed by lyophilization. The lyophilized supernatant was partitioned between EtOAc and $H_2O$ to yield cytotoxic EtOAc soluble materials enriched in the compounds of interest, as determined both by the aforementioned characteristic NCI 60 cell-line screening profile and proton NMR chemical shifts. This EtOAc-soluble material was sequentially chromatographed using gel permeation (Sephadex® LH-20, 1:1 MeOH-MeCN), followed by VLC (amino-bonded phase, $CH_2Cl_2$—MeOH gradient 100–90% $CH_2Cl_2$), Sanki CPC (5:7:4 $CHCl_3$—MeOH—$H_2O$, ascending mode, 1.7 ml/min), and finally HPLC ($C_{18}$, 3:7 MeCN—$H_2O$) to yield lobatamide A (1.1 mg, $8.0 \times 10^{-3}$% wet wt) and lobatamide B (1.4 mg, 0.01% wet wt).

Physicochemical and spectroanalytical data obtained for lobatamide A were as follows: $[\alpha]_D$-7.9° (c 0.24, MeOH); UV (MeOH) $\lambda_{max}$ 273 nm (log ε 4.22); IR (film) $\upsilon_{max}$ 3590–3128 (br), 2974, 2933, 1739, 1656, 1523, 1461, 1451, 1374, 1266, 1215, 1169, 1113, 1042 cm$^{-1}$; HRFABMS (noba) MH$^+$ m/z 513.2257 for $C_{27}H_{33}N_2O_8$ Δ+2.0 mmu; FABMS (magic bullet) m/z 535 (M+Na$^+$, 8%) 513 (MH$^+$, 16), 495 (15), 460 (20), 289 (65), 239 (22), 176 (30), 154 (100), 138 (100), 105 (83).

FAB mass spectra were obtained on a JEOL SX102 spectrometer using a 10 kV xenon gun to desorb the samples from a magic bullet matrix (5:1 DTT-DTE). Spectra were run in both positive and negative ionization conditions. Fragmentation analyses were performed by B/E linked scans of the parent and fragmentation ions. Where necessary, a helium collision gas was used in the first field free region to enhance this fragmentation. Exchange spectra were performed under chemical ionization (CI) conditions on a Finnigan 4500 spectrometer using the direct exposure probe. Exchanges were determined by comparing spectra obtained using $ND_3$ as the reagent gas with those from $NH_3$. HRFABMS data for structurally significant fragments were as follows: II: 495.2115 for $C_{27}H_{31}N_2O_7$, calcd 495.2131; 3 exchangeable protons; III: 239.1021 for $C_{11}H_{15}N_2O_4$, calcd 239.1032; 2 exchangeable protons; V: 112.0402 for $C_5H_6NO_2$, calcd 112.0399; VI: seen in CI only; 3 exchangeable protons; VII: 257.1129 for $C_{16}H_{17}O_3$, calcd 257.1137; 2 exchangeable protons; VIII: 291.1231 for $C_{16}H_{19}O_5$, calcd 291.1231; IX: 273.1118 for $C_{16}H_{17}O_4$, calcd 273.1127; X: 219.0650 for $C_{12}H_{11}O_4$, calcd 219.0657.

Physicochemical and spectroanalytical data obtained for lobatamide B were as follows: $[\alpha]_D$-15° (c 0.03, MeOH); UV (MeOH) $\lambda_{max}$ 288 nm (log ε 4.55); IR (film) $\upsilon_{max}$ 3580–3118 (br), 3056, 2974, 2933, 1733, 1651, 1605, 1584, 1528, 1467, 1451, 1267, 1221, 1175, 1113, 1046 cm$^{-1}$; HRFABMS (magic bullet) MH$^+$m/z 513.2244 for $C_{27}H_{33}N_2O_8$ Δ+0.7 mmu; FABMS (glyc) m/z 513 (MH$^+$, 10%), 495 (10), 461 (8), 279 (55), 239 (23), 177 (25), 153 (100), 135 (100).

EXAMPLE 2

This example illustrates the structure proofs of representative compounds of the present invention.

Salicylihalamide A (FIG. 3A), such as obtained and characterized spectroanalytically in Example 1, was an amorphous solid with a molecular formula established by HREIMS as $C_{26}H_{33}NO_5$. The $^{13}C$ and DEPT NMR spectra (Table 2) showed 26 unique resonances: 5 quaternary, 14 methine, 5 methylene, and 2 methyl carbons. Chemical shift values further characterized two ester or amide carbonyls, 14 olefinic or aromatic carbons, and two oxygenated methines. Three exchangeable protons completed the proton count. The IR spectrum confirmed OH and/or NH (3288 cm$^{-1}$) functionalities and suggested the presence of both an amide (1651 cm$^{-1}$) and an intramolecularly hydrogen-bonded conjugated ester (1697 cm$^{-1}$). The $^{13}C$ (125 MHz) and $^1H$ (500 MHz) NMR data for salicylihalamide A (FIG. 3A) in $C_6D_6$ and $CD_3OD$ are illustrated below in Table 2.

TABLE 2

| C# | $\delta_c$ ($C_6D_6$) | $\delta_H$ (multiplicity, Hz) ($C_6D_6$)[a] | HMBC ($^1H$ Correlation, $C_6D_6$) | $\delta_c$ ($CD_3OD$) | $\delta_H$ (multiplicity, Hz) ($CD_3OD$)[a] | HMBC ($^1H$ correlation, $CD_3OD$) |
|---|---|---|---|---|---|---|
| 1 | 171.2 | — | 15 | 171.0 | — | 15 |
| 2 | 114.7[b] | — | 4, 6, 8a, 8b | 123.0 | — | 6 |
| 3 | 163.0 | — | 4 and/or 5 | 157.1 | — | 5 |
| 4 | 117.1 | 6.97 (m) | 5, 6 | 115.3 | 6.72 (d, 7.3) | 6 |
| 5 | 134.0 | 6.97 (m) | 6 | 131.6 | 7.12 (t, 7.3) | — |
| 6 | 123.6 | 6.48 (dd, 6.4, 2.0) | 4 and/or 5, 8a, 8b | 122.5 | 6.65 (d, 7.3) | 4, 8b |
| 7 | 142.6 | — | 5, 6, 8a, 8b, 9 | 140.7 | — | 5, 8b |
| 8 | 39.3 | 3.32 (br d, 16.6) | 9 | 38.8 | 3.34 (br dd, 16.6, 7.8) | 6, 9, 10 |
|   |   | 3.61 (br dd, 16.6, 4.9) |   |   | 3.56 (dd, 16.6, 8.3) |   |
| 9 | 132.7 | 5.28 (dt, 15.1, 4.9, 4.4) | 8a, 8b, 11a, 11b | 130.7 | 5.29 (dddd, 15.2, 8.3, 7.8, 1.5) | 8b, 11b |
| 10 | 127.0 | 5.05 (br m) | 8a, 8b, 11a, 11b | 131.7 | 5.36 (m) | 8b, 11a |
| 11 | 38.5 | 1.65 (dd, 13.7, 8.8) | 9, 13, 26 | 38.9 | 1.75 (m) | 9, 10 |
|   |   | 2.12 (m) |   |   | 2.28 (m) |   |
| 12 | 37.6 | 1.51 (br dq, 6.8, 3.5) | 11a, 13, 14b, 26 | 38.6 | 1.87 (br m) |   |

TABLE 2-continued

| C# | $\delta_c$ (C$_6$D$_6$) | $\delta_H$ (multiplicity, Hz) (C$_6$D$_6$)[a] | HMBC ($^1$H Correlation, C$_6$D$_6$) | $\delta_c$ (CD$_3$OD) | $\delta_H$ (multiplicity, Hz) (CD$_3$OD)[a] | HMBC ($^1$H correlation, CD$_3$OD) |
|---|---|---|---|---|---|---|
| 13 | 70.5 | 3.46 (dd, 8.8, 3.5) | 14a, 15, 26 | 72.0 | 4.12 (dd, 9.3, 3.4) | 14a, 15 |
| 14 | 35.4 | 1.28 (dd, 15.0, 8.8) 1.66 (dd, 15.0, 10.3) | 13, 15, 16a, 16b | 36.6 | 1.37 (dd, 15.3, 9.3) 1.75 (m) | 13, 15, 16 |
| 15 | 75.3 | 5.55 (dt, 10.3, 6.5) | 13, 14b, 16a, 16b, 17 | 76.0 | 5.36 (m) | 13, 14b, 16 |
| 16 | 36.3 | 2.07 (ddd, 14.6, 7.3, 6.5) 2.20 (ddd, 14.6, 7.3, 6.5) | 14b, 15, 17 | 37.6 | 2.39 (ddd, 14.2, 6.8, 6.3) 2.42 (ddd, 14.2, 6.8, 6.3) | 15, 17 |
| 17 | 107.0 | 4.84 (dt, 14.5, 7.3) | 15, 16a, 16b | 110.4 | 5.36 (m) | 15, 16 |
| 18 | 126.0 | 7.13 (dd, 14.5, 10.8) | 16a, 16b, 17 | 126.2 | 6.80 (d, 14.7) | 16 |
| 19 | 162.9 | — | 20, 21, NH | 165.9 | — | 20, 21 |
| 20 | 119.6 | 5.17 (d, 11.2) | — | 120.3 | 5.68 (d, 11.7) | — |
| 21 | 136.9 | 6.62 (dt, 11.2, 1.0) | 20, 23 | 137.7 | 6.87 (dt, 11.7, 1.0) | 23 |
| 22 | 124.9 | 7.92 (dt, 10.8, 1.5) | 20, 24 | 125.3 | 7.30 (dt, 10.7, 1.5) | 20, 24 |
| 23 | 141.7 | 5.63 (ddddd, 10.8, 7.3, 7.3, 1.0, 1.0) | 21, 24, 25 | 142.6 | 5.82 (ddddd, 10.7, 7.4, 7.4, 1.4, 1.0) | 21, 24, 25 |
| 24 | 20.8 | 1.97 (d quintets, 7.3, 7.3, 7.3, 7.3, 1.5) | 23, 25 | 21.5 | 2.28 (d quintets, 7.4, 7.4, 7.4, 7.4, 1.5) | 22, 23, 25 |
| 25 | 14.0 | 0.77 (t, 7.3) | 23, 24 | 14.4 | 1.02 (t, 7.4) | 23, 24 |
| 26 | 13.9 | 0.82 (d, 6.8) | 11a, 13 | 13.6 | 0.85 (d, 6.8) | 11b, 13 |
| NH | — | 6.76 (d, 10.8) | — | — | — | — |
| OH (C-3) | — | 11.46 (br s) | — | — | — | — |

[a]With geminal protons, the smaller δ-value is given the "a" designation, the larger δ-value is given the "b" designation.
[b]Weak and broad.

Because of the sensitivity of salicylihalamide A to CDCl$_3$, all NMR spectroscopy experiments were carried out in C$_6$D$_6$ or CD$_3$OD. Signals obscured by or unresolved in the first solvent were readily discernible in the second. Consequently, $^1$H—$^1$H COSY, HMQC, and HMBC NMR data were gathered in both solvents. The $^1$H—$^1$H COSY spectrum of salicylihalamide A in C$_6$D$_6$ revealed the following correlations (H/H): 4/6, 5/6, 8a/8b, 8a/9, 8a/10, 8a/11b, 8b/9, 9/10, 10/11a, 10/11b, 11a/11b, 11a/12, 11b/12, 12/13, 12/26, 13/14a, 13/14b, 14a/14b, 14a/15, 14b/15, 15/16a, 15/16b, 16a/16b, 16a/17, 16a/18, 16b/17, 16b/18, 17/18, 18/NH, 20/21, 20/22, 20/23, 21/22, 21/23, 22/23, 22/24, 23/24, 24/25. From a combination of the HMQC (Table 2) and the COSY spectral data, the partial structures illustrated in FIGS. 5A–5C were generated.

Figure 5A:
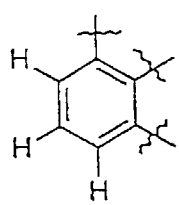
FIG. 5A illustrates a component partial structure used in the structure analysis of salicylihalamide A.
Figure 5B:
FIG. 5B illustrates a component partial structure used in the structure analysis of salicylihalamide A.
Figure 5C:
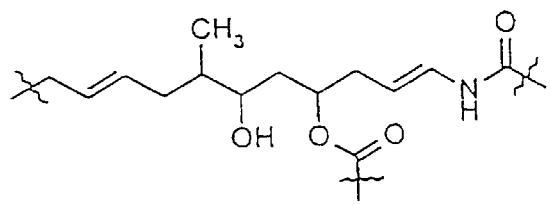
FIG. 5C illustrates a component partial structure used in the structure analysis of salicylihalamide A.

The enamide functionality in segment C (FIG. 5C) was identified through a 10.8 Hz coupling between the adjacent olefinic and amide N—H protons; the latter was characterized by its variable chemical shift values. All 26 carbons were accounted for in partial structures A, B, and C, corresponding to FIGS. 5A, 5B, and 5C, respectively. In the HMBC spectra (Table 2), coupling between the two vinyl hydrogens [δ 5.17 (H-20) and 6.62 (H-21) in C$_6$D$_6$; δ 5.68 and 6.87 in CD$_3$OD] of the hexadiene substructure B (FIG. 5B) and the amide carbonyl (δ 162.9 in C$_6$D$_6$ and 165.9 in CD$_3$OD) of substructure C (FIG. 5C) established the connection of B to C through this amide carbonyl carbon. This was confirmed by an HMBC correlation between the amide proton and carbonyl in C$_6$D$_6$ and by the base peak in the mass spectrum (m/z 109, C$_7$H$_9$O). The IR spectral evidence that the ester carbonyl was both conjugated and intramolecularly hydrogen-bonded (1697 cm$^{-1}$) was supported by the low-field chemical shift of the phenolic OH (δ 11.46, C$_6$D$_6$). This indicated that the ester carbonyl was ortho to the phenolic OH in substructure A (FIG. 5A). The remaining open aromatic position then had to be occupied by the allylic carbon of moiety C (FIG. 5C), giving the macrolide shown in FIG. 3A as the final planar structure for salicylihalamide A.

Confirmation of the aromatic substitution pattern came from HMBC correlations, which were optimized for 8.3 Hz couplings. In CD$_3$OD, the phenolic carbon and the amide carbonyl carbon were resolved, as were all three aromatic protons and all six aromatic carbons. Moreover, the latter were not obscured by solvent resonances. In CD$_{30}$D, the aromatic proton at δ 7.12 (H-5) showed a correlation to both the oxygen-bearing phenolic carbon at δ 157.1 (C-3) and the quaternary aromatic carbon at 140.7 (C-7). As this δ 7.12 proton was a triplet (J=7.3 Hz) in the $^1$H NMR spectrum, the two quaternary aromatic carbons to which it was correlated were meta to it. The δ 6.65 (H-6) aromatic hydrogen showed correlation to two different aromatic carbons, the methine at δ 115.3 (C-4) and the quaternary carbon at δ 123.0 (C-2). Furthermore, the δ 6.65 proton was correlated to the side-chain aliphatic carbon at δ 38.8 (C-8), necessitating the placement of this side-chain ortho to the δ 6.65 hydrogen. To accommodate an ortho substituent and account for its chemical shift, this δ 6.65 hydrogen had to be para to the phenolic OH. Confirming this assignment were the correlations observed between the benzylic proton (H-8, δ 3.56) of the side-chain and both the quaternary aromatic carbon at δ 140.7 (C-7) and the δ 122.5 (C-6) aromatic carbon bearing the δ 6.65 hydrogen. The only remaining aromatic site for the ester carbonyl attachment was that ortho to the phenolic OH (at δ 123.0), as shown in the structure (FIG. 3A) for salicylihalamide A. Additional HMBC correlations are shown in Table 2.

Figure 6:
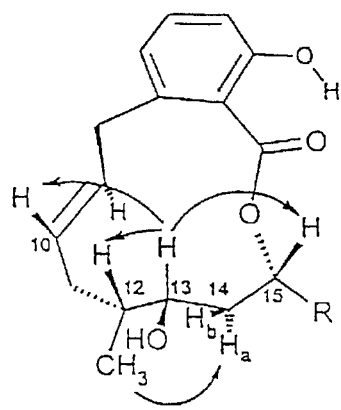
FIG. 6 illustrates selected nOe relationships in salicylihalamide A.
Figure 7:
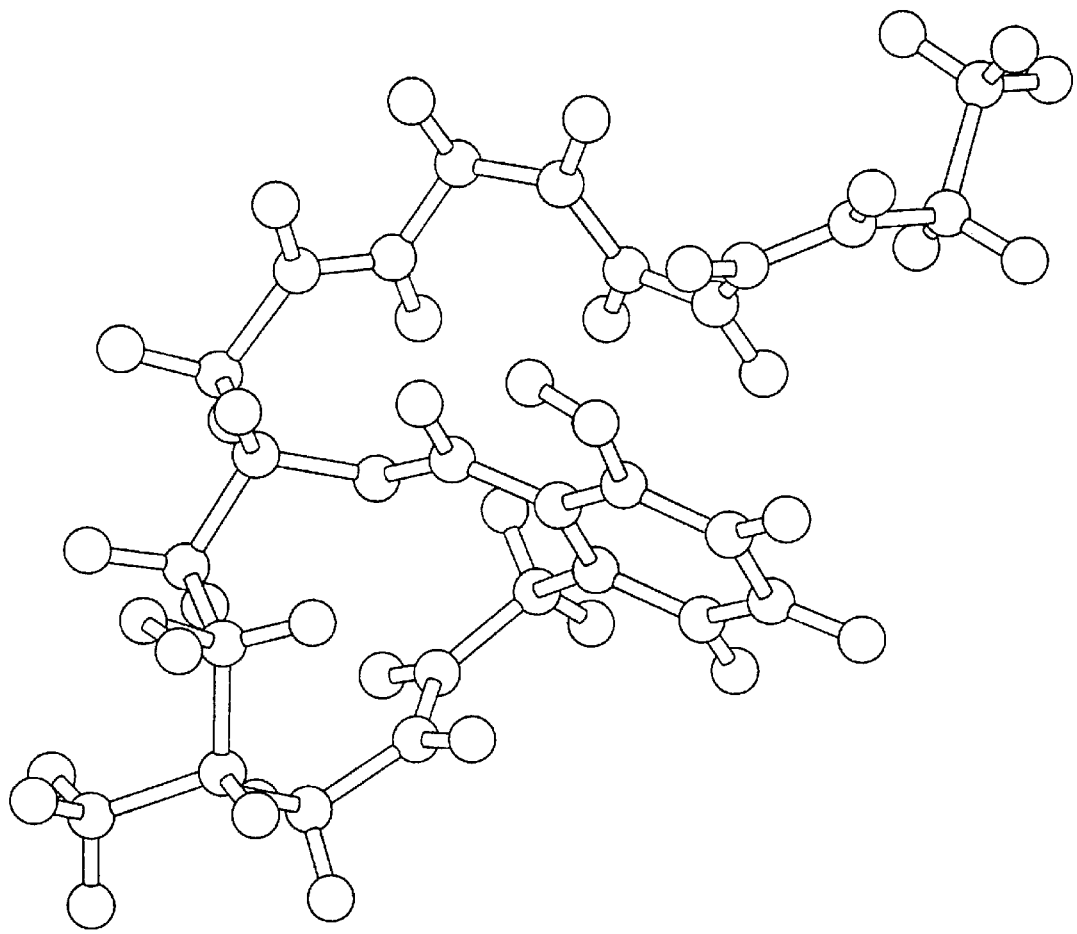
FIG. 7 shows a computer-generated model of the conformation of salicylihalamide A.

The relative stereochemistry of salicylihalamide A was deduced from a combination of $^1$H—$^1$H coupling constants and difference nOe spectra. FIG. 6 illustrates important nOe interactions; most notable were the interactions of the alcohol methine (H-13) with the ester methine (H-15), the methyl-bearing methine (H-12), and the olefinic hydrogen (H-10). All four of these protons must reside on the same face of the molecule, leading to the relative stereochemistry depicted in FIG. 4. The dihedral angle between the ester methine (H-15) and H-14a must be approximately 90°, since no coupling was observed between these two vicinal hydrogens. The dihedral angle between H-15 and H-14b must approach 180° to accommodate both their coupling constant (10.3 Hz) and the lack of a measurable nOe between them. Likewise, H-14b and the alcohol methine (H-13) showed no measurable coupling, indicating a dihedral angle of approximately 90°, while a large dihedral angle between H-14a and H-13 was needed to accommodate a sizeable coupling (8.8 Hz). H-13, in turn, displayed a J-value of 3.5 Hz and a substantial nOe with H-12, suggesting a dihedral angle of approximately 60° between these two protons. Molecular modeling studies, generating minimum energy structures with the nOe constraints described above, gave rise to predicted J-values that agreed within 1–1.5 Hz of the actual experimental values. FIG. 7 depicts one such computer-generated model of salicylihalamide A. Thermodynamic modeling calculations were performed using Macromodel v3.0 [Mohamadi et al., *J. Computat. Chem.*, 11, 440–467 (1990)] implemented on a VAX 6620 computer. An input model with a flat macrolide structure with relative stereochemistry constructed by Dreiding models was drawn by hand. Distance constraints were applied sequentially, and energy minimization was performed at each step. After constraints corresponding to the prominent observed transannular nOe's had been applied, the constraints were removed, and the structure was minimized without constraint to produce the final model. The graphic (FIG. 7) was produced by downloading the structure and printing from the Chem3D program.

The question of absolute stereochemistry was addressed through the use of Mosher esters. See Ohtani et al., *J. Org. Chem.*, 56, 1296–1297 (1991); Dale et al., *J. Am. Chem. Soc.*, 95, 512–519 (1973); Oh et al., *J. Org. Chem.*, 54, 4499–4503 (1989); Leclercq et al., *Tetrahedron Lett.*, 50, 8465–8488 (1994); and Kaneko et al., *Tetrahedron Lett.*, 35, 4107–4110 (1994). Both the (R)- and (S)-methoxy trifluoromethylphenyl acetate (MTPA) diesters of salicylihalamide A were prepared and subjected to $^1$H NMR analysis (Table 3). A small amount of the tris-MTPA derivative (diester imide) was formed in each case and was removed by preparative TLC prior to NMR analyses. The Mosher ester analysis of salicylihalamide A (FIG. 3A) in $C_6D_6$ is illustrated below in Table 3.

TABLE 3

|  | H-10 | H-26 | H-14a | H-15 | H-17 |
|---|---|---|---|---|---|
| R-MTPA diester | 4.92 | 0.52 | 1.58 | 5.55 | 4.64 |
| S-MTPA diester | 5.58 | 0.63 | 1.52 | 5.04 | 4.44 |
| Δ ($\delta_S-\delta_R$) | +0.66 | +0.11 | −0.06 | −0.51 | −0.20 |

The preparation of the MTPA esters was performed as follows. To a mixture of 0.5 mg of salicylihalamide in 10 μl of anhydrous $CH_2Cl_2$ and 15 μl of anhydrous pyridine in a septum-sealed vial were added 1.2 μl of the enantiomercially pure α-methoxy-α-trifluoromethyl phenylacetyl chloride. The reaction mixture was allowed to stand at 25° C. for 16 h. $H_2O$ and $CH_2Cl_2$ were added, and the $CH_2Cl_2$ layer was washed several times with $H_2O$, then passed through a short column of anhydrous $Na_2SO_4$ and evaporated to dryness under $N_2$. The residue was subjected to reverse-phase TLC ($C_{18}$) with MeOH to give di- and tri-MTPA derivatives. Mass spectral data were as follows: (diesters)HRFABMS m/z 872.324 [(R)-derivative]; 872.323 [(S)-derivative] (MH$^+$, calcd for $C_{46}H_{48}F_6NO_9$, 872.322); (diester imides) HRFABMS m/z 1088.361 [(R)-derivative]; 1088.362[(S)-derivative] (MH$^+$, calcd for $C_{56}H_{55}F_9NO_{11}$, 1088.362).

Figure 8A:
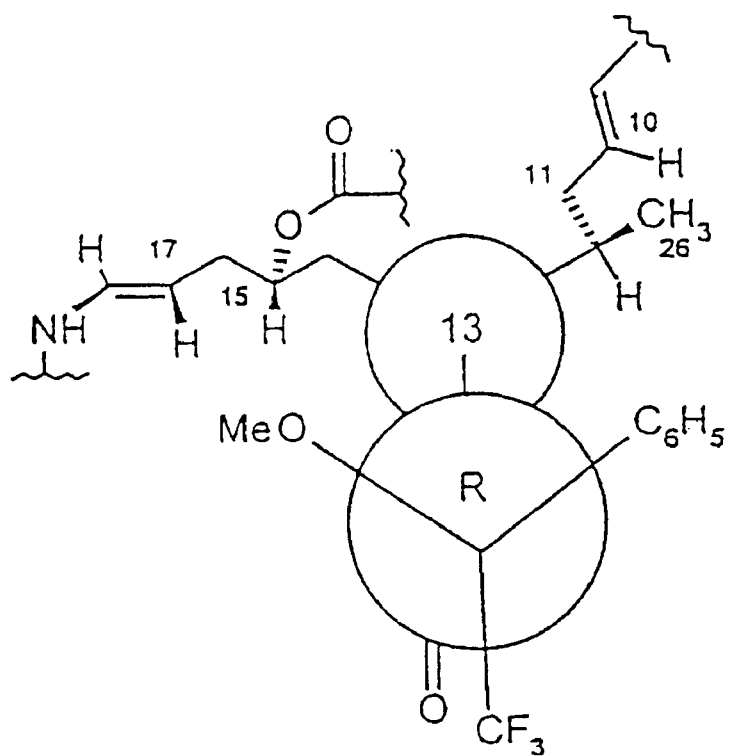
FIG. 8A illustrates a Newman projection depicting the partial structure of the (R)-Mosher derivative of salicylihalamide A.
Figure 8B:
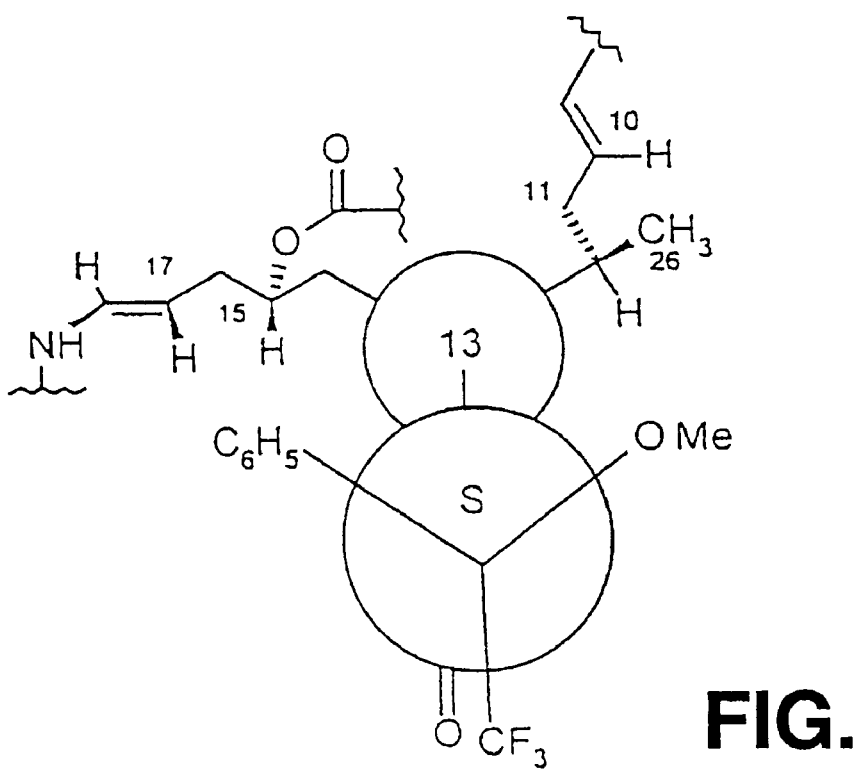
FIG. 8B illustrates a Newman projection depicting the partial structure of the (S)-Mosher derivative of salicylihalamide A.

Analysis of the Mosher ester NMR data was as follows. The C-12 methyl hydrogens (H-26) and H-10 of the (R)-derivative appeared upfield of those of the (S)-derivative in $C_6D_6$. Likewise, H-14a, H-15, and H-17 appeared downfield in the (R)-derivative relative to the (S)-derivative in $C_6D_6$ (FIGS. 8A and 8B, respectively). That the H-17 on the same face of the molecule as the Mosher ester site was evident from a strong nOe between H-17 and the ester methine, H-15. Similar results were observed in NMR spectra recorded in $CD_3OD$. These data allowed the absolute configuration at C-13 to be assigned as S. The partial structures shown in FIGS. 8A and 8B depict the Newman projections accounting for the observed chemical shift differences. In the (R,S)-diastereomer the H-10 and Me-26 hydrogens experience shielding from the phenyl group, while in the (S,S)-diastereomer H-14a, H-15, and H-17 experience shielding from the phenyl group. If C-13 were of (R)-configuration, just the opposite shielding results would be obtained. As the relative stereochemistry of all three chiral centers had been established, assignment of (S)-configuration at C-13 conferred the (R)-configuration at C-12 and C-15. The absolute configuration is therefore as depicted for salicylihalamide A in FIG. 4.

Accompanying salicylihalamide A in the sponge extract was a minor component whose spectral data were nearly identical to those of salicylihalamide A. Its structure was determined by careful comparison of $^1$H, $^{13}$C, and $^1$H—$^1$H COSY NMR data in both $C_6D_6$ and $CD_3OD$ with those of salicylihalamide A. The sequence of proton-carbon connectivities was identical to that of salicylihalamide A. The only significant difference between salicylihalamide A and its isomer, salicylihalamide B, was the coupling constant for H-17 and H-18, 10.2 Hz, compared to 14.6 Hz for salicylihalamide A. Thus, salicylihalamide B (FIG. 3C) was the 17-Z isomer of salicylihalamide A (FIG. 3A).

Lobatamide A (FIG. 3B), such as obtained and characterized spectroanalytically in Example 1, had a molecular formula of $C_{27}H_{33}N_2O_8$ as established by HRFABMS (noba, m/z 513.2257, MH$^+$, calcd 513.2237). The presence of 3 exchangeable protons was indicated by a CIMS deuterium exchange experiment using $ND_3$ as the ionizing agent. The $^{13}$C NMR spectrum of lobatamide A (Table 4) contained signals for all 27 carbons, including two ester carbonyls (δ 171.9, 170.0), an amide carbonyl (δ 164.2), 15 sp2 carbons (14 of which were accounted for by a phenyl ring and 4 olefins), 3 oxygenated methine carbons (δ 73.8, 73.3, 73.0), 3 methylenes (δ 33.1, 35.6, 38.9), and 3 methyl groups (δ 62.7 ($OCH_3$), 20.2, 19.6). The $^1$H and $^{13}$C NMR data for lobatamide A and lobatamide B are illustrated in Table 4 below. All spectra were recorded in $CD_3OD$ and referenced to residual methanol.

TABLE 4

| | A | | HMBC correl. | B | |
|---|---|---|---|---|---|
| atom # | $^{13}$C δ (mult.) | $^1$H δ (#H, mult., J Hz) | to C# | $^{13}$C δ (mult.) | $^1$H δ (#H, mult., J Hz) |
| 1 | 170.0(s) | | | 170.0(s) | |
| 2 | 122.3(s) | | | 122.3(s) | |

TABLE 4-continued

| atom # | A $^{13}C$ δ (mult.) | $^1H$ δ (#H, mult., J Hz) | HMBC correl. to C# | B $^{13}C$ δ (mult.) | $^1H$ δ (#H, mult., J Hz) |
|---|---|---|---|---|---|
| 3 | 156.7(s) | | | 156.7(s) | |
| 4 | 114.4(d) | 6.68 (1H, d, 7.8) | 2, 6 | 114.4(d) | 6.68 (1H, d, 7.8) |
| 5 | 131.8(d) | 7.14 (1H, t, 7.8) | 3, 7 | 131.8(d) | 7.14 (1H, t, 7.8) |
| 6 | 120.8(d) | 6.63 (1H, d, 7.8) | 2, 4, 8 | 120.9(d) | 6.63 (1H, d, 7.8) |
| 7 | 141.2(s) | | | 141.2(s) | |
| 8a | 33.1 (t) | 3.21 (1H, dd, 17.1, 8.3) | 2, 6, 7, 9, 10 | 33.1 (t) | 3.21 (1H, dd, 8.8, 18.1) |
| b | | 2.93 (1H, br d, 17.1) | | | 2.93 (1H, br d, 18.1) |
| 9 | 125.6(d) | 5.17 (1H, m) | 11, 25 | 125.6(d) | 5.17 (1H, m) |
| 10 | 139.4(s) | | | 139.4(s) | |
| 11 | 73.3(d) | 4.78 (1H, d, 8.8) | 9, 10, 12, 13 | 73.3(d) | 4.78 (1H, d, 8.8) |
| 12 | 135.0(d) | 5.66 (1H, dd, 15.1, 8.8) | 10, 11, 13 | 135.0(d) | 5.66 (1H, dd, 15.1, 8.8) |
| 13 | 132.7(d) | 5.50 (1H, dd, 15.1, 8.3) | 11, 12, 26 | 132.7(d) | 5.50 (1H, dd, 15.1, 8.3) |
| 14 | 73.8(d) | 5.23 (1H, dq, 8.3, 6.3) | 12, 15 | 73.8(d) | 5.23 (1H, dq, 8.3, 6.8) |
| 16 | 171.9(s) | | | 171.9(s) | |
| 17a | 38.9 (t) | 2.67 (1H, d, 16.6) | 16, 17 | 38.9 (t) | 2.67 (1H, dd, 16.6, 2.4) |
| b | | 2.59 (1H, dd, 16.6, 10.7) | | | 2.59 (1H, dd, 16.6, 10.7) |
| 18 | 73.0(d) | 5.58 (1H, m) | 1, 15, 19 | 73.0(d) | 5.58 (1H, m) |
| 19 | 35.6 (t) | 2.48 (2H, dd, 7.3, 6.3) | 16, 17, 19, 20 | 35.6 (t) | 2.48 (2H, br t, 6.8) |
| 20 | 109.9(d) | 5.34 (1H, dt, 14.2, 7.8) | 18, 20 | 110.2(d) | 5.34 (1H, m) |
| 21 | 126.9(d) | 6.82 (1H, d, 14.2) | 18, 19, 21 | 126.8(d) | 6.82 (1H, d, 14.2) |
| 23 | 164.2(s) | | | 164.0(s) | |
| 24 | 126.1(d) | 6.04 (1H, d, 11.7) | 21 | 127.9(d) | 6.05 (1H, d, 11.7) |
| 25 | 135.6(d) | 6.45 (1H, dd, 11.7, 11.2) | 21 | 127.5(d) | 7.04 (1H, dd, 11.7, 9.8) |
| 26 | 148.7(d) | 8.95 (1H, d, 11.2) | 23 | 144.4(d) | 8.36 (1H, d, 9.8) |
| 28 | 62.7(q) | 3.91 (3H, s) | | 62.6(q) | 3.91 (3H, s) |
| 29 | 19.6(q) | 1.79 (3H, s) | 9, 10, 11 | 19.6(q) | 1.79 (3H, d, 6.8) |
| 30 | 20.2(q) | 1.35 (3H, d, 6.3) | 13, 14 | 20.2(q) | 1.35 (3H, s) |

Figure 9:
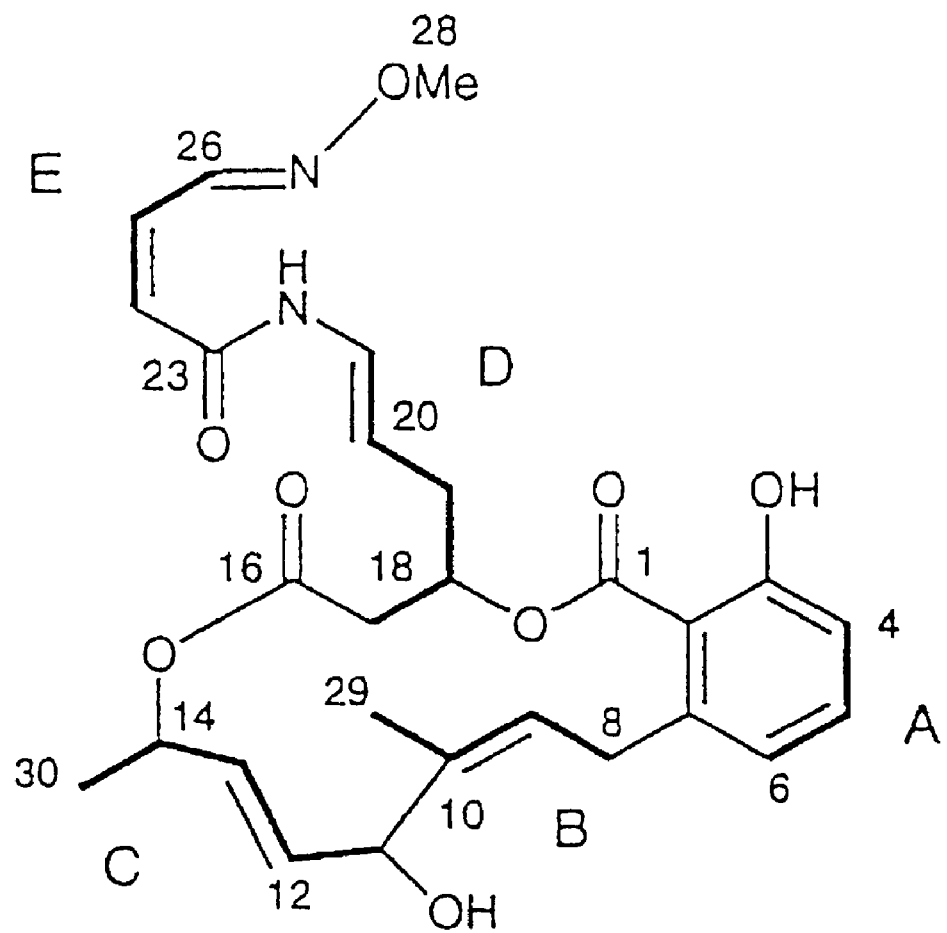
FIG. 9 illustrates the partial structures (shown in bold) as used in the structural analysis of lobatamide A.

A series of NMR experiments, including COSY, difference nOe, HMQC, and HMBC, was used to construct the five partial structures depicted in FIG. 9 by the emboldened bonds (designated as A–E in FIG. 9). Fragment A (FIG. 9) consisted of three adjacent aromatic protons ($δ_C$ 114.4, $δ_H$ 6.68, d, J=7.8 Hz; $δ_C$ 131.8, $δ_H$ 7.14, t, J=7.8 Hz; $δ_C$ 120.8, $δ_H$ 6.63, d, J=7.8 Hz). Fragment B (FIG. 9) consisted of a methylene group ($δ_C$ 33.1, $δ_H$ 2.93, dd, J=17.1, 8.3 Hz and $δ_H$ 3.21, d, J=17.1 Hz) and the olefinic proton of a trisubstituted olefin ($δ_C$ 125.6, $δ_H$ 5.17, m; $δ_C$ 139.4). An HMBC experiment indicated that the singlet methyl group ($δ_C$ 21.8, $δ_H$ 1.79) was a substituent on the olefinic carbon at 139.4 ppm which was also correlated to the olefinic proton at 5.17 ppm. The Z-geometry of this olefin was determined from the nOe observed between the methyl group (δ 1.79) and the proton at δ 5.17. Fragment C (FIG. 9) consisted of an oxygenated methine ($δ_C$ 73.3, $δ_H$ 4.78) coupled to an olefin ($δ_C$ 135.0, $δ_H$ 5.66 and $δ_C$ 132.7, $δ_H$ 5.50) designated as trans (E), based on the 15.1 Hz coupling observed between the olefinic protons. The proton at 5.50 ppm was further coupled to a proton residing on another oxygenated carbon ($δ_C$ 73.8, $δ_H$ 5.23), which was, in turn, coupled to the doublet methyl resonating at $δ_H$ 1.35 ($δ_C$ 20.2). Fragment D (FIG. 9) began with a diastereotopic methylene [$δ_C$ 38.9, $δ_H$ 2.67 & 2.59 (J=16.6 Hz)] coupled to an oxygenated methine ($δ_C$ 73.0, $δ_H$ 5.53). The methine was coupled to a methylene ($δ_C$ 35.6, $δ_H$ 2.48) which was, in turn, coupled to a second trans-olefin ($δ_C$ 109.9, $δ_H$ 5.34; $δ_C$ 126.9, $δ_H$ 6.82; J=14.2 Hz). The remaining spin system, labeled as fragment E in FIG. 9, consisted of 3 olefinic protons ($δ_C$ 126.1, $δ_H$ 6.04; $δ_C$ 135.6, $δ_H$ 6.45; and $δ_C$ 148.7, $δ_H$ 8.95). Two of these protons ($δ_H$ 6.04 and $δ_H$ 6.45, H24 and H25, respectively) formed a cis olefin based on the $J_{24,25}$ of 11.7 Hz and the observed nOe between the protons. Both the chemical shift of the carbon at 148.7 ppm and the downfield shift of its proton to 8.95 ppm suggested that this carbon was bonded to the remaining nitrogen atom in an imine-type bond. In addition, this proton was not correlated to any carbons except the neighboring olefin, already identified as part of fragment E. The carbon chemical shift of 148.7 was consistent with the presence of an oxime (Gordon et al., *J. Org. Chem.*, 49, 97–100 (1984)), and such a functional group accounted for the remaining nitrogen and oxygen atoms required by the molecular formula. The presence of a H25-H26 coupling constant near 11 Hz, plus the nOe correlations observed between those two protons, suggested that the olefin and oxime were in a s-cis relationship. These partial structures account for all of the structural elements of lobatamide A except for the methoxyl group. The methoxyl functionality was, in the end, placed on the oxime at N27 based on its carbon chemical shift ($δ_C$ 62.7), which was consistent with other oxime methyl ethers and supported by the weak nOe observed between the methoxyl signal at 3.91 ppm and the proton at 8.95 ppm (H26). The observed nOe and the chemical shifts of the oxime carbon and proton supported E (syn) geometry for the oxime double bond (Gordon et al., *J. Org. Chem.*, 49, 97–100 (1984); Wolkowski et al., *Tetrahedron Lett.*, 565–568 (1972)). The presence of an oxime methyl ether was also supported by MS data (vide infra).

The substitution pattern around the phenyl ring of fragment A (FIG. 9) was determined based on HMBC experiments optimized for 8.3 and 5.5 Hz couplings. The aromatic proton at δ 7.14 (H5), which was coupled to two ortho protons, was correlated to both a phenol carbon at δ 156.7, and a second, quaternary carbon at δ 141.2, suggesting that both were meta to this proton. The carbon at δ 141.2 was further correlated to the methylene protons at C8, thus identifying it as C7 and requiring attachment of that methylene to this carbon. Correlations to H6 (δ 6.63) were observed from δ 114.4 (C4), 122.3(C2) and the terminal carbon of the side chain (δ 33.1), placing the side chain ortho to C6 at C7. This left C2 (δ 122.3) as the only point of attachment for the ester carbonyl at δ 170.0 (C1).

Fragments A and B (FIG. 9) were connected through C7, based on HMBC correlations of that carbon to protons at δ 7.14 (H5), δ 6.63(H6), and δ 3.21 (H8a). Additional correlations supporting this connection were those between H6 and C8, H8 and C2, and H8 and C6. Correlations from C10 to H11 and H12, along with those observed to H29 from C9, C10, and C11, provided the connection between fragments B and C (FIG. 9). The correlation between H14 and the ester carbonyl at δ 171.9 (C16), which was further correlated to both protons on C17 (δ 2.59, 2.67), as well as H18, provided the connection between fragments C and D (FIG. 9). H18 (δ 5.58) was further correlated to the second ester carbonyl at δ 170.0(C1), which was previously linked to fragment A at C2 (FIG. 9). Finally, fragments D and E (FIG. 9) were linked through an amide bond based on the observed correlations between the carbonyl at δ 164.2 and protons at H21, H24, and H25. Thus, HMBC experiments provided the final data leading to the gross structure of lobatamide A (FIG. 3B).

Figure 10:
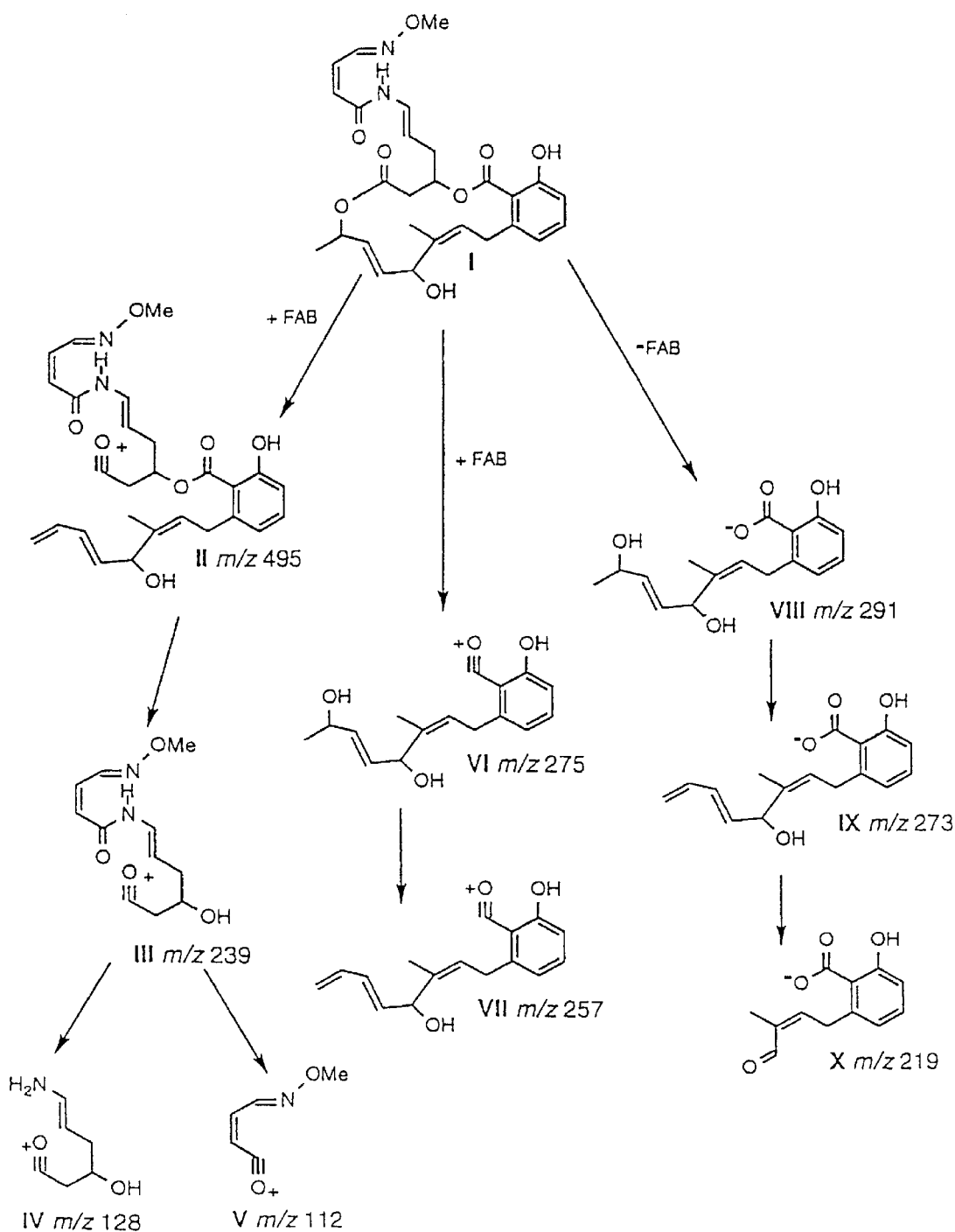
FIG. 10 illustrates the mass spectrometric fragmentation analysis for lobatamide A.
Figure 11A:
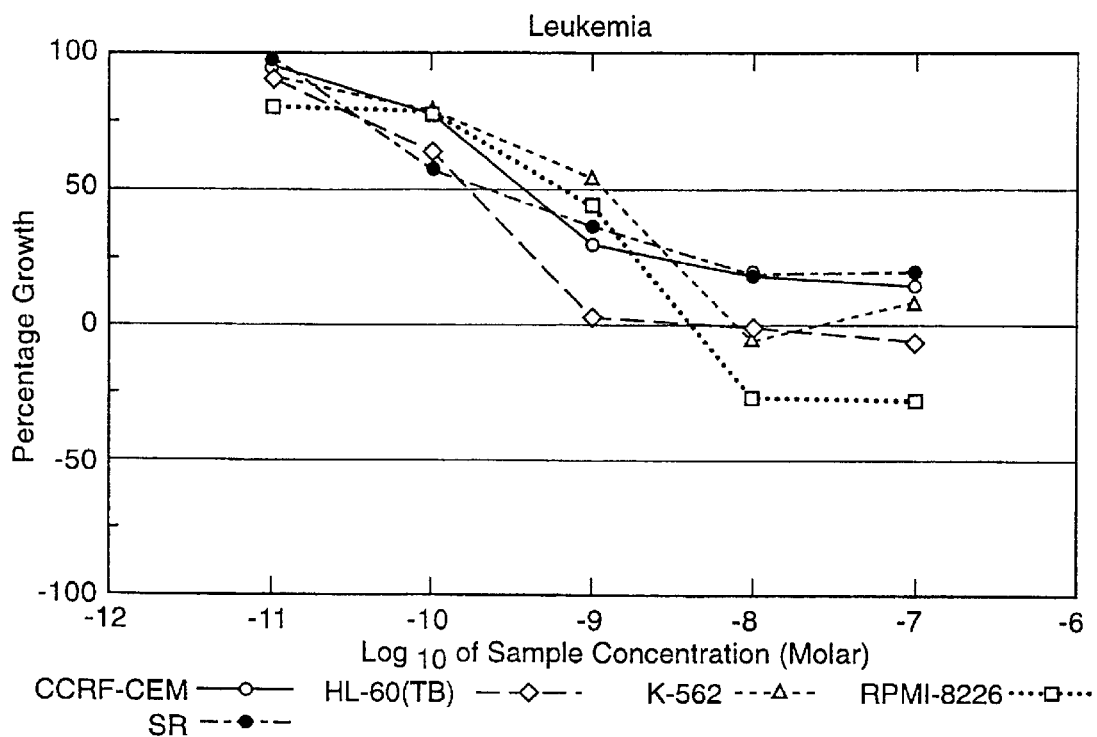
FIG. 11 illustrates exemplary concentration-response data for a single test of lobatamide A at a highest concentration limit of $10^{-7}$ M in the treatment of leukemia (FIG. 11A), non-small cell lung cancer (FIG. 11B), colon cancer (FIG. 11C), CNS cancer (FIG. 11D), melanoma (FIG. 11E), ovarian cancer (FIG. 11F), renal cancer (FIG. 11G), prostate cancer (FIG. 11H), and breast cancer (FIG. 11I).
Figure 11B:
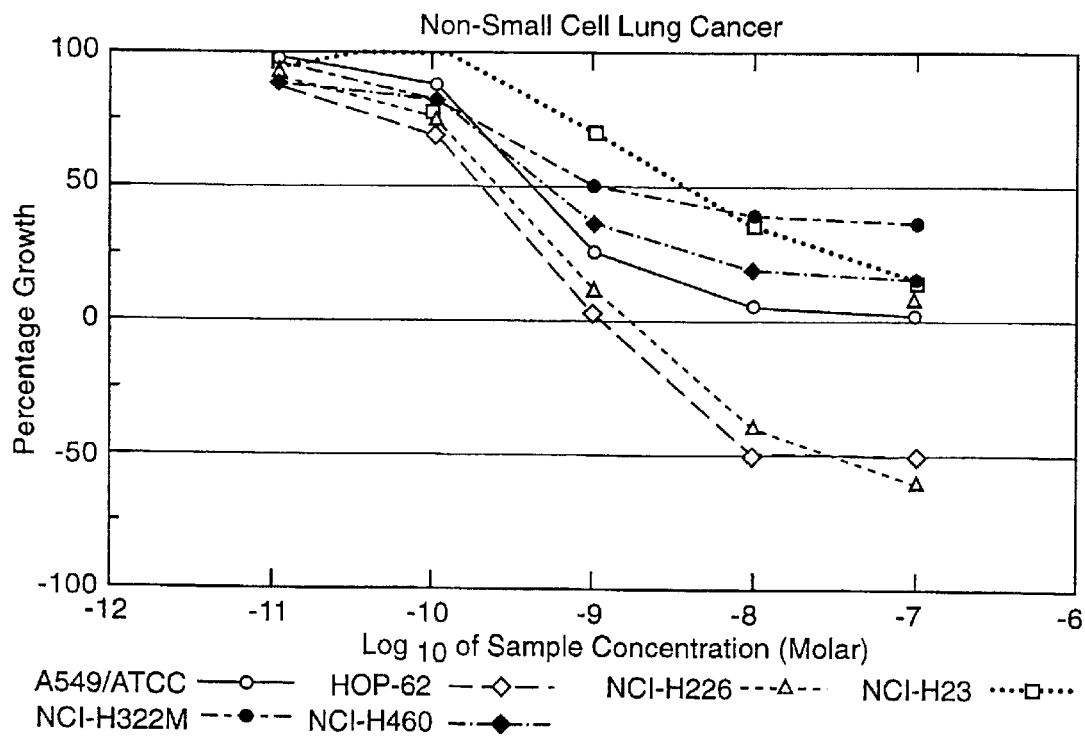
Figure 11C:
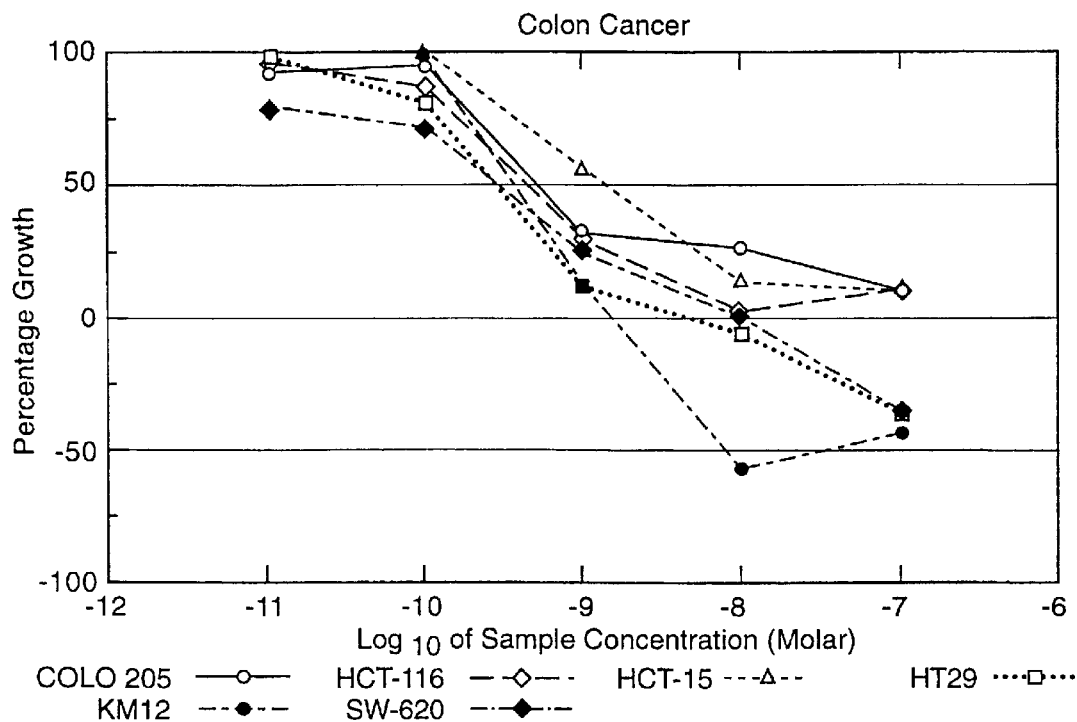
Figure 11D:
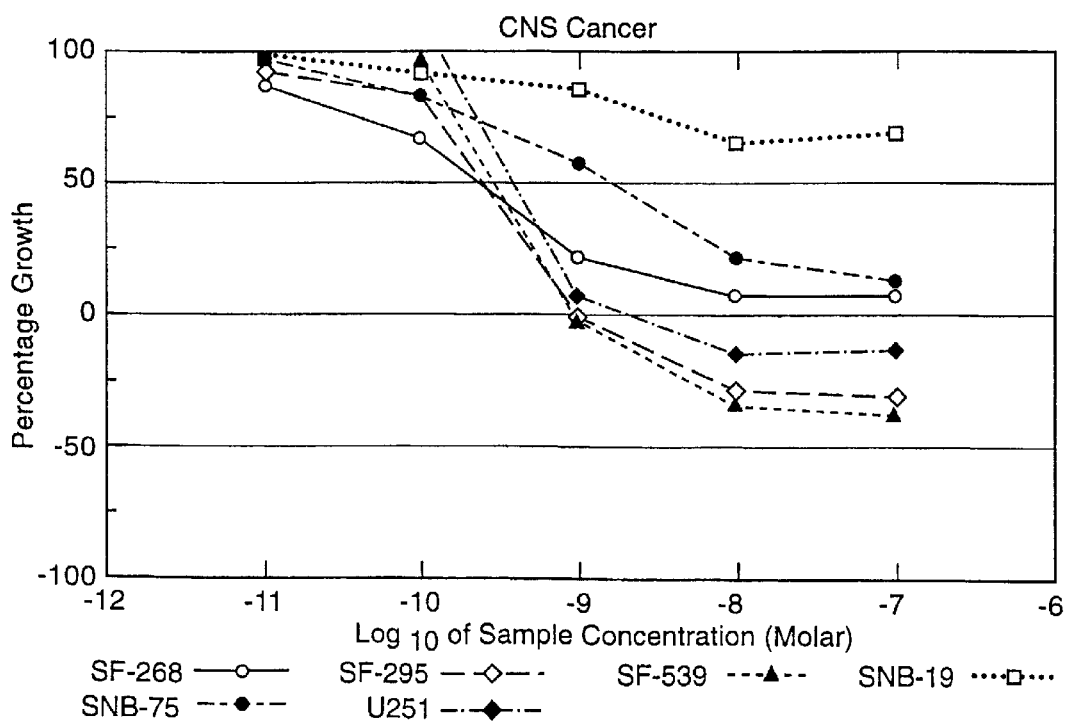
Figure 11E:
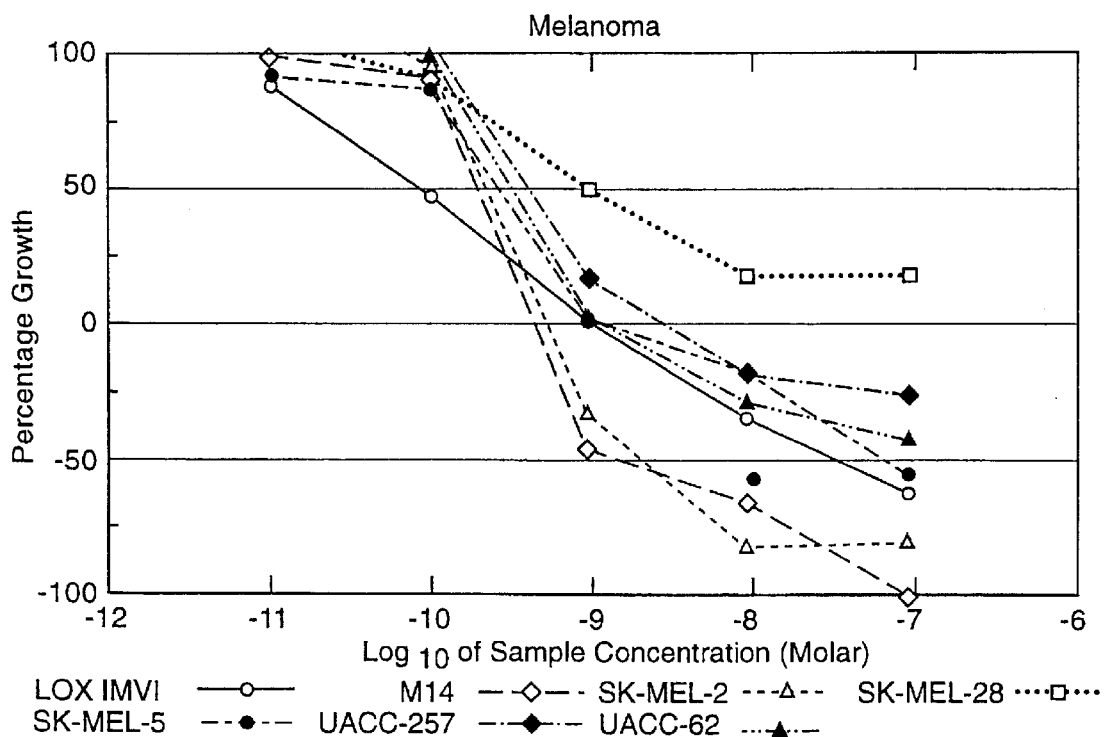
Figure 11F:
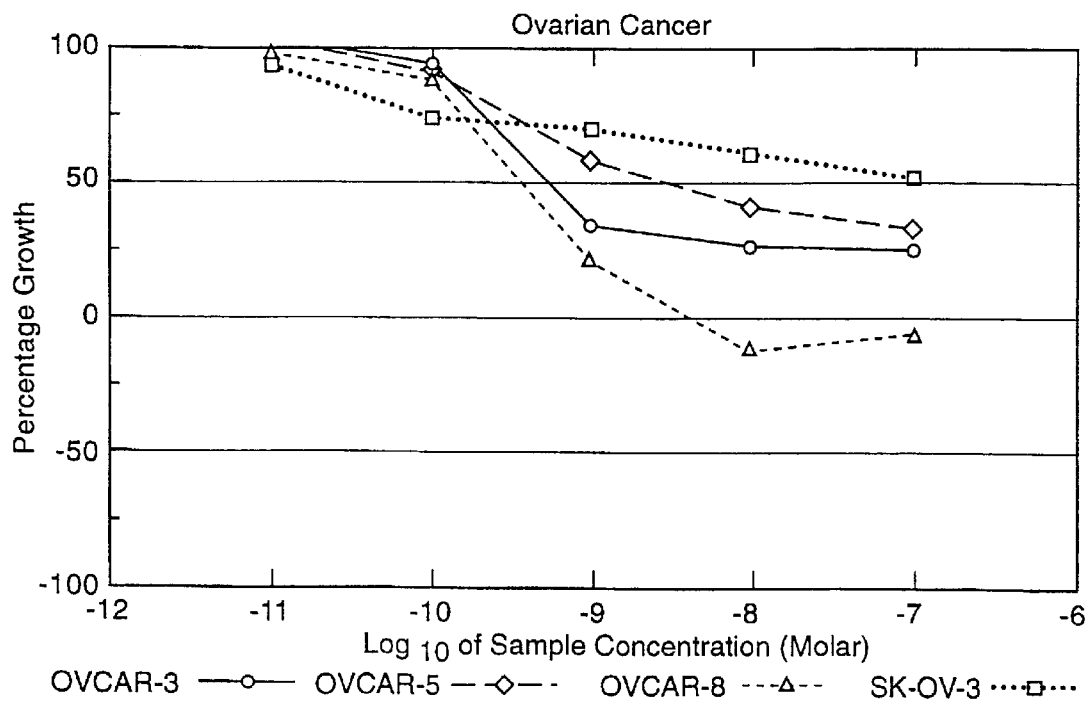
Figure 11G:
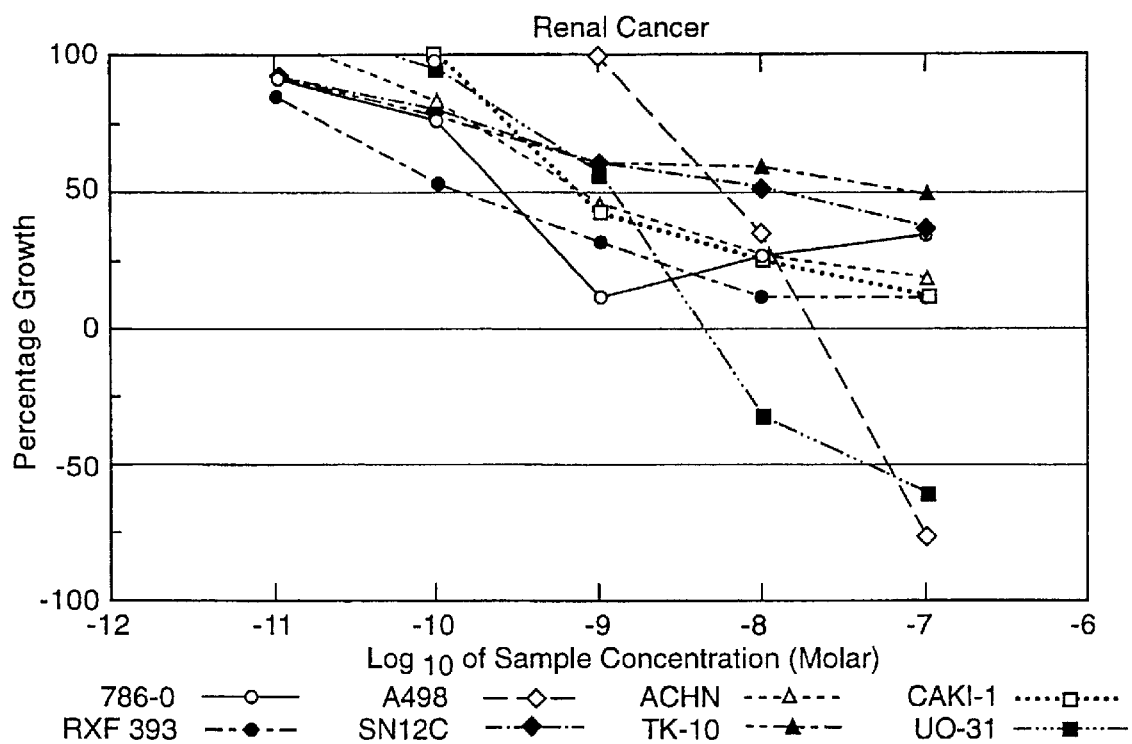
Figure 11H:
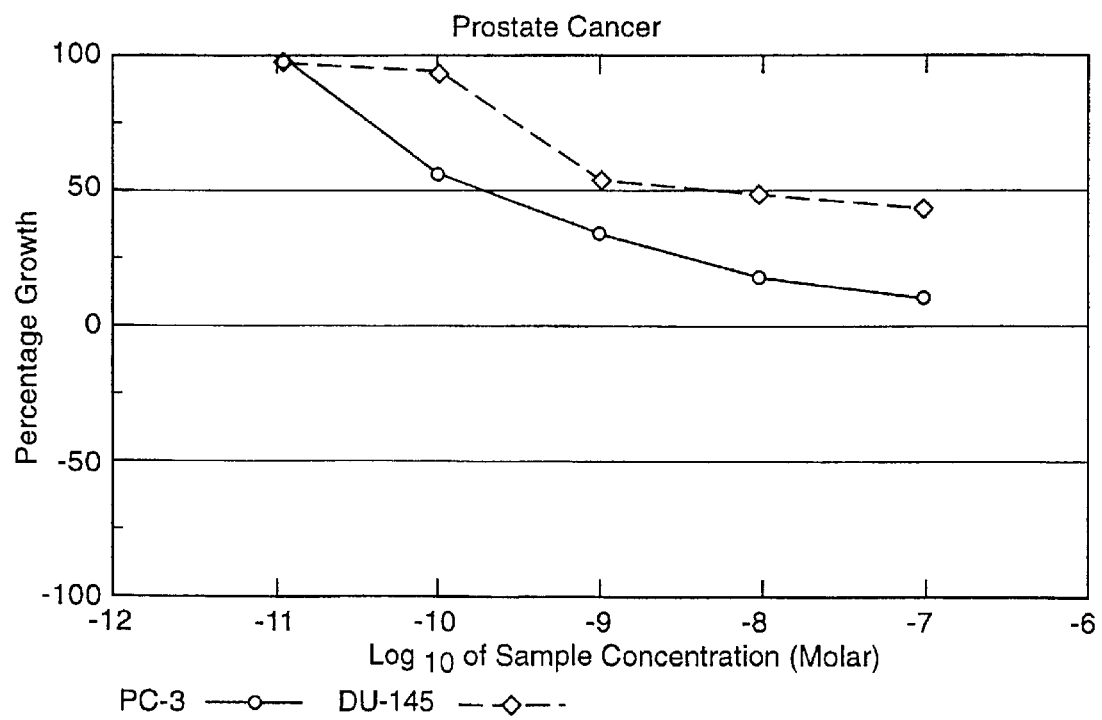
Figure 11I:
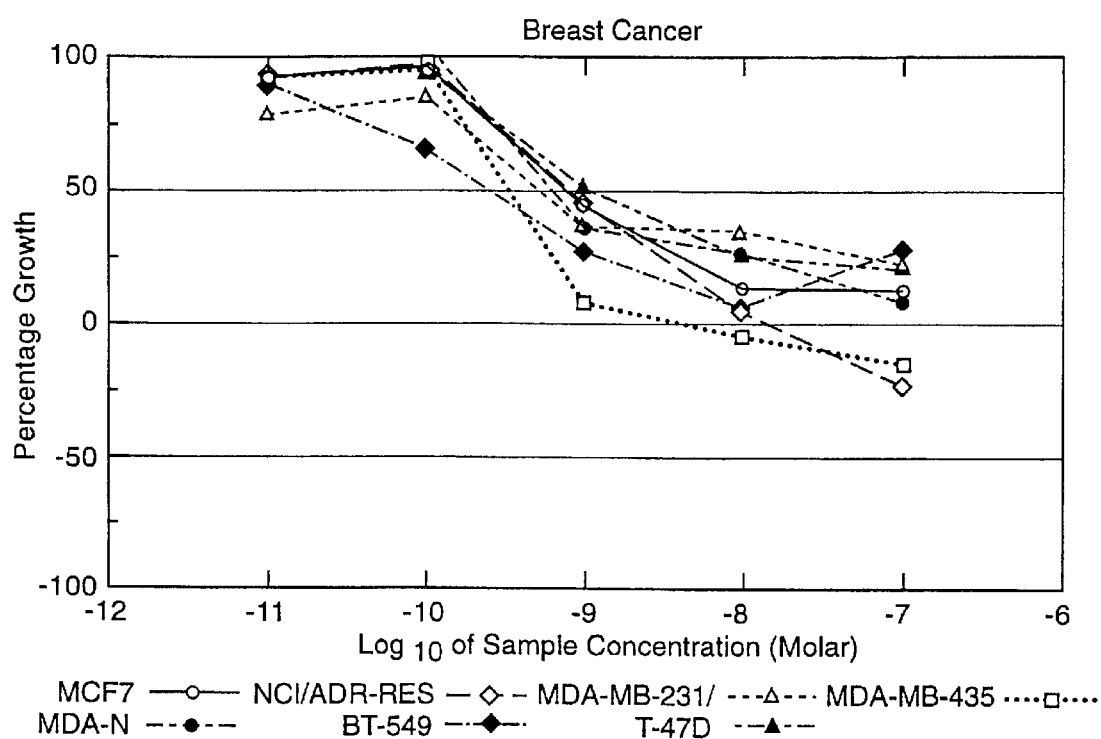
Figure 12A:
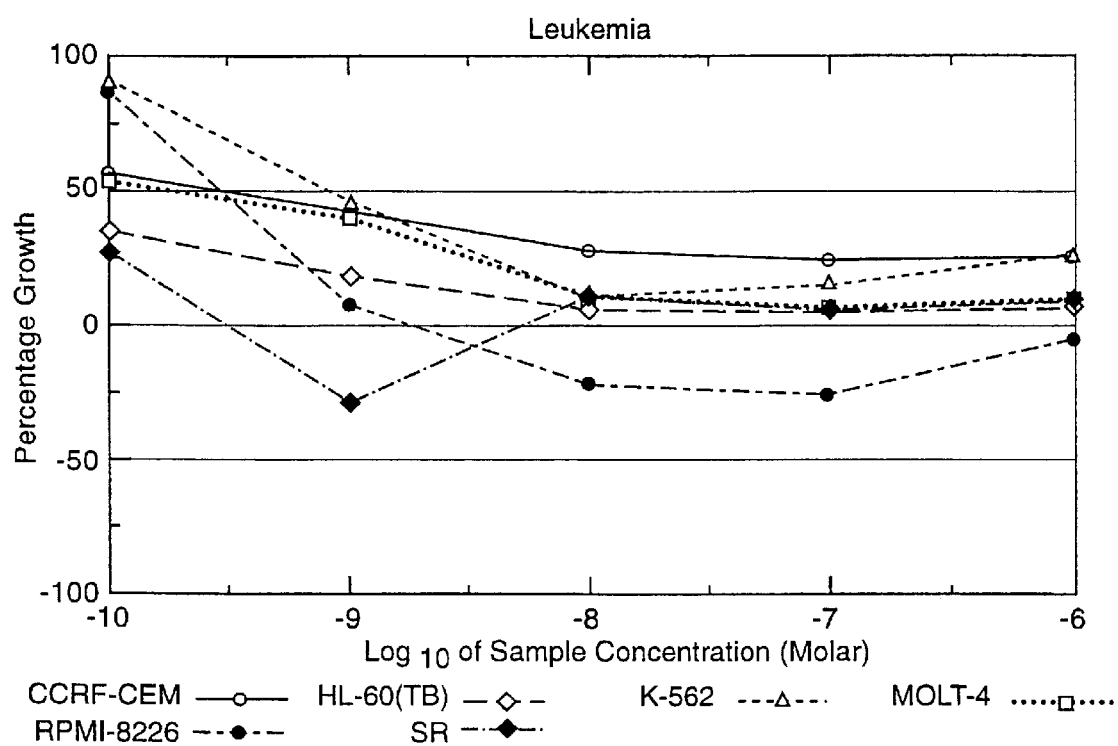
FIG. 12 illustrates the concentration-response curves obtained from testing of lobatamide A at a highest concentration limit of $10^{-6}$ M in the NCI 60 cell-line human tumor screen in the treatment of leukemia (FIG. 12A), non-small cell lung cancer (FIG. 12B), colon cancer (FIG. 12C), CNS cancer (FIG. 12D), melanoma (FIG. 12E), ovarian cancer (FIG. 12F), renal cancer (FIG. 12G), prostate cancer (FIG. 12H), and breast cancer (FIG. 12I).
Figure 12B:
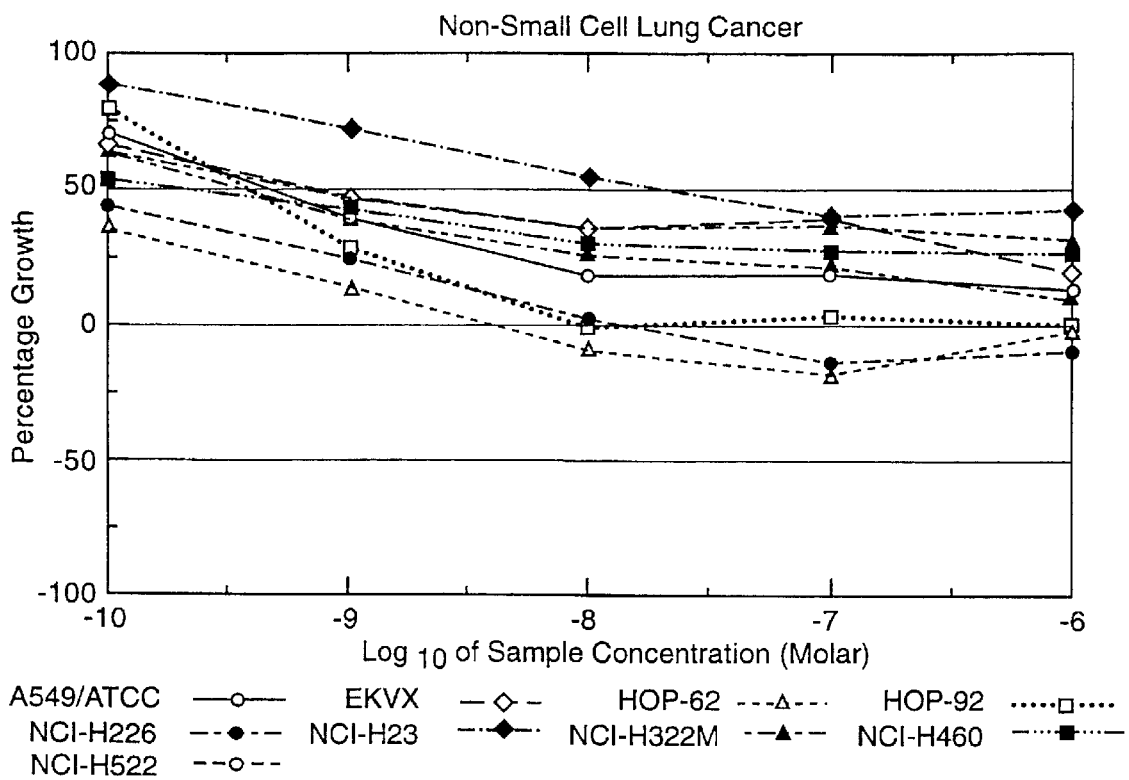
Figure 12C:
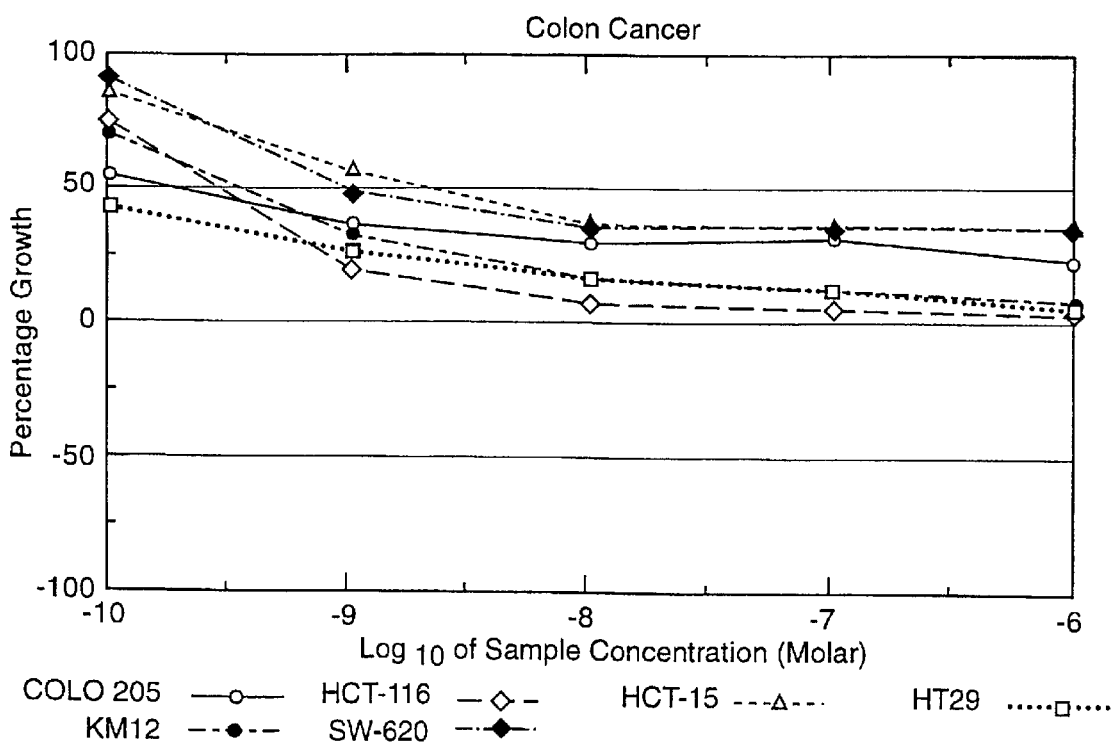
Figure 12D:
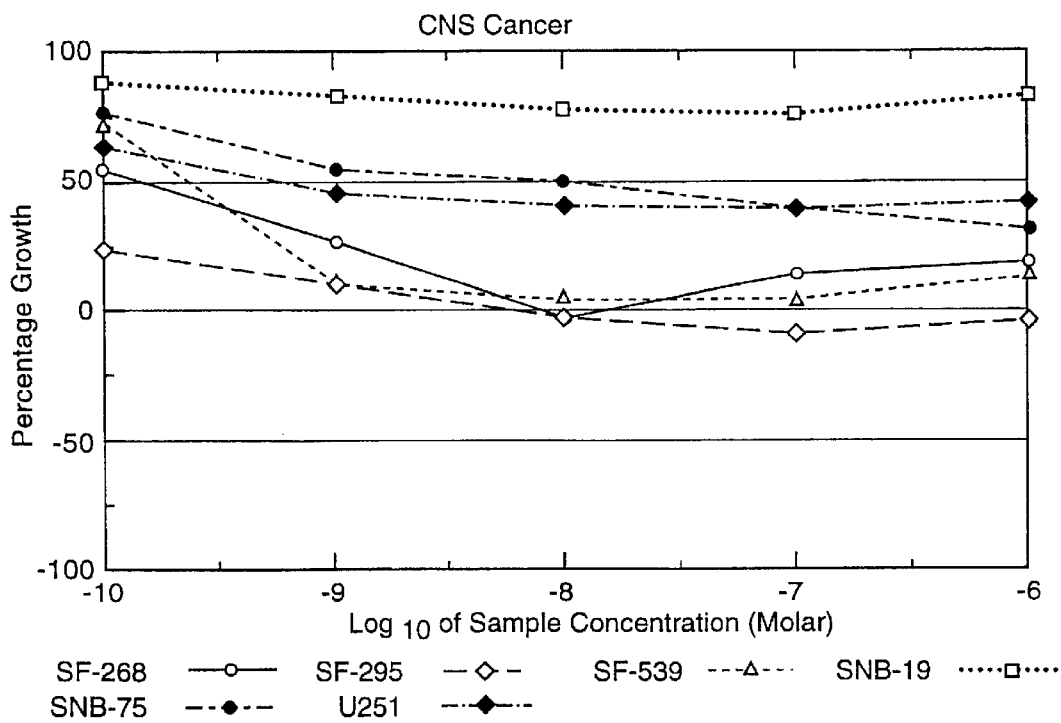
Figure 12E:
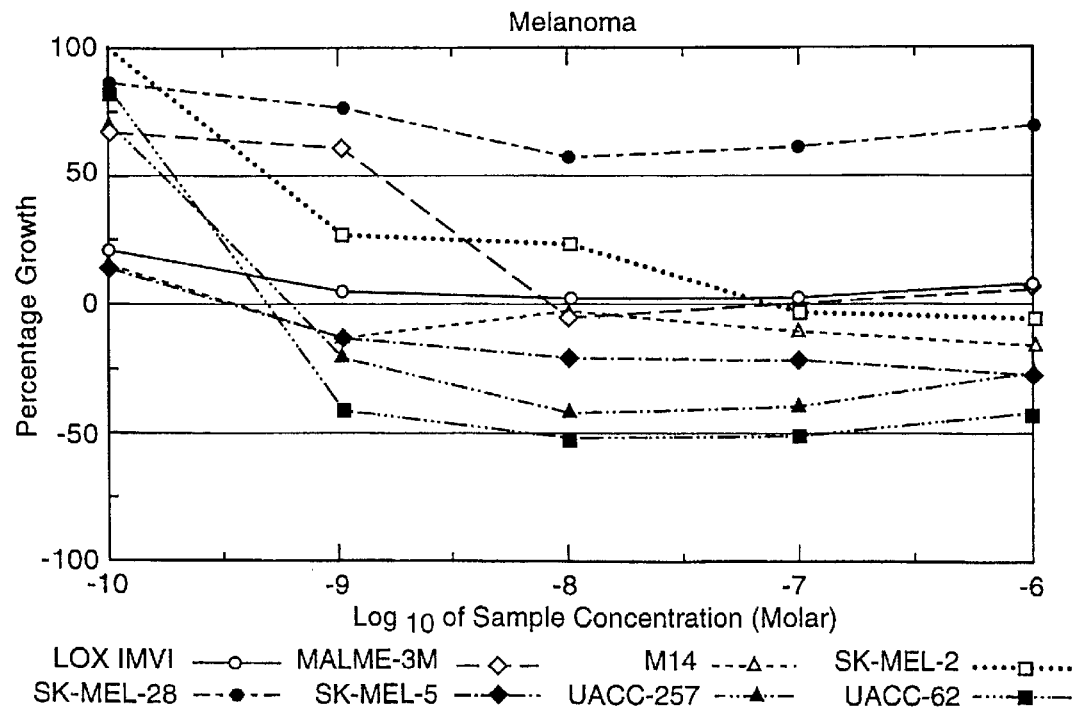
Figure 12F:
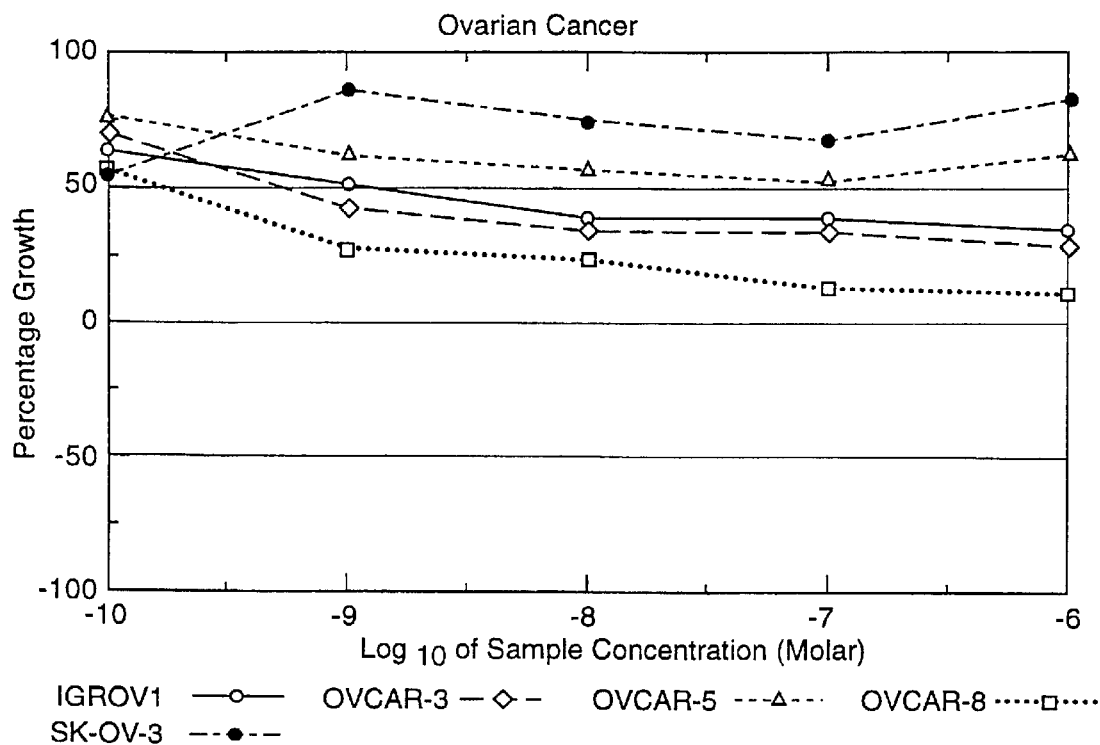
Figure 12G:
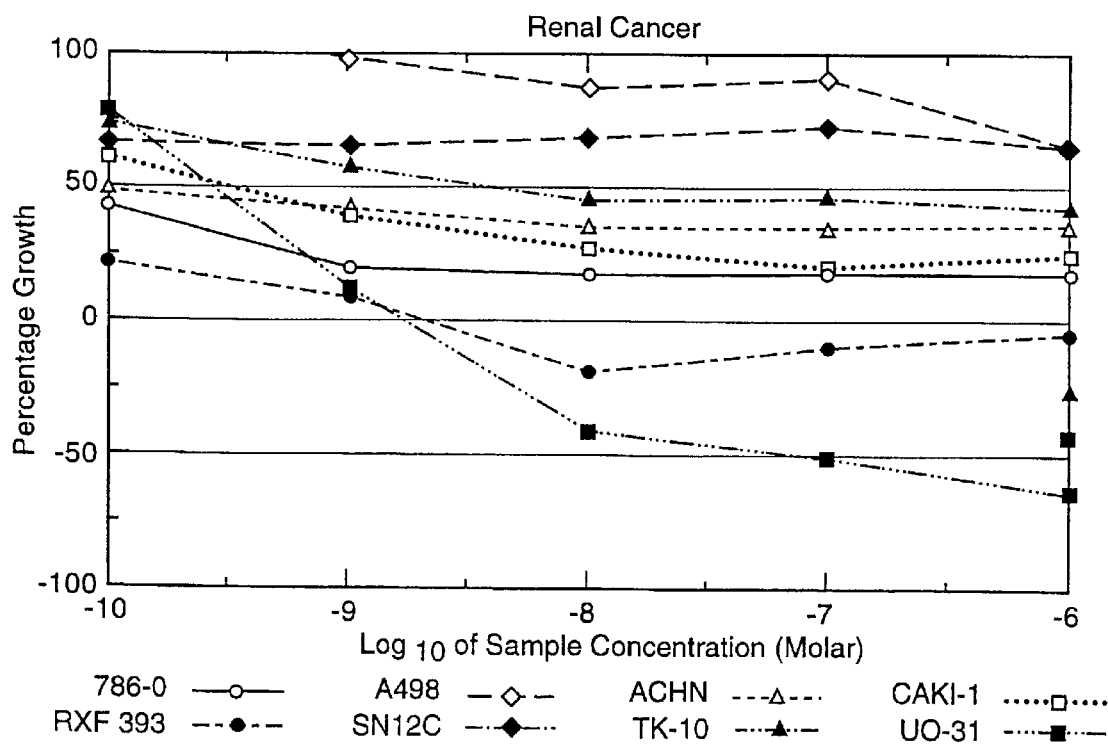
Figure 12H:
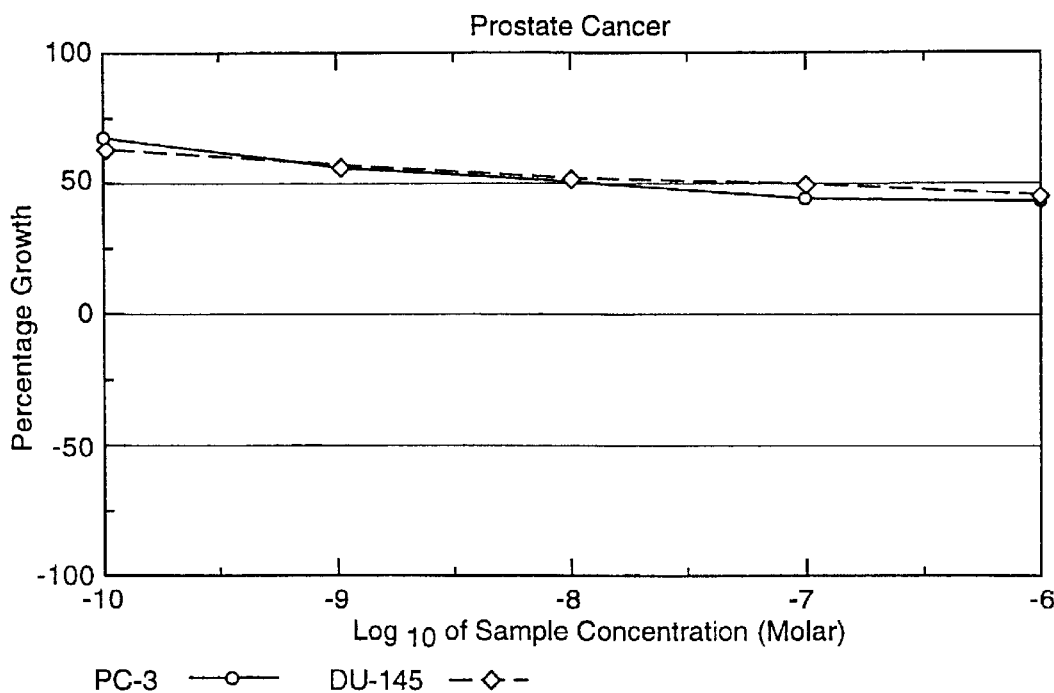
Figure 12I:
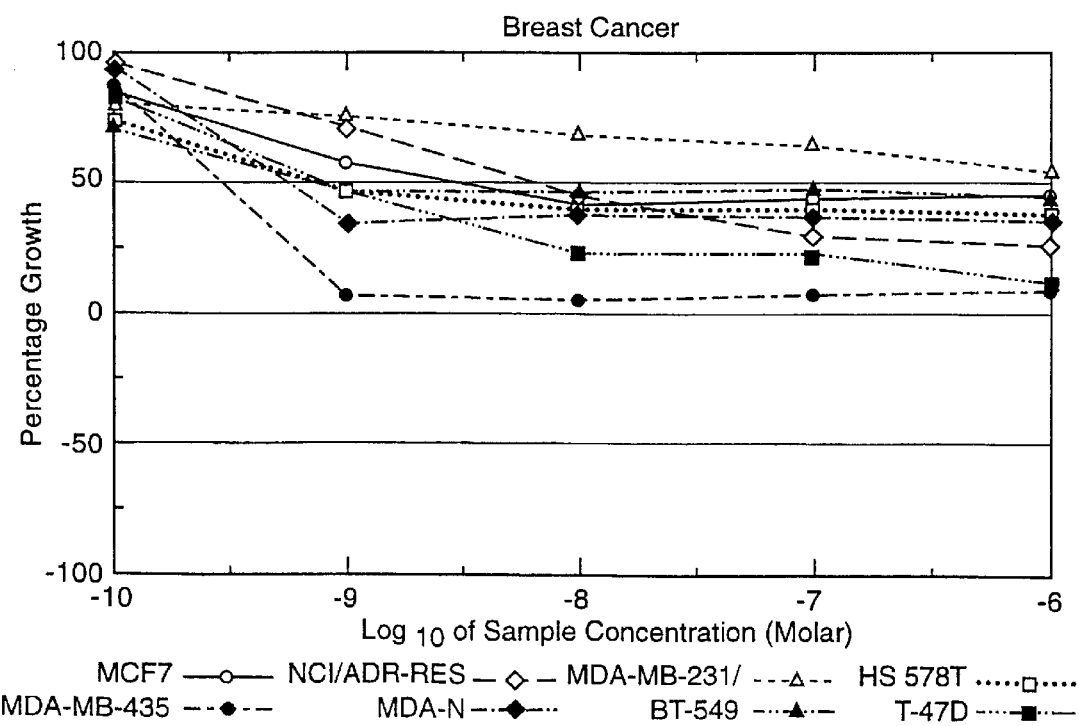

Additional, critical support for the structure of lobatamide A was provided by mass spectrometry (see methodology and data from Example 1). Deuterium exchange experiments provided results consistent with a structure with 3 exchangeable protons. Lobatamide A fragmented to give several structurally significant ions (FIG. 10), the sequence of which was determined by linked scan analyses of the fragment ions. In positive ion mode, elimination of a water molecule dominated the upper mass range to give a peak at m/z 495 (II). Although there is more than one structure that can be drawn for this ion, II is based on subsequent fragmentation and deuterium exchange data. Cleavage of the second ester bond yielded a dominant ion at m/z 239 (III) characteristic of the upper half of the molecule. This further fragmented to yield ions at m/z 128 (IV) and m/z 112 (V). This latter fragment (V, m/z 112) strongly supported location of the methoxyl on an oxime. Initial fragmentation at the other ester bond yielded fragment ions at m/z 275 (VI) and then m/z 257 (VII). In negative ion mode, fragmentation was dominated by cleavage at both ester bonds to yield ions at m/z 291 (VIII), m/z 273 (IX), and m/z 219 (X), further characterizing the macrocyclic ring. Upon acetylation, lobatamide A yielded a diacetate, m/z 596, which, on fragmentation in positive ion mode, gave further support to the lobatamide A structure (fragment ions comparable to II, VI, and VII showed two acetylations, while analogous structure III, IV and V showed no change).

Lobatamide B (FIG. 3D) was isomeric with lobatamide A. Indeed, the only significant difference in the $^1$H NMR spectrum of lobatamide B was the downfield shift of H25 to 7.04 ppm (vs. 6.45 ppm in lobatamide A) and the upfield shift of H26 to 8.36 ppm (vs. 8.95 ppm in lobatamide A). The upfield shift of this proton is consistent with Z (anti) geometry about the oxime bond. These shifts in the proton spectrum were accompanied by similar changes in the corresponding carbon signals, with C25 appearing at δ 127.5, upfield from 135.6 ppm in lobatamide A, and C26 moving upfield to 144.4 ppm (vs. δ 148.7 in lobatamide A). These differences indicated that the geometry of the oxime methyl ether was changed to Z in lobatamide B. No nOe was observed between the oxime OMe and H26, as was seen with lobatamide A. The mass spectrum of lobatamide B showed essentially the same fragmentations as those seen in lobatamide A, further supporting that only the geometry of the oxime had changed in lobatamide B.

EXAMPLE 3

This example illustrates the isolation and structure of additional compounds of the present invention, Lobatamides C–F.

Lobatamides C–F (FIGS. 3E–3H, respectively), were isolated from *Aplidium lobatum*, and the structures elucidated, according to procedures analogous to those described in Examples 1 and 2 for lobatamides A and B. Lobatamide C (FIG. 3E), was shown by HRFABMS to be isomeric with lobatamides A and B (FIGS. 3B and 3D, respectively), namely $C_{27}H_{32}N_2O_8$. As with the latter compounds, the presence of three exchangeable protons was indicated by a CIMS deuterium exchange experiment using $ND_3$ as the ionizing agent. The structural similarities among the three compounds were clearly evident from both the $^{13}$C and $^1$H NMR spectra (Tables 4–6). The $^{13}$C NMR spectrum of lobatamide C contained signals for all 27 carbons, including two ester carbonyls (δ 171.7, 169.9); an amide carbonyl (δ 164.1); 15 sp$^2$ carbons, fourteen of which were accounted for a phenyl ring and four olefins; three oxygenated methine carbons (δ 73.7, 73.2, 72.9); three methylenes (6 33.0, 35.5, 38.8); and three methyl groups (δ 62.7 (OCH$_3$), 20.2, 19.5).

Based on a standard series of one- and two-dimensional NMR experiments, which included HMQC and HMBC, the five spin systems illustrated in FIG. 9 (labeled as regions A–E) for lobatamide A could also be identified for lobatamide C. Of the five spin systems defined, only one system (FIG. 9, region E) was different from those found in lobatamides A and B. This system contained a trans olefin based on the 15.1 Hz coupling constant between H24 and H25. This coupling constant was 11.7 Hz for both lobatamides A and B. For lobatamide C, the configuration of the oxime methyl ether was assigned as E based on the carbon chemical shifts for C26 and C25 at δ$_C$ 149.3 and 135.5, respectively; in addition, the one bond $J_{CH}$ of C26 was 175 Hz.

Fragments A and B (FIG. 9, regions A and B, respectively) were connected through C7, based on HMBC correlations of that carbon to protons at δ7.14 (H5) and δ3.21 (H8a). Additional correlations supporting this connection were those between H6 and C8, and H8 and C2. Correlations from C10 to H11 and H12, along with those observed to H29 from C9, C10 and C11, provided the connection between fragments B and C (FIG. 9, regions B and C, respectively). The correlation between H14 and the ester carbonyl at δ 171.7 (Cl$_6$), which was further correlated to both protons on C17 (δ 2.60, 268), as well as H18, provided the connection between fragments C and D (FIG. 9, regions C and D, respectively). H18 (δ 5.60) was further correlated to the second ester carbonyl at δ 169.9 (C1), which was previously linked to fragment A at C2. Finally, fragments D and E (FIG. 9, regions D and E, respectively) were linked through an amide bond, based on the observed correlations between the carbonyl at δ 164.1 (C23) and H24 and H25. No correlation between H21 and C23 was observed in the HMBC experiments; however, the presence of the amide bond was supported by the similarities of both the $^1$H and $^{13}$C NMR spectra. Thus, HMBC experiments led to the gross structure of lobatamide C (FIG. 3E); furthermore, as with lobatamides A and B, the deduced structure for lobatamide C was further confirmed by linked scan mass spectrometry. In all three cases, the identification of the same molecular formula and observation of the same fragmentations (see FIG. 9) supported the three structures as geometric isomers.

The three additional isolated compounds, lobatamides D–F (FIGS. 3F–3H, respectively), all had a molecular formula of C27H$_{32}$N$_2$O$_9$, indicating the presence of one more oxygen than lobatamides A–C. Deuterium-exchange CIMS experiments confirmed that the extra oxygen could be accounted for by an additional hydroxyl group in the latter four compounds. The $^{13}$C and $^1$H NMR data (Tables 5 and 6, respectively) further revealed the structures of lobatamides D–F.

For lobatamide D, a standard set of one and two-dimensional NMR experiments was obtained to identify the five spin systems present; of these, four (regions A–C and E depicted in FIG. 9) were identical to those of lobatamide A. Fragment D (corresponding to region D of FIG. 9), however, terminated in a hydroxy methylene ($\delta_C$ 64.2; $\delta_H$ 3.70, dd, J=12.1, 7.8 Hz; 3.65, dd, J=12.1, 3.9 Hz) rather than a methyl group. Linked scan mass spectrometry studies of lobatamide D indicated that several of the fragment ions differed by 16 amu relative to those of lobatamides A–C. These ions included II (to m/z 511), VI (to m/z 291), VII (to m/z 273), VIII (to m/z 307), and IX (to m/z 289). In addition, fragment VII lost the elements of water to yield an ion at m/z 255, thus establishing the C30 location of the extra hydroxyl group in lobatamide D. The carbon and proton chemical shifts and JCH values closely matched those reported for lobatamide A, indicating that both compounds possessed the same geometries at the $\Delta^{24,25}$-olefin and the oxime bonds.

Comparison of the $^1$H and $^{13}$C NMR spectra obtained for lobatamides D and E suggested they differed only in the geometry of the oxime methyl ether functionality. The chemical shift for the oxime carbon (C26) in lobatamide E appeared upfield relative to that for lobatamide D (144.5 ppm and 148.7 ppm, respectively), as was that for C25 (127.6 and 135.9 ppm for lobatamides E and D, respectively). These differences in the carbon spectra were paralleled by an analogous upfield shift of the signal for H26 (8.36 ppm for lobatamide E relative to 8.95 ppm for lobatamide D). In addition, the one bond heteronuclear coupling constant for C26 in lobatamide E was 190 Hz. These data indicated that the oxime methyl ether was of Z-geometry, as was the case with lobatamide B. A comparison of the spectral data for lobatamides B and E showed a close correlation between the chemical shifts in both the $^1$H and $^{13}$C spectra, supporting the structure of lobatamide E.

A comparison of the $^1$H and $^{13}$C spectra and a series of NMR experiments confirmed the gross structure of lobatamide F. As with lobatamide C, the C24–C25 olefin had E geometry based on the 15.6 Hz coupling constant. The consistent coupling constant of 10 Hz between H25 and H26, as well as the NOE observed between the two protons, indicated that the olefin-oxime bonds were in an s-cis relationship. Finally, the carbon chemical shifts of C26 (149.4 ppm) and C25 (135.5 ppm) corresponded closely with those of lobatamides A, C and D, and were downfield of the C25 and C26 shifts of lobatamides B and E. In addition, the one bond heteronuclear coupling constant of 178 Hz was consistent with those of the other lobatamides possessing E-geometry at the oxime bond.

Additional physicochemical and spectroanalytical data for lobatamides C–F were as follows. Lobatamide C: $[\alpha]_D$–15.50 (c 0.113, MeOH); UV (MeOH) $\lambda_{max}$ 280 (log $\epsilon$4.04) nm; IR (film) $\upsilon_{max}$ 3590–3108 (br), 3067, 2975, 2933, 1733, 1656, 1616, 1584, 1467, 1451, 1354, 1267, 1215, 1175, 1113, 1042, 959, 790 cm$^{-1}$; HRFABMS (magic bullet) MNa$^+$m/z 535.2065, calcd. for $C_{27}H_{33}N_2O_8$ 513.2255; FABMS (m-bullet) m/z 551 (MNa$^+$, 55%), 535 (60), 495 (20), 257 (32), 239 (50), 193 (100). Lobatamide D: $[\alpha]_D$–35.0° (c 0.08, MeOH); UV (MeOH) $\lambda_{max}$ 281 (log $\epsilon$4.23) IR (film) $\upsilon_{max}$ 3593–3123 (br), 2924, 1738, 1650, 1607, 1529, 1464, 1450, 1269, 1218, 1168, 1117, 1042, 964, 755 cm$^{-1}$; HRFABMS (m-bullet) MH$^+$m/z 529.2164, calcd. for $C_{27}H_{33}N_2O_9$ 529.2186; FABMS (noba) m/z 551 (MNa$^+$, 100%), 529 (6), 511 (10), 239 (12). Lobatamide E: $[\alpha]_D$–26.7°(c 0.06, MeOH); UV (MeOH) $\lambda_{max}$ 282 (log $\epsilon$4.25) IR (film) $\upsilon_{max}$ 3591–3110 (br), 2924, 1734, 1652, 1539, 1269, 1046, 668 cm$^{-1}$; HRFABMS (m-bullet) MH$^+$m/z (529.2184), calcd. for $C_{27}H_{33}N_2O_9$ 529.2186; FABMS (glyc) m/z 551 (MNa$^+$, 5%), 511 (17), 239 (33), 217 (30), 112 (100). Lobatamide F: $[\alpha]_D$–19.20 (c 0.067, MeOH); UV (MeOH) $\lambda_{max}$ 280 (log $\epsilon$4.17) IR (film) $\upsilon_{max}$ 3591–3108 (br), 2912, 1737, 1657, 1607, 1525, 1481, 1268, 1214, 1167, 1114, 1042, 973, 755, 668 cm$^{-1}$; HRFABMS (noba) MNa$^+$ m/z 551.2015, calcd. for $C_{27}H_{33}N_2O_9$ 529.2186; FABMS (magic bullet) m/z 551 (MNa$^+$, 50), 511 (20), 301 (40), 239 (10), 112 (100).

The $^{13}$C NMR data (125 MHZ, CD$_3$OD) for Lobatamides A–F (FIGS. 3A and 3B) are illustrated below in Table 5. The $^1$H NMR Data (500 MHz, CD$_3$OD) for Lobatamides C–F (FIGS. 3E–3H, respectively) are illustrated below in Table 6.

TABLE 5

| C# | Lobatamide C | Lobatamide D | Lobatamide E | Lobatamide F |
|---|---|---|---|---|
| 1 | 169.9 | 169.9 | 170 | 170 |
| 2 | 122.2 | 122.3 | 122.3 | 122.2 |
| 3 | 156.6 | 156.6 | 156.7 | 156.6 |
| 4 | 114.2 | 114.4 | 114.4 | 114.4 |
| 5 | 131.7 | 131.9 | 131.9 | 131.9 |
| 6 | 120.8 | 120.8 | 120.9 | 120.9 |
| 7 | 141.1 | 141.2 | 141.2 | 141.2 |
| 8 | 33 | 33.1 | 33.1 | 33.1 |
| 9 | 125.5 | 125.7 | 125.7 | 125.7 |
| 10 | 139.4 | 139.4 | 139.4 | 139.4 |
| 11 | 73.2 | 73.4 | 73.4 | 73.4 |
| 12 | 134.9 | 137.6 | 137.6 | 137.4 |
| 13 | 132.6 | 128.1 | 128.1 | 128.2 |
| 14 | 73.7 | 78.4 | 78.1 | 78.4 |
| 16 | 171.7 | 172.1 | 172.1 | 172.1 |
| 17 | 38.8 | 38.9 | 38.9 | 38.9 |
| 18 | 72.9 | 73.1 | 73.1 | 73.1 |
| 19 | 35.5 | 35.6 | 35.6 | 35.6 |
| 20 | 110.2 | 109.8 | 110.2 | 110.2 |
| 21 | 126.9 | 126.9 | 126.9 | 126.9 |
| 23 | 164.1 | 164.3 | 164.2 | 164.2 |
| 24 | 130.2 | 126.1 | 127.9 | 130.2 |
| 25 | 135.5 | 135.9 | 127.6 | 135.5 |
| 26 | 149.3 | 148.7 | 144.5 | 149.4 |
| 28 | 62.7 | 62.7 | 62.6 | 62.8 |
| 29 | 19.5 | 19.6 | 19.7 | 19.7 |
| 30 | 20.2 | 64.2 | 64.2 | 64.2 |

TABLE 6

| C# | Lobatamide C $^1$H (mult., J Hz) | Lobatamide D $^1$H (mult., J Hz) | Lobatamide E $^1$H (mult., J Hz) | Lobatamide F 1H (mult., J Hz) |
|---|---|---|---|---|
| 2 | 6.68 (d, 8.3) | 6.68 (d, 7.8) | 6.68 (d, 8.3) | 6.68 (d, 7.8) |
| 5 | 7.14 (dd, 7.8, 8.3)[a] | 7.14 (dd, 7.8, 7.8) | 7.14 (dd, 7.8, 8.3) | 7.14 (dd, 7.3, 7.8)[b] |
| 6 | 6.63 (d, 7.8) | 6.63 (d, 7.8) | 6.63 (d, 7.8) | 6.63 (d, 7.3) |
| 8a | 3.21 (dd, 8.8, 17.6) | 3.25 (dd, 8.8, 17.1) | 3.25 (dd, 9.3, 17.6) | 3.21 (dd, 8.8, 17.6) |
| b | 2.95 (br d, 17.6) | 2.96 (br d, 17.1) | 2.95 (br d, 17.6) | 2.95 (br d, 17.6) |
| 9 | 5.17 (m) | 5.20 (m) | 5.18 (m) | 5.17 (m) |
| 11 | 4.79 (d, 8.8) | 4.80 (d, 8.3) | 4.79 (d, 8.8) | 4.79 (d, 8.8) |
| 2 | 5.67 (dd, 8.8, 15.1) | 5.76 (dd, 6.6, 15.6) | 5.75 (dd, 8.8, 15.1) | 5.78 (dd, 8.8, 15.6) |

TABLE 6-continued

| C# | Lobatamide C<br>$^1$H (mult., J Hz) | Lobatamide D<br>$^1$H (mult., J Hz) | Lobatamide E<br>$^1$H (mult., J Hz) | Lobatamide F<br>1H (mult., J Hz) |
|---|---|---|---|---|
| 13 | 5.50 (dd, 8.8, 15.1) | 5.48 (dd, 9.3, 15.6) | 5.50 (dd, 9.3, 15.1) | 5.50 (dd, 8.8, 15.6) |
| 14 | 5.23 (dq, 8.8, 6.4) | 5.16 (m) | 5.16 (m) | 5.14 (m) |
| 17a | 2.68 (dd, 2.4, 16.6) | 2.73 (dd, 2.0, 16.6) | 2.73 (dd, 2.4, 16.6) | 2.73 (dd, 2.4, 16.6) |
| b | 2.60 (dd, 10.8, 16.6) | 2.67 (dd, 10.7, 17.1) | 2.67 (dd, 10.2, 16.6) | 2.67 (dd, 10.7, 16.6) |
| 18 | 5.60 (m) | 5.58 (m) | 5.60 (m) | 5.61 (m) |
| 19 | 2.48 (2H, m) | 2.48 (2H, br t, 6.8) | 2.48 (2H, br t, 6.8) | 2.48 (2H, br t, 6.8) |
| 20 | 5.37 (dt, 7.8, 14.6) | 5.34 (dt, 7.8, 14.2) | 5.35 (dt, 7.3, 14.2) | 5.37 (dt, 7.3, 14.2) |
| 21 | 6.87 (d, 14.6) | 6.82 (d, 14.6) | 6.83 (d, 14.2) | 6.87 (d, 14.2) |
| 24 | 6.28 (d, 15.1) | 6.05 (d, 11.2) | 6.05 (d, 11.7) | 6.28 (d, 15.6) |
| 25 | 7.14 (dd, 10.2, 15.1)$^a$ | 6.49 (dd, 10.2, 11.2) | 7.03 (dd, 9.8, 11.7) | 7.13 (dd, 9.8, 15.6)$^b$ |
| 26 | 7.86 (d, 10.2) | 8.95 (d, 10.2) | 8.36 (d, 9.8) | 7.85 (d, 9.8) |
| 28 | 3.91 (3H, s) | 3.89 (3H, s) | 3.89 (3H, s) | 3.91 (3H, s) |
| 29 | 1.79 (3H, s) | 1.79 (3H, s) | 1.80 (3H, s) | 1.78 (3H, s) |
| 30a | 1.34 (3H, d, 6.3) | 3.70 (dd, 7.8, 12.1) | 3.70 (dd, 7.3, 12.2) | 3.70 (dd, 7.3, 11.7) |
| b |  | 3.65 (dd, 3.9, 12.1) | 3.65 (dd, 3.9, 12.2) | 3.65 (dd, 3.9, 11.7) |

$^{a,b}$overlapping multiplets

EXAMPLE 4

This example illustrates the anticancer activity profile of compounds of the present invention, in particular, salicylihalamide A and lobatamide A (FIGS. 3A and 3B, respectively). Compounds were tested in the NCI 60 cell-line screen as described in detail in Boyd and Paull, *Drug Dev. Res.*, 34, 91–109 (1995); and Monks et al., *J. Natl. Cancer Inst.*, 83, 757–766 (1991). Briefly, stock solutions of the compounds were prepared initially in dimethylsulfoxide at 400× the desired final highest test concentrations and stored at −70° C. until use. The final highest test concentrations studied in this example varied between $10^{-5}$ and $10^{-8}$ molar. At the time of screening, an aliquot of the thawed stock was diluted with complete medium containing 50 μg/ml gentamycin to give a concentration of 2× the desired final highest test concentration. An additional four, 10-fold serial dilutions were then made to provide a total of five concentrations, spanning a 4-$\log_{10}$ concentration range. One hundred μl aliquots of these intermediate dilutions were immediately added to the appropriate microtitre wells, each already containing the appropriate numbers and types of cells in 100 μl of culture medium, resulting in the desired five final concentrations.

The 60 cell lines used, and the respective inoculation densities, were as described in Boyd and Paull, *Drug Dev. Res.*, 34, 91–109 (1995), and Monks et al., *J. Natl. Cancer Inst.*, 83, 757–766 (1991). Following the compound additions, the plates were incubated for 48 h at 37° C. under a 5% $CO_2$/air atmosphere and 100% humidity. Then, adherent cells (all lines except the leukemia) were fixed in situ by gentle addition of cold trichloroacetic acid (50 μl of 50% w/v) and incubated for 60 min at 4° C. Supernatants were discarded, and plates were washed five times with deionized water and air dried. Sulforhodamine B solution (SRB; 100 μl at 0.4% w/v in 1% acetic acid) was added to each plate, followed by further incubation for 10 min at room temperature. Excess unbound dye was then removed by washing five times with 1% acetic acid, followed by air drying. The bound stain in each well was solubilized by addition of 100 μl of 10 mM unbuffered Tris base; this was followed by a determination of optical densities (515 nm) on an automated plate reader. For suspension cell cultures (the leukemias), the method was the same except that at the end of the drug incubation period the settled cells were fixed in situ to the bottoms of the microtitre wells by gentle addition of 50 μl of 80% trichloracetic acid. Appropriate control wells were included in the test plate format (Monks et al., *J. Natl. Cancer Inst.*, 83, 757–766 (1991)) to allow subtraction of background optical densities, drug-blank corrections, and a determination of cell densities at time 0 (the time at which compounds are added).

The quadruplicate testing of pure salicylihalamide A in the NCI 60 cell-line screen gave the following averaged, individual negative $\log_{10}$ $GI_{50}$ values shown along with the respective subpanel and cell-line identifiers: (Leukemia) CCRF–CEM (7.89), HL-60-TB (9.04), K-562 (8.41), MOLT-4 (7.96), RPMI-8226 (7.89), SR (8.44); (Lung) A549/ATCC (8.54), EKVX (7.52), HOP-62 (8.38), HOP-92 (7.77), NCI-H226 (8.80), NCI-H23 (6.55), NCI-H322M (6.72), NCI-H460 (9.01), NCI-H522 (7.26); [Colon] COLO 205 (8.07), HCC-2998 (6.74), HCT-116 (8.74), HCT-15 (8.44), HT29 (8.54), KM12 (8.30), SW-620 (7.54); (Brain) SF-268 (7.55), SF-295 (8.96), SF-539 (7.89), SNB-19 (6.47), SNB-75 (6.21), U251 (7.57); (Melanoma) LOX-IMVI (9.11), MALME-3M (7.62), M14 (8.92), SK-MEL-2 (7.47), SK-MEL-28 (7.00), SK-MEL-5 (9.00), UACC-257 (8.47), UACC-62 (8.38); (Ovary) IGROVI (7.89), OVCAR-3 (7.03), OVCAR-4 (5.30), OVCAR-5 (8.11), OVCAR-8 (8.43), SK-OV-3 (5.54); (Kidney) 786–0 (7.92), A498 (6.55), ACHN (8.01), CAKI-1 (8.96), RXF-393 (9.07), SN-12C (7.77), TK-10 (5.74), UO-31 (8.31); (Prostate) PC-3 (7.51), DU-145 (8.26); [Breast] MCF-7 (7.12), MCF-7-ADR-RES (8.07), MDA-MB- 231/ATCC (6.92), HS-578T (5.85), MDA-MB-435 (7.82), MDA-N (8.00), BT-549 (9.30), T-47D (8.34).

$GI_{50}$ and TGI-COMPARE analyses of the full data set obtained from the screening of salicylihalamide A revealed that the compound gave a striking pattern of differential cytotoxicity in the NCI 60 cell-line screen that is characteristic of the compounds of the present invention (e.g., Pearson correlation coefficients greater than or equal to 0.7–0.8 with lobatamides A and B) but unlike that of any known conventional anticancer drug class. COMPARE pattern-recognition analyses of the mean graph profile of salicylihalamide A did not reveal any significant correlation to the profiles of known anticancer compounds contained in the NCI's standard agents database. The mean panel $GI_{50}$ con centration of salicylihalamide A was approximately 15 nM, and the range of differential sensitivity among the 60 cell-lines comprising the NCI panel was greater than or equal to $10^3$.

Similarly, the triplicate testing of lobatamides A and B in the NCI 60 cell-line screen yielded mean-graph profiles highly correlated with each other (e.g., TGI-COMPARE Pearson correlation coefficients greater than or equal to 0.9) and highly characteristic of compounds of the present invention (e.g., TGI-COMPARE Pearson correlation coefficients with salicylihalamide A of greater than or equal to 0.7–0.8). FIGS. 11A–11I graphically depict a representative set of concentration-response data for a single test of lobatamide A at a highest concentration limit of $10^{-7}$ M. FIGS. 12A–12I graphically depict a representative set of concentration-response data from a single test of lobatamide A at a highest concentration limit of $10^{-6}$ M.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

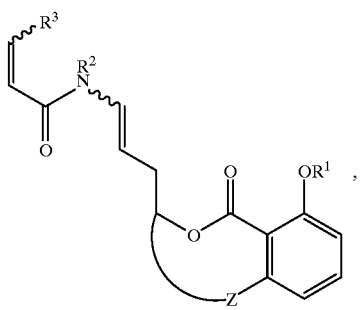

(I)

wherein $R^1$ and $R^2$ are the same or different and are independently H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated alkyl, or aryl; $R^3$ is H, $C_1$–$C_6$ straight-chain or branched saturated or unsaturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms which, together with the five atoms beginning with the carbon of the aromatic ring in meta-relationship with $OR^1$ and ending with the carbon directly attached to the alkyl oxygen of the lactone, said carbons being covalently bonded to either end of linker Z, integrally form a 12–15 membered ring; or a pharmaceutically acceptable salt, an ester, or a prodrug thereof; with the proviso that when Z is a contiguous linker comprising a chain of 10 atoms, $R^3$ is not an oxime methyl ether.

2. The compound of claim 1 selected from the group consisting of:

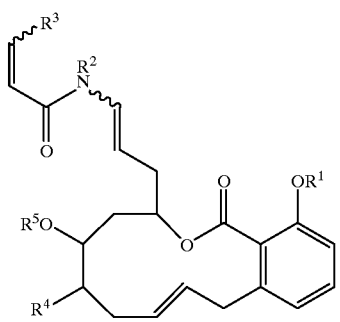

(IA)

and

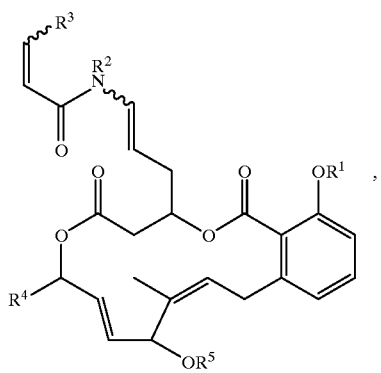

(IB)

wherein $R^1$–$R^3$ are as defined in claim 1; $R^4$ is H, $C_1$–$C_6$ alkyl, or $R^7CH_2$—, wherein $R^7$ is $R^6O$—, $R^6CO_2$—, or $R^6SO_3$—; and $R^5$ is H, $C_1$–$C_6$ straight-chain or branched saturated or unsaturated alkyl, aryl, $R^6CH_2$—, $R^6CO$—, or $R^6SO_3$—, wherein $R^6$ is H, $C_1$–$C_6$ straight-chain or branched saturated or unsaturated alkyl, or aryl; or a pharmaceutically acceptable salt, an ester, or a prodrug thereof; with the proviso that when said compound is of formula (IB), $R^3$ is not an oxime methyl ether.

3. The compound of claim 2 selected from the group consisting of:

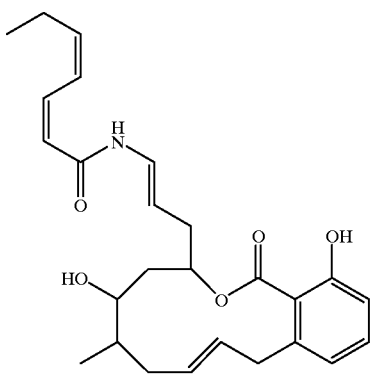

-continued

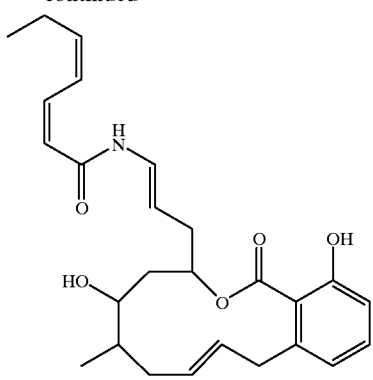

or a pharmaceutically acceptable salt, an ester, or a prodrug thereof.

4. A composition comprising an anticancer effective amount of at least one compound of the formula:

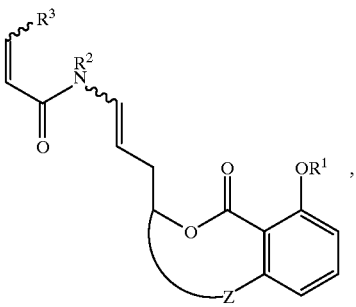

(I)

wherein $R^1$ and $R^2$ are the same or different and are independently H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated alkyl, or aryl; $R^3$ is H, $C_1$–$C_6$ straight-chain or branched saturated or unsaturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms which, together with the five atoms beginning with the carbon of the aromatic ring in meta-relationship with $OR^1$ and ending with the carbon directly attached to the alkyl oxygen of the lactone, said carbons being covalently bonded to either end of linker Z, integrally form a 12–15 membered ring; or a pharmaceutically acceptable salt, an ester, or a prodrug thereof; and a pharmaceutically acceptable carrier.

5. The composition of claim 4 comprising an anticancer effective amount of at least one compound of formula (I), or a pharmaceutically acceptable salt, an ester, or a prodrug thereof, wherein, when Z is a contiguous linker comprising a chain of 10 atoms, $R^3$ is not an oxime methyl ether; and a pharmaceutically acceptable carrier.

6. The composition of claim 4 comprising an anticancer effective amount of at least one compound selected from the group consisting of:

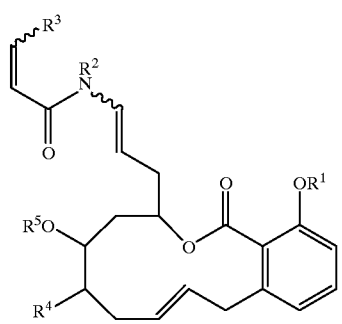

(IA)

and

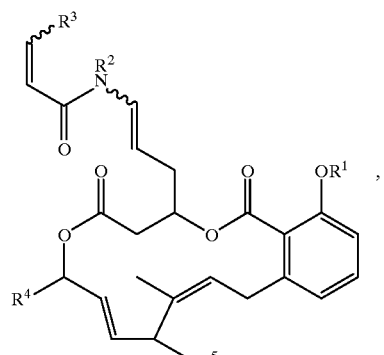

(IB)

wherein $R^1$–$R^3$ are as defined in claim 4; $R^4$ is H, $C_1$–$C_6$ alkyl, or $R^7CH_2$—, wherein $R^7$ is $R^6O$—, $R^6CO_2$—, or $R^6SO_3$—; and $R^5$ is H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated or unsaturated alkyl, or aryl; or a pharmaceutically acceptable salt, an ester, or a prodrug thereof; and a pharmaceutically acceptable carrier.

7. The composition of claim 4 comprising an anticancer effective amount of at least one compound selected from the group consisting of:

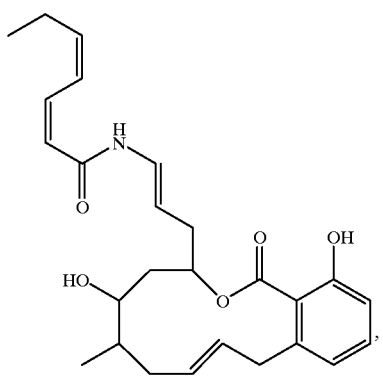

Salicylihalamide A

-continued

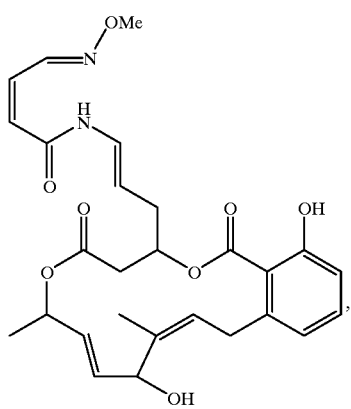

Lobatamide A

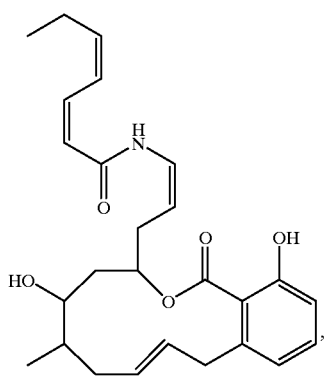

Salicylihalamide B

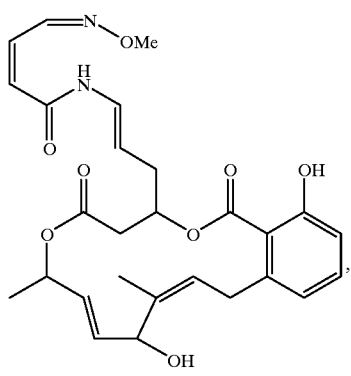

Lobatamide B

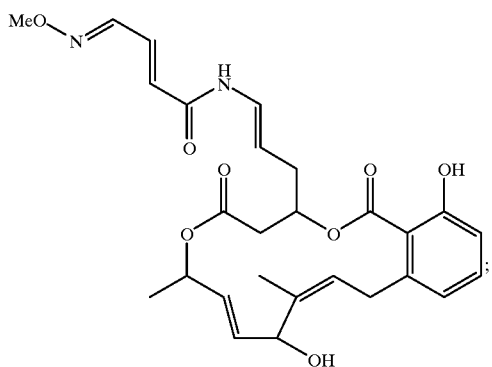

Lobatamide C

-continued

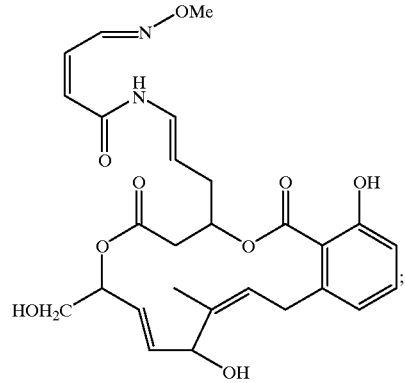

Lobatamide D

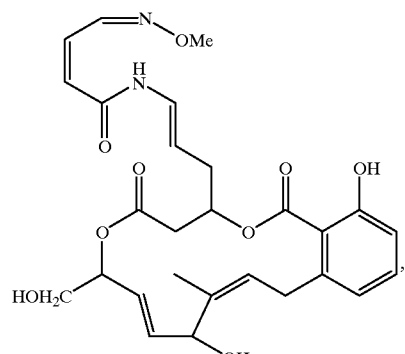

Lobatamide E and

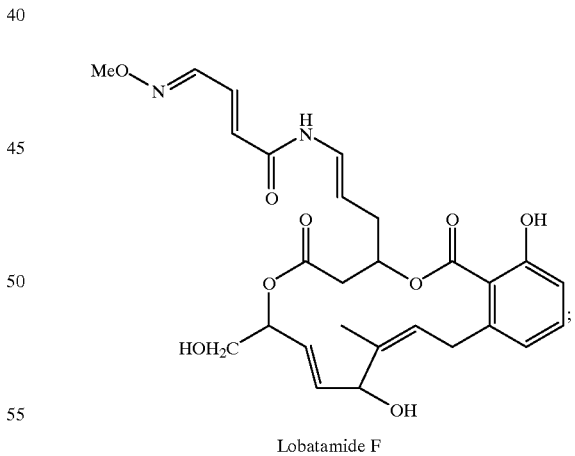

Lobatamide F or a pharmaceutically acceptable salt, an ester or a prodrug thereof; and a pharmaceutically acceptable carrier.

8. The composition of claim 4 comprising an anticancer effective amount of at least one compound selected from the group consisting of:

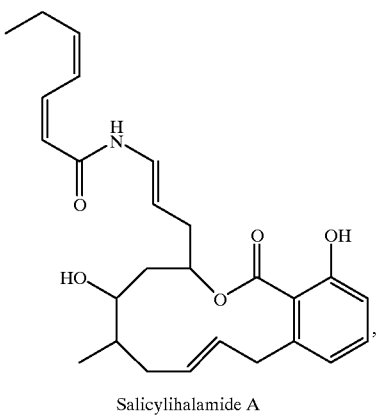
Salicylihalamide A

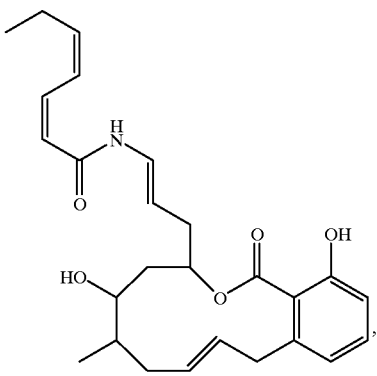
Salicylihalamide B

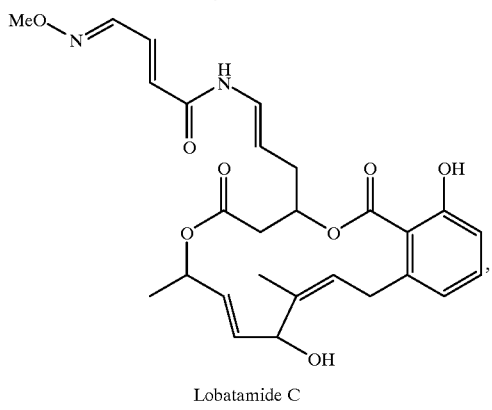
Lobatamide C
and

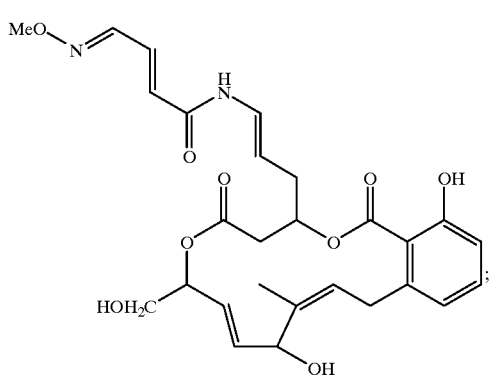
Lobatamide F;

and a pharmaceutically acceptable carrier.

9. The composition of claim 4 which further comprises an anticancer effective amount of at least one additional compound other than a compound of claim 4.

10. A method of preventing or treating cancer, which method comprises administering to a patient in need thereof an anticancer effective amount of at least one compound of the formula:

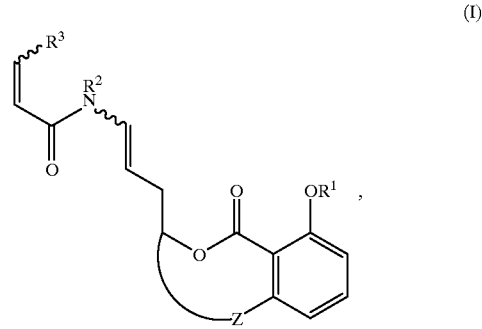

(I)

wherein $R^1$ and $R^2$ are the same or different and are independently H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated alkyl, or aryl; $R^3$ is H, $C_1$–$C_6$ straight-chain or branched-chain saturated or unsaturated alkyl, aryl, an oxime, or an oxime methyl ether; at least one aromatic ring position is optionally substituted with a substituent selected from the group consisting of halo, nitro, amino, hydroxyl, thio, acyl, $C_1$–$C_6$ alkyl, and cyano; and Z is a contiguous linker comprising a chain of 7–10 atoms which, together with the five atoms beginning with the carbon of the aromatic ring in meta-relationship with $OR^1$ and ending with the carbon directly attached to the alkyl oxygen of the lactone, said carbons being covalently bonded to either end of linker Z, integrally form a 12–15 membered ring; or a pharmaceutically acceptable salt, an ester, or a prodrug thereof.

11. The method of claim 10, which method comprises administering to a patient in need thereof an anticancer effective amount of at least one compound of formula (I), or a pharmaceutically acceptable salt, an ester, or a prodrug thereof, wherein when Z is a contiguous linker comprising a chain of 10 atoms, $R^3$ is not an oxime methyl ether.

12. The method of claim 10, which method comprises administering to a patient in need thereof an anticancer effective amount of at least one compound selected from the group consisting of:

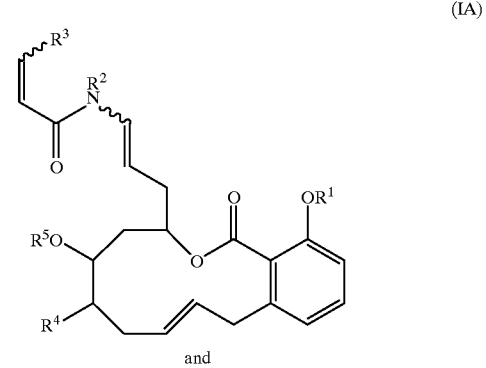

(IA)

and

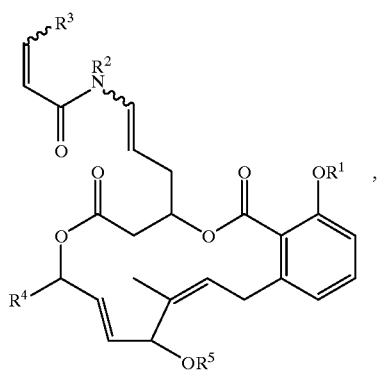

wherein $R^1$–$R^2$ are as defined in claim 10; $R^4$ is H, $C_1$–$C_6$ alkyl, or $R^7CH_2$—, wherein $R^7$ is $R^6O$—, $R^6CO_2$—, or $R^6SO_3$—; and $R^5$ is H, $C_1$–$C_6$ straight-chain or branched saturated or unsaturated alkyl, aryl, $R^6CH_2$—, $R^6CO$—, or $R^6SO_2$—, wherein $R^6$ is H, $C_1$–$C_6$ straight-chain or branched saturated or unsaturated alkyl, or aryl; or a pharmaceutically acceptable salt, an ester, or a prodrug thereof.

13. The method of claim 10 which method comprises administering to a patient in need thereof an anticancer effective amount of at least one compound selected from the group consisting of:

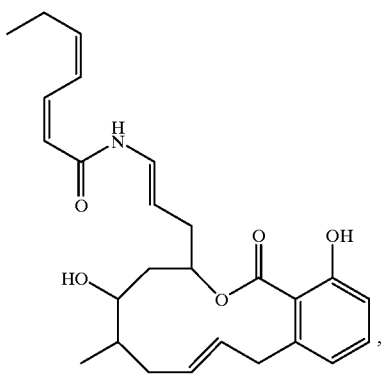

Salicylihalamide A

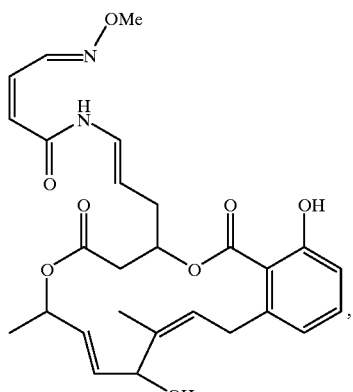

Lobatamide A

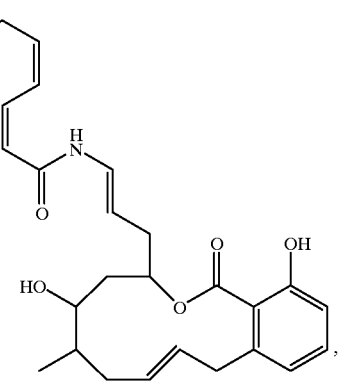

Salicylihalamide B

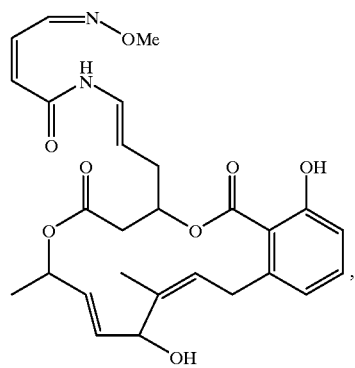

Lobatamide B

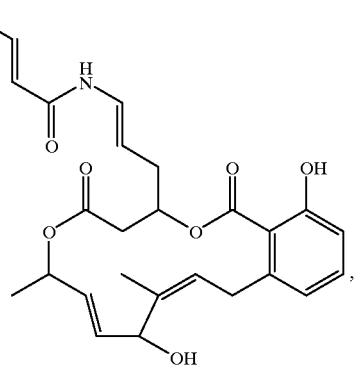

Lobatamide C

-continued

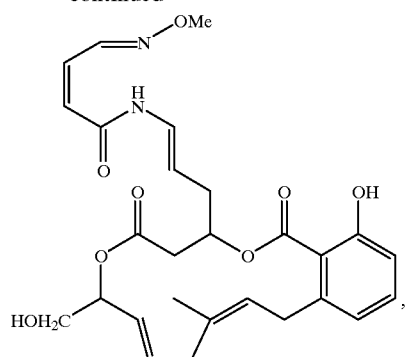

Lobatamide D

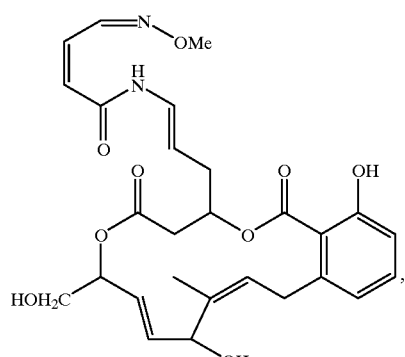

Lobatamide E and

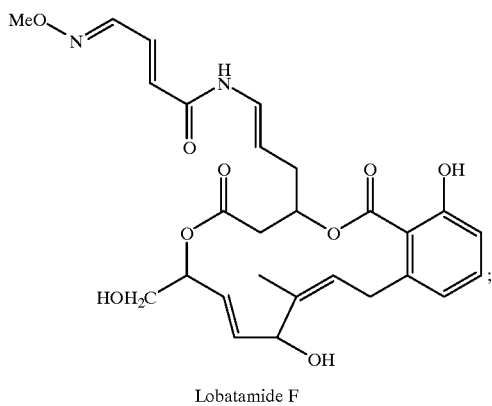

Lobatamide F or a pharmaceutically acceptable salt, an ester, or a prodrug thereof.

14. The method of claim 10 which method comprises administering to a patient in need thereof an anticancer effective amount of at least one compound selected from the group consisting of:

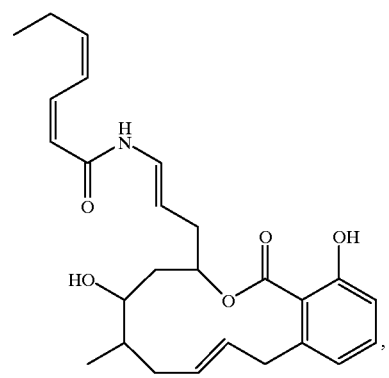

Salicylihalamide A

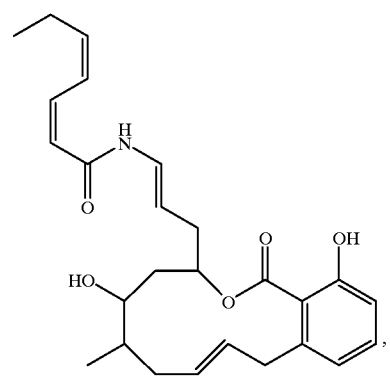

Salicylihalamide B

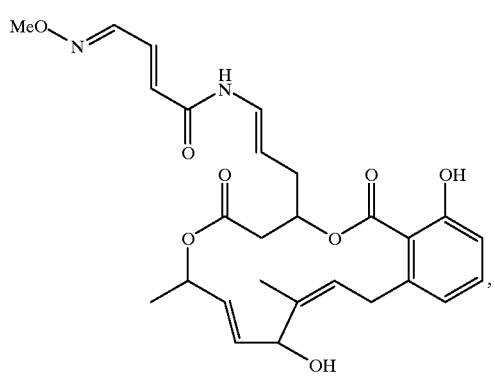

Lobatamide C
and

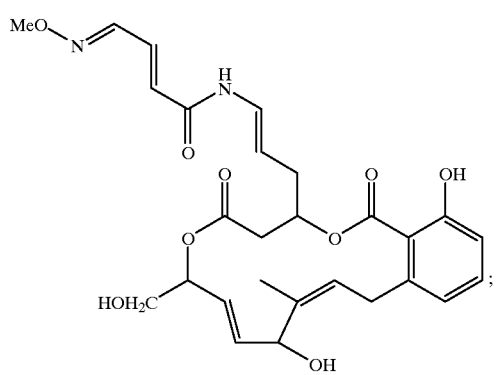

Lobatamide F or a pharmaceutically acceptable salt, an ester, or a prodrug thereof.

15. The method of claim 10, which further comprises coadministering to a patient in need thereof an anticancer effective amount of at least one additional compound other than a compound of claim 10.

16. The composition of claim 6 comprising an anticancer effective amount of at least one compound selected from the group consisting of:

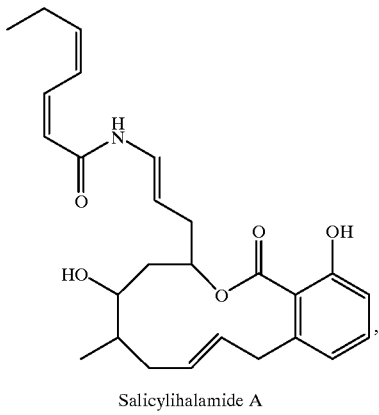

Salicylihalamide A

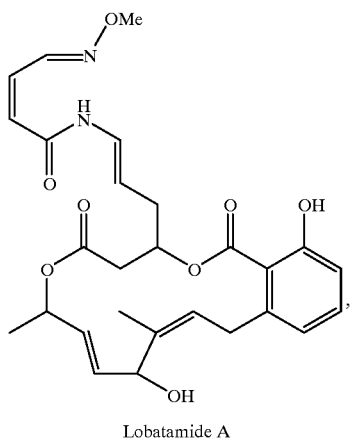

Lobatamide A

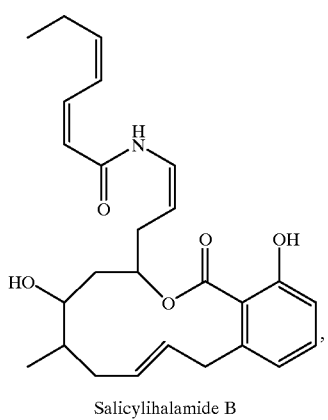

Salicylihalamide B

-continued

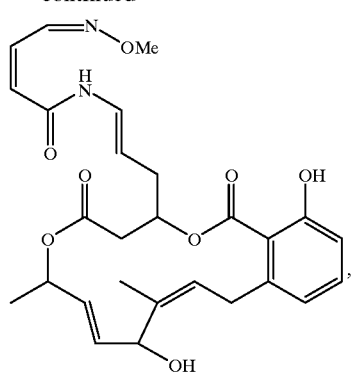

Lobatamide B

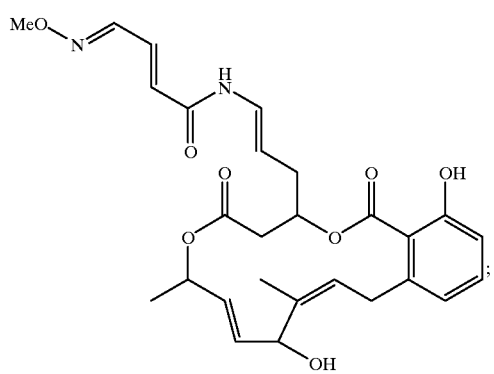

Lobatamide C

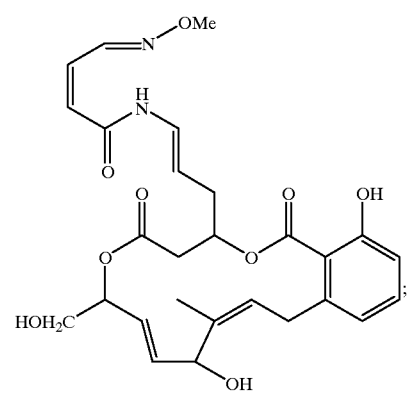

Lobatamide D

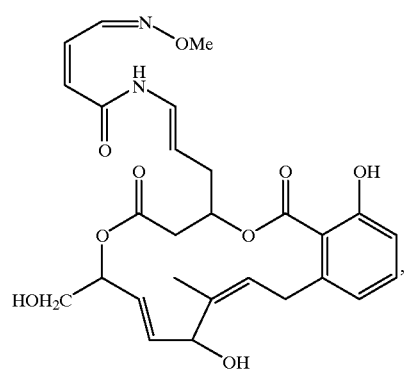

Lobatamide E and

-continued

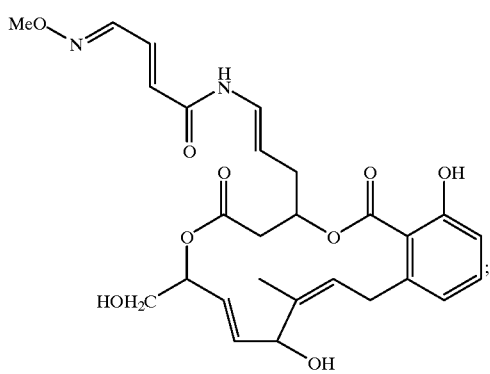

Lobatamide F

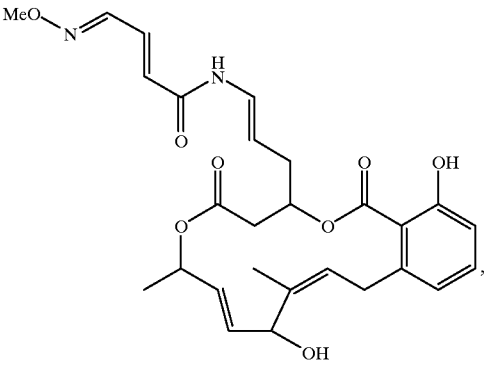

Lobatamide C or a pharmaceutically acceptable salt, an ester, or a prodrug thereof; and a pharmaccutically aceptable carrier.

17. The composition of claim 6 comprising an anticancer effective amount of at least one compound selected from the group consisting of:

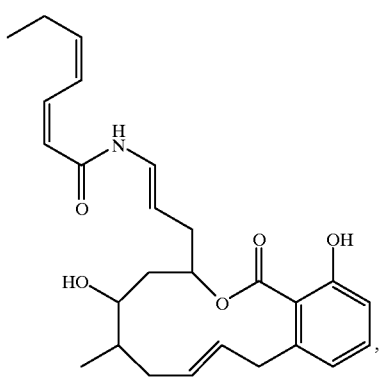

Salicylihalamide A and

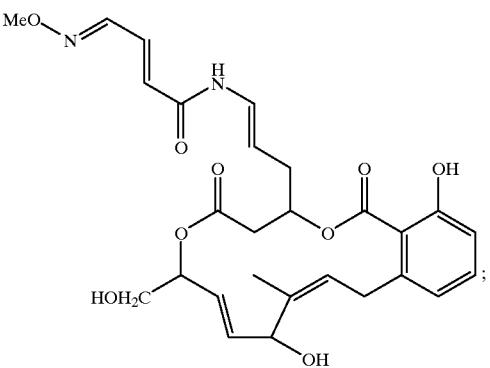

Lobatamide F and a pharmaceutically acceptable carrier.

18. The composition of claim 7 comprising an anticancer effective amount of at least one compound selected from the group consisting of:

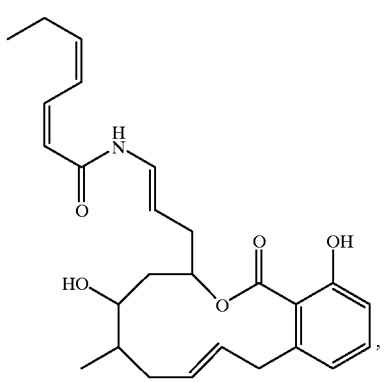

Salicylihalamide B

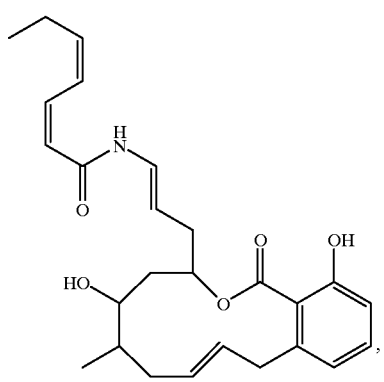

Salicylihalamide A

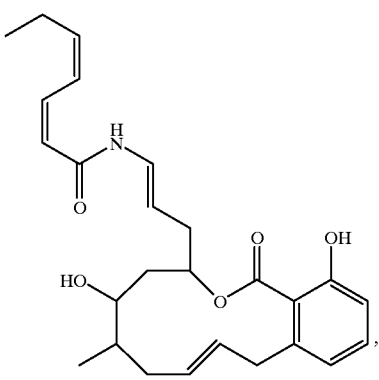
Salicylihalamide B
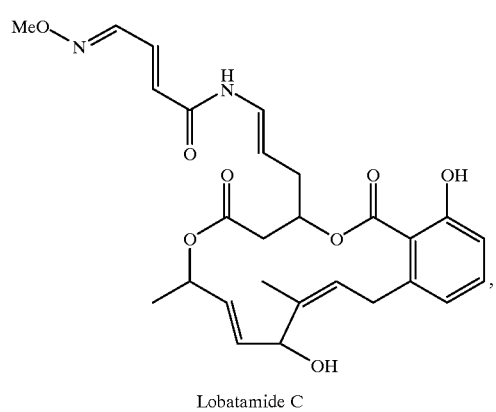
Lobatamide C
and
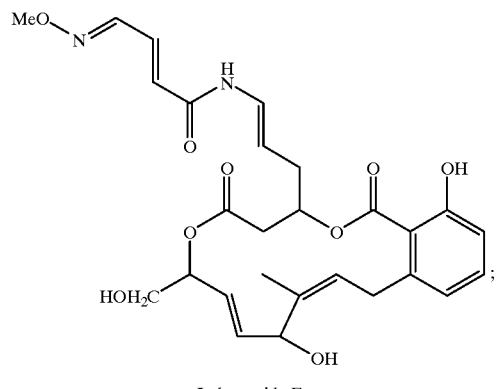
Lobatamide F
and a pharmaceutically acceptable carrier.
19. The method of claim 12 which method comprises administering to a patient in need thereof an anticancer effective amount of at least one compound selected from the group consisting of:
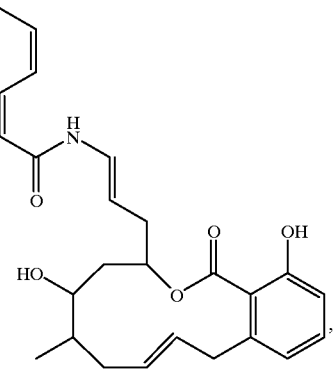
Salicylihalamide A
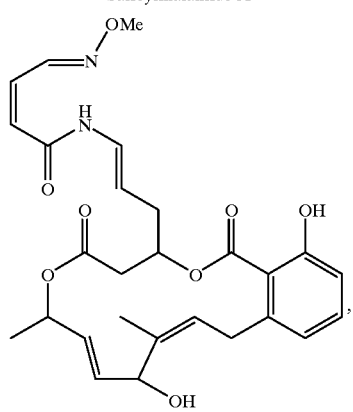
Lobatamide A
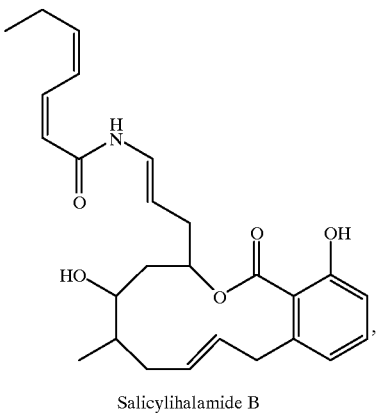
Salicylihalamide B
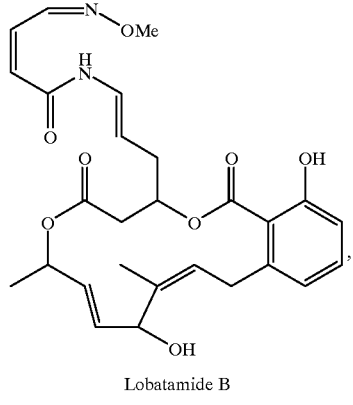
Lobatamide B -continued

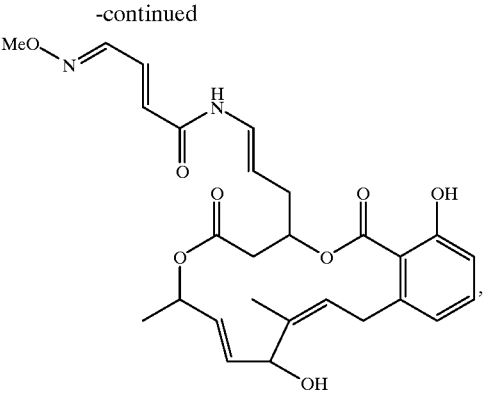

Lobatamide C

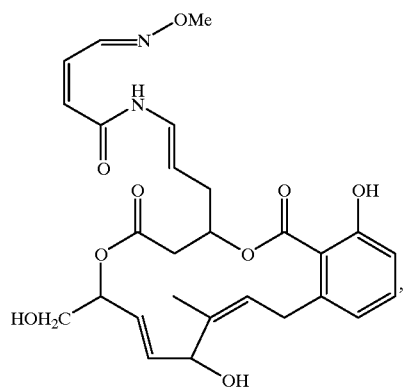

Lobatamide D

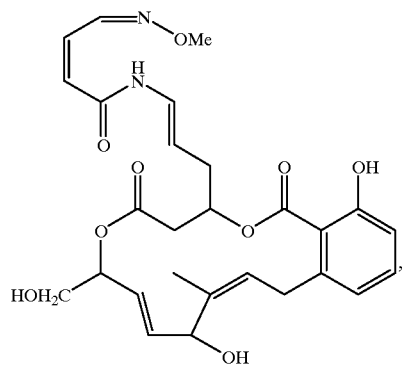

Lobatamide E
and

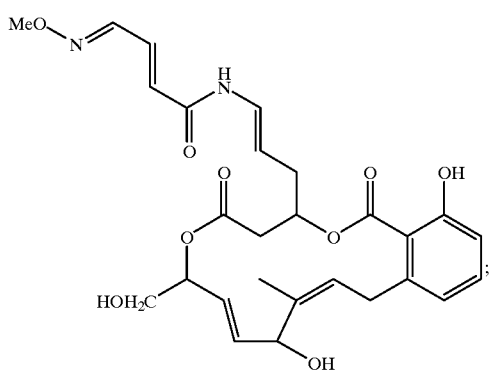

Lobatamide F or a pharmaceutically acceptable salt, an ester, or a prodrug thereof.

20. The method of claim 12 which method comprises administering to a patient in need thereof an anticancer effective amount of at least one compound selected from the group consisting of:

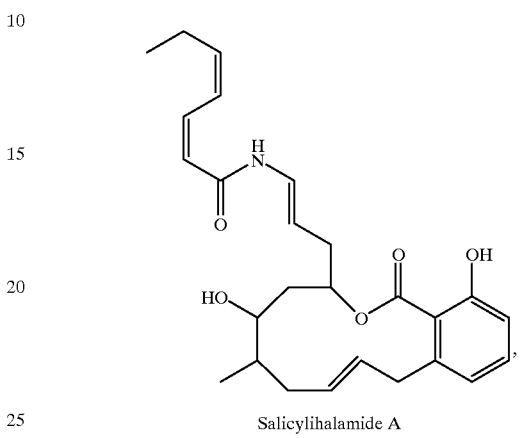

Salicylihalamide A

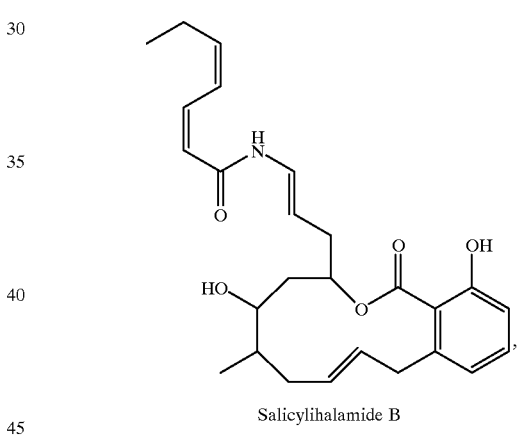

Salicylihalamide B

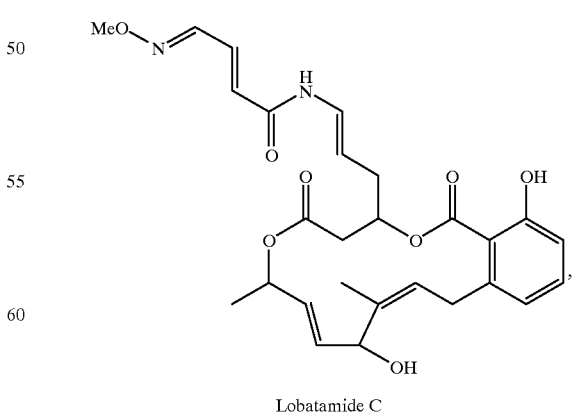

Lobatamide C
and

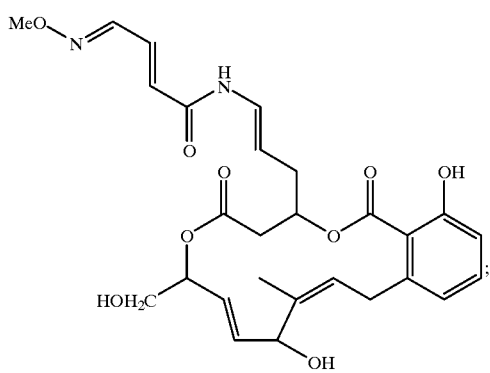

Lobatamide F or a pharmaceutically acceptable salt, an ester, or a prodrug thereof.

21. The method of claim 13 which method comprises administering to a patient in need thereof an anticancer effective amount of at least one compound selected from the group consisting of:

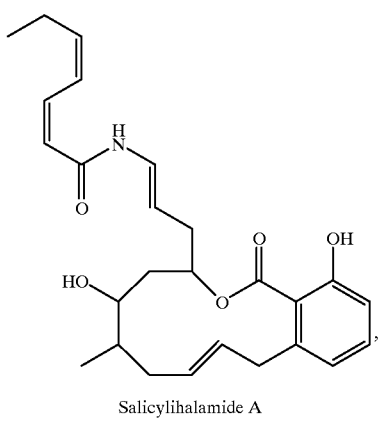

Salicylihalamide A

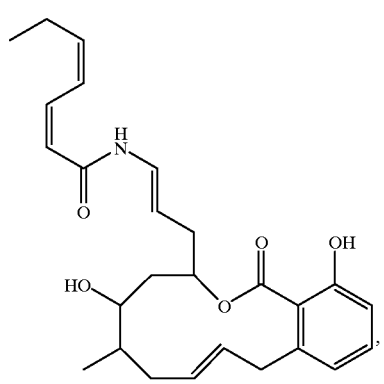

Salicylihalamide B

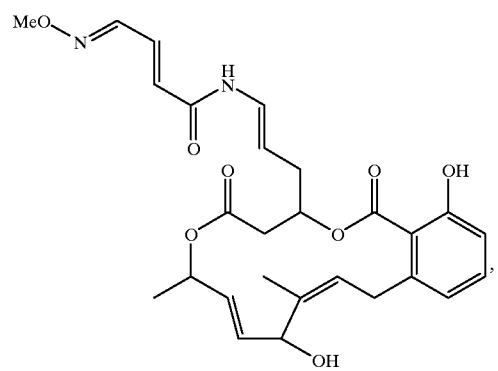

Lobatamide C and

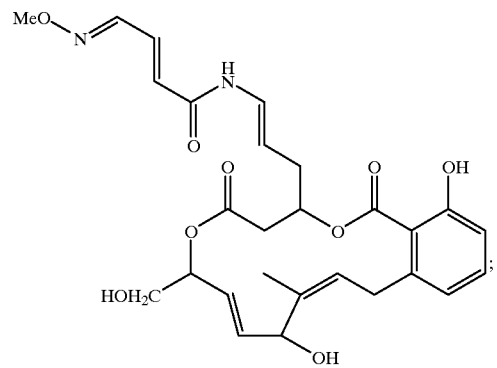

Lobatamide F or a pharmaceutically acceptable salt, an ester, or a prodrug thereof.

* * * * *